United States Patent [19]

Anderson et al.

[11] Patent Number: 5,935,840
[45] Date of Patent: Aug. 10, 1999

[54] ACTIVATED RECOMBINANT ADENOVIRUS PROTEINASES

[75] Inventors: Carl W. Anderson, Stony Brook; Walter F. Mangel, Shoreham, both of N.Y.

[73] Assignee: Associated Universities, Inc., Washington, D.C.

[21] Appl. No.: 08/435,998

[22] Filed: May 5, 1995

Related U.S. Application Data

[60] Division of application No. 08/155,171, Nov. 19, 1993, Pat. No. 5,543,264, which is a continuation-in-part of application No. 07/851,217, Mar. 13, 1992, abandoned, which is a continuation-in-part of application No. 07/545,585, Jun. 29, 1990, abandoned.

[51] Int. Cl.$^6$ .......................... C12N 15/63; C12N 15/70; C12N 15/57; C12N 9/50

[52] U.S. Cl. ................. 435/252.3; 435/69.1; 435/172.3; 435/252.33; 435/320.1; 536/23.2; 536/23.4

[58] Field of Search ........................... 435/219, 23, 69.1, 435/68.1, 69.7, 252.3, 252.33, 172.3; 536/23.2, 23.4

[56] References Cited

U.S. PATENT DOCUMENTS

| | | | |
|---|---|---|---|
| 5,238,919 | 8/1993 | Zimmerman et al. | 514/8 |
| 5,543,264 | 8/1996 | Anderson et al. | 324/219 |

OTHER PUBLICATIONS

Yeh–Kai, L., et al., Journal of Molecular Biology, vol. 167, "Genetic identification of an endoproteinase encoded by the adenovirus genome", pp. 217–222, 1983.

Tremblay, M. L., et al., Biochimica et Biophysica Acta, vol. 734, "In vitro cleavage specificity of the adenovirus type 2 proteinase", pp. 239–245, 1983.

Chatterjee, P. K., et al., Proceedings of the National Academy of Sciences, U.S.A., vol. 87, "Adenovirus Type 2 endopeptidase:An unusual phosphoprotein enzyme matured by autocatalysis", pp. 714–718, 1987.

Houde, A., et al., Gene, vol. 54, "Sequence of the protease of human subgroup E adenovirus type 4", pp. 51–56, 1987.

Houde, A., et al., Nucleic Acids Research, vol. 16, "The primary structure of human adenovirus type 12 protease", p. 7195, 1988.

Houde, A., et al., Nucleic Acids Research, vol. 16, "Sequence of the human adenovirus type 3 protease", p 11374, 1988.

Anderson, C. W., et al., Virology, vol. 172, "Characterization of the adenovirus 2 virion protein Mu", pp. 506–512, 1989.

Lopez–Otin, C., et al., Journal of Biological Chemistry, vol. 264, "Gly–Gly–X, a novel consensus sequence for the proteolytic processing of viral and cellular proteins", pp. 9107–9110, 1989.

Webster, A., et al., Journal of General Virology, vol. 70, "Characterization of the adenovirus proteinase: Substrate specificity", pp. 3225–2334, 1989.

Cai, F., et al., Nucleic Acids Research, vol. 18, "Nucleotide and deduced amino acid sequence of the bovine adenovirus type 7 proteinase", p. 5567, 1990.

Cai, F. et al., Nucleic Acids Research, vol. 18, "Nucleotide and deduced amino acid sequence of the bovine adenovirus type 3 proteinase", p. 5568, 1990.

(List continued on next page.)

*Primary Examiner*—Keith D. Hendricks
*Assistant Examiner*—William W. Moore
*Attorney, Agent, or Firm*—Margaret C. Bogosian

[57] ABSTRACT

This application describes methods and expression constructs for producing activatable recombinant adenovirus proteinases. Purified activatable recombinant adenovirus proteinases and methods of purification are described. Activated adenovirus proteinases and methods for obtaining activated adenovirus proteinases are further included. Isolated peptide cofactors of adenovirus proteinase activity, methods of purifying and identifying said peptide cofactors are also described. Antibodies immunoreactive with adenovirus proteinases, immunospecific antibodies, and methods for preparing them are also described. Other related methods and materials are also described.

3 Claims, 25 Drawing Sheets

OTHER PUBLICATIONS

Weber, J. M., Seminars in Virology, vol. 1, "The adenovirus proteinase", pp. 379–384, 1990.

Houde, A., et al., Gene, vol. 88, "Adenovirus proteinase: Comparison of amino acid sequences and expression of the cloned cDNA in *Escherichia coli*", pp. 269–273, 1990.

Anderson, C. W., Virology, vol. 177, "The proteinase polypeptide of adenovirus serotype 2 virions", pp. 259–272, 1990.

Houde, A., et al., Virology, vol. 77, "Adenovirus type 2 precursor proteins are cleaved by proteinases of other adenoviruses", pp. 485–486, 1990.

Webster, A., et al., Cell, vol. 72, "The adenovirus protease is activated by a virus–coded disulphide–linked peptide", pp. 97–104, 1993.

Tihayni, K., et al., Journal of Biological Chemistry, vol. 268, "Isolation and properties of adenovirus type 2, proteinase", pp. 1780–1785, 1993.

Webster, A., et al., Journal of General Virology, vol. 74, "The active adenovirus protease is the intact L3 23K protein", pp. 1415–1420, 1993.

Freimuth, P., et al., Virology, vol. 193, "Human adenovirus serotype 12 virion precursors pMu and pVI are cleaved at amino–terminal and and carboxy–terminal sites that conform to the adenovirus 2 endoproteinase cleavage consensus sequence", pp. 348–355, 1993.

Anderson, C. W., et al., Protein Expression and Purification, vol. 4 Expression and purification of the adenovirus proteinase polypeptide and of a synthetic proteinase substrate, pp. 8–15, 1993.-

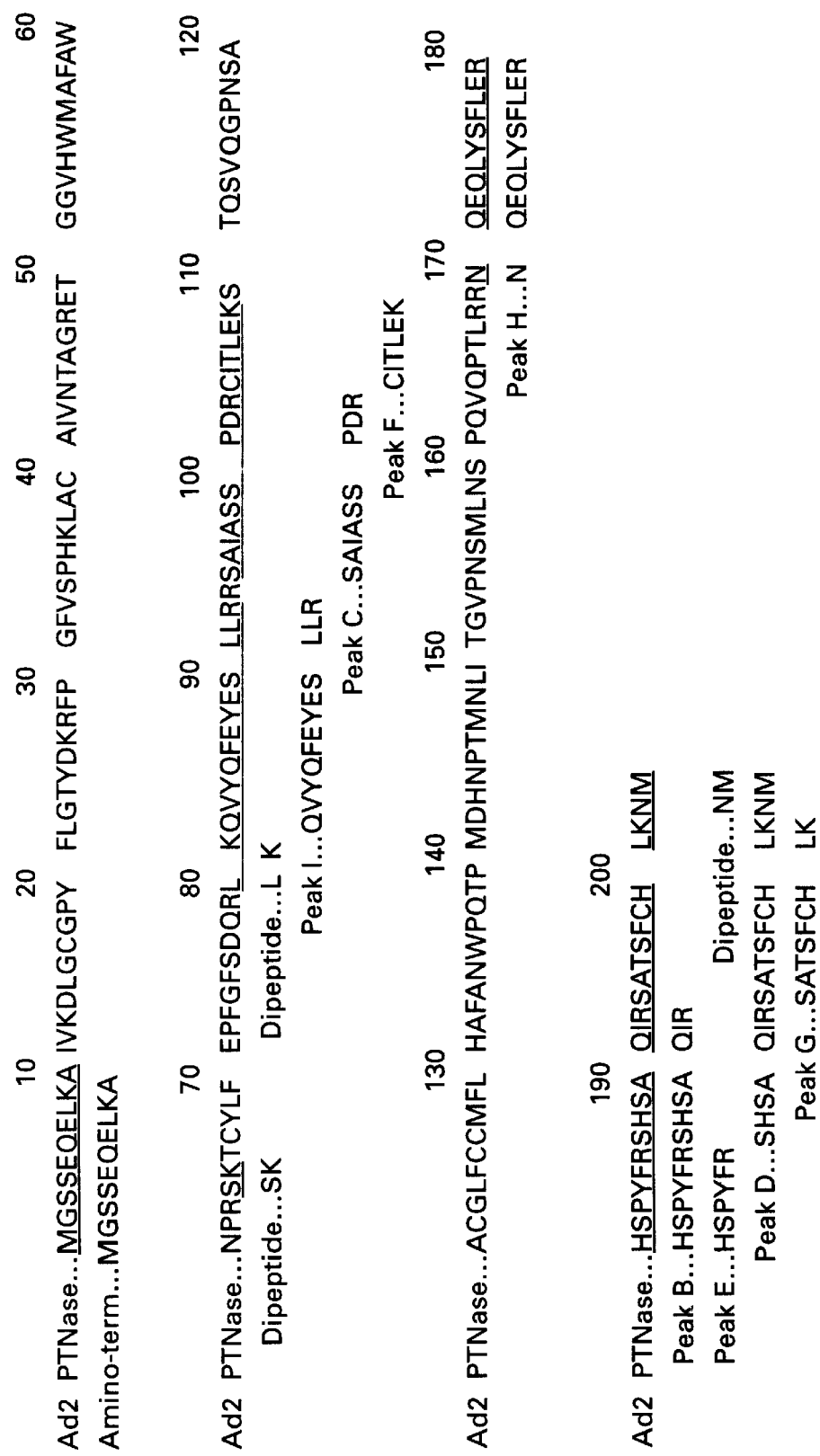

Peak a  1  GVQSL?RRR?  F
Peak b  1  GVQSL?RRR?  F
Peak c  1  GVQSL?RRR?  F

P-VI  1    MEDINFASLA  PREGSRPFMG  NWQDIGTSNM  SGGAFSWGSL
      41   WSGIKNFGST  IKNYGSKAWN  SSTGQMLRDK  LKEQNFQQKV
      81   VDGLASGISG  VVDLANQAVQ  NKINSKLDPR  PPVEEPPPAV
      121  ETVSPEGRGE  KRPRPDREET  LVTQIDEPPS  YEEALKQGLP
      161  TTRPIAPMAT  GVLGQHTPVT  LDLPPPADTQ  QKPVLPGPSA
      201  VVVTRPSRAS  LRRAASGPRS  MRPVASGNWQ  STLNSIVGLG
      241  VQSLKRRRCF

FIGURE 12

```
                       5         10        15        20        25        30        35
                       ==----======  ==--------======  =========---======
Ad2   1  M - - - - - - G S S E Q E L K A I V K D L G C G P Y F L G T Y D K R F
Ad5   1  M - - - - - - G S S E Q E L K A I V K D L G C G P Y F L G T Y D K R F
Ad12  1  M - - - - - - G S S E Q E L T A I V R D L G C G P Y F L G T F D K R F
Ad41  1  M - - - - - - G S S E Q E L V A I A R D L G C G S Y F L G T F D K R F
Ad40  1  M - - - - - - G S S E Q E L V A I V R E L G C G P Y F L G T F D K R F
Ad3   1  M T C G S G N G S S E Q E L K A I V R D L G C G P Y F L G T F D K R F
Ad4   1  M - - - - A A G S G E Q E L R A I L R D L G C G P Y F L G T F D K R F
BAd3  1  M - - - - - - G S R E E E L R F I L H D L G V G P Y F L G T F D K H F
BAd7  1  M - - - - - S G L S E K E V F L L L S S L Q C T H G F L G T F D C R F

*
         ======------=  --------===================  ===----=  --======---
Ad2   30 P G F V S P H K L A C A I V N T A G R E T G G V H W M A F A W N P R S
Ad5   30 P G F V S P H K L A C A I V N T A G R E T G G V H W M A F A W N P R S
Ad12  30 P G F V S R D R L S C A I V N T A G R E T G G V H W L A F G W N P K S
Ad41  30 P G F M A P N K L A C A I V N T A G R E T G G V H W L A F A W N P K S
Ad40  30 P G F M A P H K L A C A I V N T A G R E T G G V H W L A F A W N P K N
Ad3   36 P G F M A P N K L A C A I V N T A G R E T G G E H W L A F G W N P R Y
Ad4   32 P G F M A P H K V A C A I V N T A G R E T G G E H W L A F A W N P R S
BAd3  30 P G F M S K N R M S C A I V N T A G R E T G G V H W L A F A W H P A S
BAd7  31 P G F M N N V K L Q T A I V N T G P R E Q G G I H W L A F A W D P K S

========---=======  =======----  =========---=======  ===------===----=---
AD2   65 K T C Y L F E P F G F S D Q R L K Q V Y Q F E Y E S L L R R S A I A S
AD5   65 K T C Y L F E P F G F S D Q R L K Q V Y Q F E Y E S L L R R S A I A S
AD12  65 H T C Y L F D P F G F S D Q R L K Q I Y Q F E Y E S L L K R S A I A A
AD41  65 H T C Y L F D P F G F S D E R L K Q I Y Q F E Y E G L L K R S A I A S
AD40  65 R T C Y L F D P F G F S D E R L K Q I Y Q F E Y E G L L R R S A I A S
AD3   71 N T C Y L F D P F G F S D E R L K Q I Y Q F E Y E G L L R R S A I A S
AD4   67 N T C Y L F D P F G F S D Q R L K Q I Y Q F E Y E G L L R R S A I A T
BAD3  65 Q T F Y M F D P F G F S D Q K L K Q I Y N F E Y Q G L L K R S A I T S
BAD7  66 Y Q M F I L D P L G W K N D Q L M K Y Y K F S Y E N L L K R S A I - S

*                                                *
         =-----=----=  ----===-----  ===========  ===------
AD2  100 S P D R C I T L E K S T Q S V Q G P - - - - - N S A A C G L F C C M F
AD5  100 S P D R C I T L E K S T Q S V Q G P - - - - - N S A A C G L F C C M F
AD12 100 T K D R C V T L E K S T Q T V Q G P - - - - - F S A A C G L F C C M F
AD41 100 T P D H C I T L V K S T Q T V Q G P - - - - - F S A A C G L F C C M F
AD40 100 T P D H C I T L I K S T Q T V Q G P - - - - - F S A A C G L F C C M F
AD3  106 K - D R C I T L E K S T Q S V Q G P - - - - - R S A A C G L F C C M F
AD4  102 K - D R C V T W - K S H Q T C R V R V G R C G F S A A C S T A C - - -
BAD3 100 T A D R C L T L I Q S T Q S V Q G P - - - - - N S A A C G L F C C M F
BAD7 100 S P D K C V K V I K N S Q S V Q C T - - - - - C A G S C G L F C V F F
```

Legend:

=== Amino acid sequence is identical in ALL sequenced serotypes
--- Conservative amino acid sequence substitutions among sequenced serotypes
* Predicted Active Site Residue for serine or cysteine proteinase
Pro-137 of Ad2 change to Leu in Ad2tsl mutant

FIGURE 16A

```
Ad2  130  L H A F A N W P Q T P M D H N P T M N L I T G V P N S M L N S P Q V Q
Ad5  130  L H A F A N W P Q T P M D H N P T M N L I T G V P N S M K N S P Q V Q
Ad12 130  L H A F T H W P D H P M D K N P T M D L L T G V P N C M L Q S P Q V V
Ad41 130  L H A F I H W P S N P M E Q N P T M D L L T G V P N S M L Q S P Q V E
Ad40 130  L H A F V N W P T S P M E R N P T M D L L T G V P N S M L Q S P Q V V
Ad3  135  L H A F V H W P D R P M D G N P T M K L V T G V S N S M L Q S P Q V Q
Ad4  131  - - - - - A W P - T P M D K N P T M N L L T G V P N G M L Q S P Q V E
BAd3 130  L H A F V R W P L R A M D N N P T M N L I G H V P N N M L E S P S S Q
BAd7 130  L Y C F Y K Y K S N A F K N C L F Q S L Y G S I P S - - L T P P N - P

Ad2  165  P T L R R N Q E Q L Y S F L E R H S P Y F R S H S A Q I R S A T S F C
Ad5  165  P T L R R N Q E Q L Y S P L E R H S P Y F R S H S A Q I R S A T S F C
Ad12 165  G T L Q R N Q N E L Y K F L N S L S P Y F R H N R E R I E K A T S F T
Ad41 165  P T L R R N Q E R L Y R F L T Q H S P Y F R R H R E R I E K A T A F D
Ad40 165  P T L R R N Q E R L Y R F L A Q R S P Y F Q R H C E R I K K A T A F D
Ad3  170  P T L R R N Q E V L Y R F L N T H S S Y F R S H R A R I E R A T A F D
Ad4  161  P T L R R N Q E A L Y R F L N S H S A Y F R S H R A R I E K A T A F D
BAd3 165  N V F L R N Q Q N L Y R F L R R H S P H F V K H A A Q I E A D T A F D
BAd7 162  T N L H K N Q D F L Y K F F K E K S L Y F R Q N E E Y I V S N T K I G

Ad2  200  H L K N M *                    (204 aa)
Ad5  200  H L K N M *                    (204 aa)
Ad12 200  K M Q N G L K *                (206 aa)
Ad41 200  Q M K N A Q V L F H N K I F Y * (214 aa)
Ad40 200  Q M K N N M *                  (205 aa)
Ad3  205  R M D M Q *                    (209 aa)
Ad4  196  R M N Q D M *                  (201 aa)
BAd3 200  K M L T N *                    (204 aa)
BAd7 197  L I K S H I *                  (202 aa)
```

Legend:

=== Amino acid sequence is identical in ALL sequenced serotypes
--- Conservative amino acid sequence substitutions among sequenced serotypes
 *  Predicted Active Site Residue for serine or cysteine proteinase
 #  Pro-137 of Ad2 change to Leu in Ad2tsl mutant

FIGURE 16B

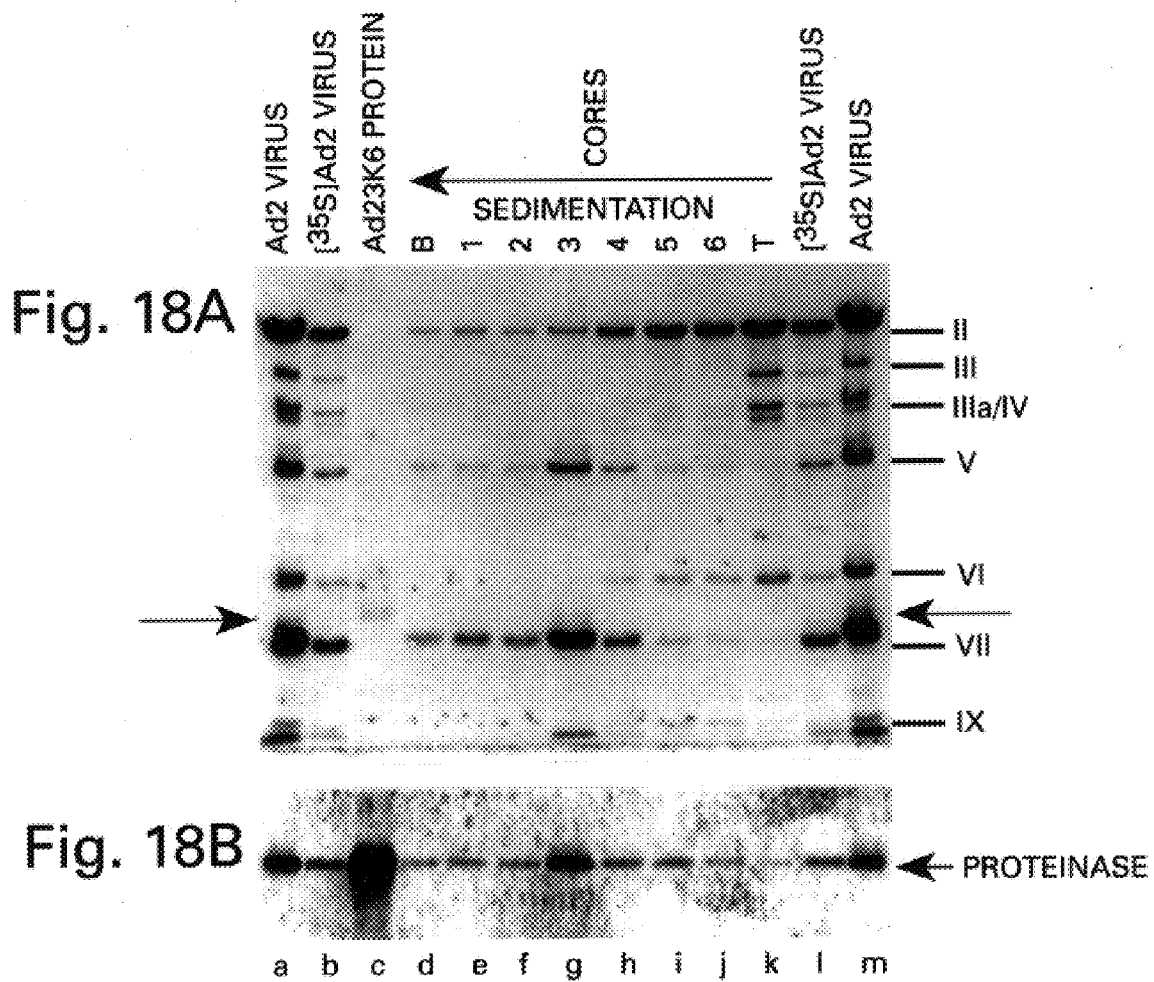

```
pVI  126  V    P    G    S    V    P    T    K    G    E    K    R    P    R    P    D    A    E    E    T    145
     680  GTG  CCC  GGA  TCC  GTT  CCA  ACC  AAA  GGA  GAA  AAG  CGG  CCA  CGG  CCG  GAT  GCA  GAG  GAA  ACC  739 pVI  146  L    V    T    H    T    T    E    P    S    Y    E    E    A    -    K    Q    G    A    A    165
     740  TTA  GTA  ACG  CAC  ACA  ACA  GAA  CCG  TCC  TAT  GAG  GAA  GCA  ATA  AAA  CAA  GGA  GCC  GCT  799 pVI  166  L    S    P    T    T    Y    P    M    T    K    P    I    L    P    M    A    T    R    V    Y    185
     800  CTG  TCA  CCT  ACC  ACC  TAT  CCC  ATG  ACC  AAG  CCT  ATT  TTA  CCC  ATG  GCT  ACT  AGA  GTG  TAT  859 pVI  186  G    K    N    E    N    V    P    M    T    L    E    L    P    P    L    P    E    P    T    -    205
     860  GGA  AAA  AAC  GAA  AAT  GTG  CCT  ATG  ACC  CTT  GAG  CTG  CCT  CCA  TTG  CCA  GAA  CCC  ACT  ATC  919 pVI  206  A    D    P    V    G    S    V    P    V    A    V    P    V    A    S    T    V    S    R    225
     920  GCG  GAT  CCC  GTA  GGT  TCC  GTT  CCT  GTT  GCA  TCT  GCA  GTT  GCA  TCG  ACA  GTG  AGC  CGT  979 pVI  226  P    A    V    R    P    V    A    V    A    S    L    R    N    P    R    S    S    N    W    Q    245
     980  CCA  GCA  GTG  CGG  CCT  GTT  GCC  GTG  GCT  AGC  TTG  CGA  AAC  CCA  CGA  TCC  AGT  AAT  TGG  CAA  1039 pVI  246  S    T    L    N    S    I    V    G    L    G    V    K    S    L    K    R    R    C    Y    265
     1040 AGT  ACC  CTA  AAC  AGT  ATT  GTG  GGA  CTG  GGA  GTA  AAG  TCT  CTC  AAA  CGC  CGA  CGC  TGC  TAC  1099 pVI       *
     1100 TAA  CATTAAAA  AGACGAGTGT  TAATTCCCAT  CTGTGTATAC  GCCTCCTATG  TTAGGCCCAG  AGGACCAA        1158
```

FIGURE 20b

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
      (A) LENGTH: 612 base pairs
      (B) TYPE: nucleic acid
      (C) STRANDEDNESS: double
      (D) TOPOLOGY: linear (ii) MOLECULE TYPE: DNA (genomic)

(ix) FEATURE:
    (A) NAME/KEY: CDS
    (B) LOCATION: 1..612
    (D) OTHER INFORMATION: /product= "Ad2 proteinase"

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GGC | TCC | AGT | GAG | CAG | GAA | CTG | AAA | GCC | ATT | GTC | AAA | GAT | CTT | GGT | 48 |
| Met | Gly | Ser | Ser | Glu | Gln | Glu | Leu | Lys | Ala | Ile | Val | Lys | Asp | Leu | Gly | |
| 1 | | | | 5 | | | | 10 | | | | | 15 | | | |
| TGT | GGG | CCA | TAT | TTT | TTG | GGC | ACC | TAT | GAC | AAG | CGC | TTT | CCA | GGC | TTT | 96 |
| Cys | Gly | Pro | Tyr | Phe | Leu | Gly | Thr | Tyr | Asp | Lys | Arg | Phe | Pro | Gly | Phe | |
| | | | 20 | | | | | 25 | | | | | 30 | | | |
| GTT | TCT | CCA | CAC | AAG | CTC | GCC | TGC | GCC | ATA | GTC | AAT | ACG | GCC | GGT | CGC | 144 |
| Val | Ser | Pro | His | Lys | Leu | Ala | Cys | Ala | Ile | Val | Asn | Thr | Ala | Gly | Arg | |
| | | | 35 | | | | 40 | | | | | 45 | | | | |
| GAG | ACT | GGG | GGC | GTA | CAC | TGG | ATG | GCC | TTT | GCC | TGG | AAC | CCG | CGC | TCA | 192 |
| Glu | Thr | Gly | Gly | Val | His | Trp | Met | Ala | Phe | Ala | Trp | Asn | Pro | Arg | Ser | |
| 50 | | | | | 55 | | | | | 60 | | | | | | |
| AAA | ACA | TGC | TAC | CTC | TTT | GAG | CCC | TTT | GGC | TTT | TCT | GAC | CAA | CGA | CTC | 240 |
| Lys | Thr | Cys | Tyr | Leu | Phe | Glu | Pro | Phe | Gly | Phe | Ser | Asp | Gln | Arg | Leu | |
| 65 | | | | | 70 | | | | | 75 | | | | | 80 | |
| AAG | CAG | GTT | TAC | CAG | TTT | GAG | TAC | GAG | TCA | CTC | CTG | CGC | CGT | AGC | GCC | 288 |
| Lys | Gln | Val | Tyr | Gln | Phe | Glu | Tyr | Glu | Ser | Leu | Leu | Arg | Arg | Ser | Ala | |
| | | | | 85 | | | | | 90 | | | | | 95 | | |
| ATT | GCT | TCT | TCC | CCC | GAC | CGC | TGT | ATA | ACG | CTG | GAA | AAG | TCC | ACC | CAA | 336 |
| Ile | Ala | Ser | Ser | Pro | Asp | Arg | Cys | Ile | Thr | Leu | Glu | Lys | Ser | Thr | Gln | |
| | | | | 100 | | | | | 105 | | | | | 110 | | |
| AGC | GTG | CAG | GGG | CCC | AAC | TCG | GCC | GCC | TGT | GGA | CTA | TTC | TGC | TGC | ATG | 384 |
| Ser | Val | Gln | Gly | Pro | Asn | Ser | Ala | Ala | Cys | Gly | Leu | Phe | Cys | Cys | Met | |
| | | 115 | | | | | 120 | | | | | 125 | | | | |
| TTT | CTC | CAC | GCC | TTT | GCC | AAC | TGG | CCC | CAA | ACT | CCC | ATG | GAT | CAC | AAC | 432 |
| Phe | Leu | His | Ala | Phe | Ala | Asn | Trp | Pro | Gln | Thr | Pro | Met | Asp | His | Asn | |
| | 130 | | | | | 135 | | | | | 140 | | | | | |
| CCC | ACC | ATG | AAC | CTT | ATT | ACC | GGG | GTA | CCC | AAC | TCC | ATG | CTT | AAC | AGT | 480 |
| Pro | Thr | Met | Asn | Leu | Ile | Thr | Gly | Val | Pro | Asn | Ser | Met | Leu | Asn | Ser | |
| 145 | | | | | 150 | | | | | 155 | | | | | 160 | |
| CCC | CAG | GTA | CAG | CCC | ACC | CTG | CGT | CGC | AAC | CAG | GAA | CAG | CTC | TAC | AGC | 528 |
| Pro | Gln | Val | Gln | Pro | Thr | Leu | Arg | Arg | Asn | Gln | Glu | Gln | Leu | Tyr | Ser | |
| | | | | 165 | | | | | 170 | | | | | 175 | | |
| TTC | CTG | GAG | CGC | CAC | TCG | CCC | TAC | TTC | CGC | AGC | CAC | AGT | GCG | CAG | ATT | 576 |
| Phe | Leu | Glu | Arg | His | Ser | Pro | Tyr | Phe | Arg | Ser | His | Ser | Ala | Gln | Ile | |
| | | | 180 | | | | | 185 | | | | | 190 | | | |
| AGG | AGC | GCC | ACT | TCT | TTT | TGT | CAC | TTG | AAA | AAC | ATG | | | | | 612 |
| Arg | Ser | Ala | Thr | Ser | Phe | Cys | His | Leu | Lys | Asn | Met | | | | | |
| | | 195 | | | | | 200 | | | | | | | | | |

(2) INFORMATION FOR SEQ ID NO:2:

(i) SEQUENCE CHARACTERISTICS:
        (A) LENGTH: 204 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Met | Gly | Ser | Ser | Glu | Gln | Glu | Leu | Lys | Ala | Ile | Val | Lys | Asp | Leu | Gly |
| 1 | | | | 5 | | | | 10 | | | | | 15 | | |
| Cys | Gly | Pro | Tyr | Phe | Leu | Gly | Thr | Tyr | Asp | Lys | Arg | Phe | Pro | Gly | Phe |
| | | | 20 | | | | | 25 | | | | | 30 | | |

```
Val Ser Pro His Lys Leu Ala Cys Ala Ile Val Asn Thr Ala Gly Arg
        35                  40                  45

Glu Thr Gly Gly Val His Trp Met Ala Phe Ala Trp Asn Pro Arg Ser
    50                  55                  60

Lys Thr Cys Tyr Leu Phe Glu Pro Phe Gly Phe Ser Asp Gln Arg Leu
65                  70                  75                  80

Lys Gln Val Tyr Gln Phe Glu Tyr Glu Ser Leu Leu Arg Arg Ser Ala
                85                  90                  95

Ile Ala Ser Ser Pro Asp Arg Cys Ile Thr Leu Glu Lys Ser Thr Gln
            100                 105                 110

Ser Val Gln Gly Pro Asn Ser Ala Ala Cys Gly Leu Phe Cys Cys Met
        115                 120                 125

Phe Leu His Ala Phe Ala Asn Trp Pro Gln Thr Pro Met Asp His Asn
    130                 135                 140

Pro Thr Met Asn Leu Ile Thr Gly Val Pro Asn Ser Met Leu Asn Ser
145                 150                 155                 160

Pro Gln Val Gln Pro Thr Leu Arg Arg Asn Gln Glu Gln Leu Tyr Ser
                165                 170                 175

Phe Leu Glu Arg His Ser Pro Tyr Phe Arg Ser His Ser Ala Gln Ile
            180                 185                 190

Arg Ser Ala Thr Ser Phe Cys His Leu Lys Asn Met
        195                 200
```

(2) INFORMATION FOR SEQ ID NO:3:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (xi) SEQUENCE DESCRIPTION: SEQ ID NO:3:

```
ATACATATGC GGGCGAAACT CCTAGGAATA GTCCTGACAA CCCCTATCGC GATCAGCTCT    60

TTTGCGTCGA CCCATATGGG CTCCAGTGAG                                    90
```

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:4:

```
Gly His His His His His His Asn Met
1               5
```

(2) INFORMATION FOR SEQ ID NO:5:

(i) SEQUENCE CHARACTERISTICS:
        (A) LENGTH: 618 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..618
        (D) OTHER INFORMATION: /product= "Ad12 proteinase"

(xi) SEQUENCE DESCRIPTION: SEQ ID NO:5:

```
ATG GGT TCA AGC GAA CAG GAG CTG ACG GCG ATT GTT CGA GAT CTA GGC        48
Met Gly Ser Ser Glu Gln Glu Leu Thr Ala Ile Val Arg Asp Leu Gly
 1               5                  10                  15

TGT GGG CCC TAT TTT TTG GGC ACC TTT GAC AAA CGT TTT CCG GGT TTT        96
Cys Gly Pro Tyr Phe Leu Gly Thr Phe Asp Lys Arg Phe Pro Gly Phe
                 20                  25                  30

GTG TCT CGC GAC CGC TTA TCA TGC GCT ATT GTT AAC ACT GCC GGT CGT       144
Val Ser Arg Asp Arg Leu Ser Cys Ala Ile Val Asn Thr Ala Gly Arg
         35                  40                  45

GAA ACT GGG GGC GTA CAC TGG CTG GCC TTT GGA TGG AAC CCC AAA TCG       192
Glu Thr Gly Gly Val His Trp Leu Ala Phe Gly Trp Asn Pro Lys Ser
 50                  55                  60

CAC ACT TGC TAT TTA TTC GAT CCA TTT GGA TTT TCT GAT CAG CGA CTG       240
His Thr Cys Tyr Leu Phe Asp Pro Phe Gly Phe Ser Asp Gln Arg Leu
 65                  70                  75                  80

AAA CAA ATC TAT CAG TTT GAG TAC GAA AGT CTG TTG CGC CGT AGT GCG       288
Lys Gln Ile Tyr Gln Phe Glu Tyr Glu Ser Leu Leu Arg Arg Ser Ala
                 85                  90                  95

CTA GCG GCC ACT AAA GAC CGA TGC GTC ACC CTA GAA AAG TCA ACC CAA       336
Leu Ala Ala Thr Lys Asp Arg Cys Val Thr Leu Glu Lys Ser Thr Gln
        100                 105                 110

ACT GTA CAA GGA CCG TTT TCT GCA GCG TGC GGC CTG TTT TGT TGT ATG       384
Thr Val Gln Gly Pro Phe Ser Ala Ala Cys Gly Leu Phe Cys Cys Met
115                 120                 125

TTC TTA CAT GCT TTT ACT CAC TGG CCT GAC CAT CCA ATG GAT AAA AAT       432
Phe Leu His Ala Phe Thr His Trp Pro Asp His Pro Met Asp Lys Asn
        130                 135                 140

CCC ACT ATG GAC CTA CTT ACT GGG GTG CCT AAT TGT ATG CTA CAA AGT       480
Pro Thr Met Asp Leu Leu Thr Gly Val Pro Asn Cys Met Leu Gln Ser
145                 150                 155                 160

CCT CAG GTA GTG GGC ACA CTT CAA CGC AAT CAG AAT GAA TTG TAT AAA       528
Pro Gln Val Val Gly Thr Leu Gln Arg Asn Gln Asn Glu Leu Tyr Lys
                165                 170                 175

TTC TTA AAC AGT CTG TCC CCT TAC TTT CGT CAC AAC CGC GAG CGC ATA       576
Phe Leu Asn Ser Leu Ser Pro Tyr Phe Arg His Asn Arg Glu Arg Ile
        180                 185                 190

GAA AAA GCT ACA TCT TTT ACT AAA ATG CAA AAT GGA CTC AAA               618
Glu Lys Ala Thr Ser Phe Thr Lys Met Gln Asn Gly Leu Lys
195                 200                 205
```

(2) INFORMATION FOR SEQ ID NO:6:

(i) SEQUENCE CHARACTERISTICS:
        (A) LENGTH: 206 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Ser Ser Glu Gln Glu Leu Thr Ala Ile Val Arg Asp Leu Gly
 1               5                  10                  15

Cys Gly Pro Tyr Phe Leu Gly Thr Phe Asp Lys Arg Phe Pro Gly Phe
                 20                  25                  30

Val Ser Arg Asp Arg Leu Ser Cys Ala Ile Val Asn Thr Ala Gly Arg
         35                  40                  45

Glu Thr Gly Gly Val His Trp Leu Ala Phe Gly Trp Asn Pro Lys Ser
 50                  55                  60

His Thr Cys Tyr Leu Phe Asp Pro Phe Gly Phe Ser Asp Gln Arg Leu
 65                  70                  75                  80

Lys Gln Ile Tyr Gln Phe Glu Tyr Glu Ser Leu Leu Arg Arg Ser Ala
```

```
                    85                  90                   95
Leu Ala Ala Thr Lys Asp Arg Cys Val Thr Leu Glu Lys Ser Thr Gln
                100                 105                 110

Thr Val Gln Gly Pro Phe Ser Ala Ala Cys Gly Leu Phe Cys Cys Met
            115                 120                 125

Phe Leu His Ala Phe Thr His Trp Pro Asp His Pro Met Asp Lys Asn
        130                 135                 140

Pro Thr Met Asp Leu Leu Thr Gly Val Pro Asn Cys Met Leu Gln Ser
145                 150                 155                 160

Pro Gln Val Val Gly Thr Leu Gln Arg Asn Gln Asn Glu Leu Tyr Lys
                165                 170                 175

Phe Leu Asn Ser Leu Ser Pro Tyr Phe Arg His Asn Arg Glu Arg Ile
            180                 185                 190

Glu Lys Ala Thr Ser Phe Thr Lys Met Gln Asn Gly Leu Lys
        195                 200                 205
```

(2) INFORMATION FOR SEQ ID NO:7:

(i) SEQUENCE CHARACTERISTICS:
        (A) LENGTH: 30 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:7:

```
Ala Ser Met Thr Gly Gly Gln Gln Met Gly Arg Asp Pro Ala Ala Ala
1               5                   10                  15

Met Gly Ser Ser Glu Gln Glu Leu Lys Ala Ile Val Lys Asp
            20                  25                  30
```

(2) INFORMATION FOR SEQ ID NO:8:

(i) SEQUENCE CHARACTERISTICS:
        (A) LENGTH: 34 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:8:

```
Met Arg Ala Lys Leu Leu Gly Ile Val Leu Thr Thr Pro Ile Ala Ile
1               5                   10                  15

Ser Ser Phe Ala Ser Thr Asp Pro Ala Ala Ala Met Gly Ser Ser Glu
            20                  25                  30

Gln Glu
```

(2) INFORMATION FOR SEQ ID NO:9:

(i) SEQUENCE CHARACTERISTICS:
        (A) LENGTH: 34 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:9:

```
Ser Thr Asp Pro Ala Ala Ala Met Gly Ser Ser Glu Gln Glu Leu Lys
1               5                   10                  15

Ala Ile Val Lys Asp Leu Gly Cys Gly Pro Tyr Phe Leu Gly Thr Tyr
```

```
                    20                  25                  30
Asp Lys (2) INFORMATION FOR SEQ ID NO:10:

(i) SEQUENCE CHARACTERISTICS:
        (A) LENGTH: 30 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:10:

Met Arg Ala Lys Leu Leu Gly Ile Val Leu Thr Thr Pro Ile Ala Ile
1               5                  10                  15

Ser Ser Phe Ala Ser Thr His Met Gly Ser Ser Glu Gln Glu
            20                  25                  30

(2) INFORMATION FOR SEQ ID NO:11:

(i) SEQUENCE CHARACTERISTICS:
        (A) LENGTH: 33 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:11:

Ser Thr His Met Gly Ser Ser Glu Gln Glu Leu Lys Ala Ile Val Lys
1               5                  10                  15

Asp Leu Gly Cys Gly Pro Tyr Phe Leu Gly Thr Tyr Asp Lys Arg Phe
            20                  25                  30

Pro (2) INFORMATION FOR SEQ ID NO:12:

(i) SEQUENCE CHARACTERISTICS:
        (A) LENGTH: 33 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:12:

Gly Ser Ser Asp Leu Gly Cys Gly Pro Tyr Phe Leu Gly Thr Tyr Asp
1               5                  10                  15

Lys Arg Phe Pro Gly Phe Val Ser Pro His Lys Leu Ala Cys Ala Ile
            20                  25                  30

Val (2) INFORMATION FOR SEQ ID NO:13:

(i) SEQUENCE CHARACTERISTICS:
        (A) LENGTH: 29 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:13:

Met Arg Ala Lys Leu Leu Gly Ile Val Leu Thr Thr Pro Ile Ala Ile
1               5                  10                  15
```

Ser Ser Phe Ala Ser Thr His Met Gly Ser Glu Gln Glu
            20                  25

(2) INFORMATION FOR SEQ ID NO:14:

(i) SEQUENCE CHARACTERISTICS:
        (A) LENGTH: 33 amino acids
        (B) TYPE: amino acid
        (C) STRANDEDNESS:
        (D) TOPOLOGY: linear (v) FRAGMENT TYPE: N-terminal (xi) SEQUENCE DESCRIPTION: SEQ ID NO:14:

Ser Thr His Met Gly Ser Ser Glu Gln Glu Leu Lys Ala Ile Val Lys
1               5                   10                  15

Asp Leu Gly Cys Gly Pro Tyr Phe Leu Gly Thr Tyr Asp Lys Arg Phe
            20                  25                  30

Pro (2) INFORMATION FOR SEQ ID NO:15:

(i) SEQUENCE CHARACTERISTICS:
        (A) LENGTH: 250 amino acids
        (B) TYPE: amino acid
        (C) STRANDEDNESS:
        (D) TOPOLOGY: linear (xi) SEQUENCE DESCRIPTION: SEQ ID NO:15:

Met Glu Asp Ile Asn Phe Ala Ser Leu Ala Pro Arg His Gly Ser Arg
1               5                   10                  15

Pro Phe Met Gly Asn Trp Gln Asp Ile Gly Thr Ser Asn Met Ser Gly
            20                  25                  30

Gly Ala Phe Ser Trp Gly Ser Leu Trp Ser Gly Ile Lys Asn Phe Gly
            35                  40                  45

Ser Thr Ile Lys Asn Tyr Gly Ser Lys Ala Trp Asn Ser Ser Thr Gly
50                  55                  60

Gln Met Leu Arg Asp Lys Leu Lys Glu Gln Asn Phe Gln Gln Lys Val
65                  70                  75                  80

Val Asp Gly Leu Ala Ser Gly Ile Ser Gly Val Val Asp Leu Ala Asn
            85                  90                  95

Gln Ala Val Gln Asn Lys Ile Asn Ser Lys Leu Asp Pro Arg Pro Pro
            100                 105                 110

Val Glu Glu Pro Pro Pro Ala Val Glu Thr Val Ser Pro Glu Gly Arg
            115                 120                 125

Gly Glu Lys Arg Pro Arg Pro Asp Arg Glu Glu Thr Leu Val Thr Gln
            130                 135                 140

Ile Asp Glu Pro Pro Ser Tyr Glu Glu Ala Leu Lys Gln Gly Leu Pro
145                 150                 155                 160

Thr Thr Arg Pro Ile Ala Pro Met Ala Thr Gly Val Leu Gly Gln His
            165                 170                 175

Thr Pro Val Thr Leu Asp Leu Pro Pro Ala Asp Thr Gln Gln Lys
            180                 185                 190

Pro Val Leu Pro Gly Pro Ser Ala Val Val Thr Arg Pro Ser Arg
            195                 200                 205

Ala Ser Leu Arg Arg Ala Ala Ser Gly Pro Arg Ser Met Arg Pro Val
            210                 215                 220

Ala Ser Gly Asn Trp Gln Ser Thr Leu Asn Ser Ile Val Gly Leu Gly
225                 230                 235                 240

Val Gln Ser Leu Lys Arg Arg Arg Cys Phe
                245                 250

(2) INFORMATION FOR SEQ ID NO:16:

(i) SEQUENCE CHARACTERISTICS:
        (A) LENGTH: 214 amino acids
        (B) TYPE: amino acid
        (C) STRANDEDNESS:
        (D) TOPOLOGY: linear (xi) SEQUENCE DESCRIPTION: SEQ ID NO:16:

Met Gly Ser Ser Glu Gln Glu Leu Val Ala Ile Ala Arg Asp Leu Gly
1               5                   10                  15

Cys Gly Ser Tyr Phe Leu Gly Thr Phe Asp Lys Arg Phe Pro Gly Phe
                20                  25                  30

Met Ala Pro Asn Lys Leu Ala Cys Ala Ile Val Asn Thr Ala Gly Arg
            35                  40                  45

Glu Thr Gly Gly Val His Trp Leu Ala Leu Ala Trp Asn Pro Lys Ser
        50                  55                  60

His Thr Cys Tyr Leu Phe Asp Pro Phe Gly Phe Ser Asp Glu Arg Leu
65                  70                  75                  80

Lys Gln Ile Tyr Gln Phe Glu Tyr Glu Gly Leu Leu Lys Arg Ser Ala
                85                  90                  95

Leu Ala Ser Thr Pro Asp His Cys Ile Thr Leu Val Lys Ser Thr Gln
                100                 105                 110

Thr Val Gln Gly Pro Phe Ser Ala Ala Cys Gly Leu Phe Cys Cys Met
            115                 120                 125

Phe Leu His Ala Phe Ile His Trp Pro Ser Asn Pro Met Glu Gln Asn
130                 135                 140

Pro Thr Met Asp Leu Leu Thr Gly Val Pro Asn Ser Met Leu Gln Ser
145                 150                 155                 160

Pro Gln Val Glu Pro Thr Leu Arg Arg Asn Gln Glu Arg Leu Tyr Arg
                165                 170                 175

Phe Leu Thr Gln His Ser Pro Tyr Phe Arg Arg His Arg Glu Arg Ile
                180                 185                 190

Glu Lys Ala Thr Ala Phe Asp Gln Met Lys Asn Ala Gln Val Leu Phe
            195                 200                 205

His Asn Lys Ile Phe Tyr
        210

(2) INFORMATION FOR SEQ ID NO:17:

(i) SEQUENCE CHARACTERISTICS:
        (A) LENGTH: 205 amino acids
        (B) TYPE: amino acid
        (C) STRANDEDNESS:
        (D) TOPOLOGY: linear (xi) SEQUENCE DESCRIPTION: SEQ ID NO:17:

Met Gly Ser Ser Glu Gln Glu Leu Val Ala Ile Val Arg Glu Leu Gly
1               5                   10                  15

Cys Gly Pro Tyr Phe Leu Gly Thr Phe Asp Lys Arg Phe Pro Gly Phe
                20                  25                  30

Met Ala Pro His Lys Leu Ala Cys Ala Ile Val Asn Thr Ala Gly Arg
            35                  40                  45

Glu Thr Gly Gly Val His Trp Leu Ala Leu Ala Trp Asn Pro Lys Asn
        50                  55                  60

```
Arg Thr Cys Tyr Leu Phe Asp Pro Phe Gly Phe Ser Asp Glu Arg Leu
 65                  70                  75                  80

Lys Gln Ile Tyr Gln Phe Glu Tyr Glu Gly Leu Leu Lys Arg Ser Ala
                 85                  90                  95

Leu Ala Ser Thr Pro Asp His Cys Ile Thr Leu Ile Lys Ser Thr Gln
            100                 105                 110

Thr Val Gln Gly Pro Phe Ser Ala Ala Cys Gly Leu Phe Cys Cys Met
        115                 120                 125

Phe Leu His Ala Phe Val Asn Trp Pro Thr Ser Pro Met Glu Arg Asn
    130                 135                 140

Pro Thr Met Asp Leu Leu Thr Gly Val Pro Asn Ser Met Leu Gln Ser
145                 150                 155                 160

Pro Gln Val Val Pro Thr Leu Arg His Asn Gln Glu Arg Leu Tyr Arg
                165                 170                 175

Phe Leu Ala Gln Arg Ser Pro Tyr Phe Gln Arg His Cys Glu Arg Ile
            180                 185                 190

Lys Lys Ala Thr Ala Phe Asp Gln Met Lys Asn Asn Met
        195                 200                 205
```

(2) INFORMATION FOR SEQ ID NO:18:

(i) SEQUENCE CHARACTERISTICS:
        (A) LENGTH: 209 amino acids
        (B) TYPE: amino acid
        (C) STRANDEDNESS:
        (D) TOPOLOGY: linear (xi) SEQUENCE DESCRIPTION: SEQ ID NO:18:

```
Met Thr Cys Gly Ser Gly Asn Gly Ser Ser Glu Gln Glu Leu Lys Ala
  1               5                  10                  15

Ile Val Arg Asp Leu Gly Cys Gly Pro Tyr Phe Leu Gly Thr Phe Asp
             20                  25                  30

Lys Arg Phe Pro Gly Phe Met Ala Pro Asp Lys Leu Ala Cys Ala Ile
         35                  40                  45

Val Asn Thr Ala Gly Arg Glu Thr Gly Gly Glu His Trp Leu Ala Phe
 50                  55                  60

Gly Trp Asn Pro Arg Tyr Asn Thr Cys Tyr Leu Phe Asp Pro Phe Gly
 65                  70                  75                  80

Phe Ser Asp Glu Arg Leu Lys Gln Ile Tyr Gln Phe Glu Tyr Glu Gly
                 85                  90                  95

Leu Leu Arg Arg Ser Ala Leu Ala Thr Lys Asp Arg Cys Ile Thr Leu
            100                 105                 110

Glu Lys Ser Thr Gln Ser Val Gln Gly Pro Arg Ser Ala Ala Cys Gly
        115                 120                 125

Leu Phe Cys Cys Met Phe Leu His Ala Phe Val His Trp Pro Asp Arg
    130                 135                 140

Pro Met Asp Gly Asn Pro Thr Met Lys Leu Val Thr Gly Val Ser Asn
145                 150                 155                 160

Ser Met Leu Gln Ser Pro Gln Val Gln Pro Thr Leu Arg Arg Asn Gln
                165                 170                 175

Glu Val Leu Tyr Arg Phe Leu Asn Thr His Ser Ser Tyr Phe Arg Ser
            180                 185                 190

His Arg Ala Arg Ile Glu Arg Ala Thr Ala Phe Asp Arg Met Asp Met
        195                 200                 205

Gln
```

(2) INFORMATION FOR SEQ ID NO:19:

(i) SEQUENCE CHARACTERISTICS:
        (A) LENGTH: 201 amino acids
        (B) TYPE: amino acid
        (C) STRANDEDNESS:
        (D) TOPOLOGY: linear (xi) SEQUENCE DESCRIPTION: SEQ ID NO:19:

```
Met Ala Ala Gly Ser Gly Glu Gln Glu Leu Arg Ala Ile Ile Arg Asp
 1               5                  10                  15

Leu Gly Cys Gly Pro Tyr Phe Leu Gly Thr Phe Asp Lys Arg Phe Pro
                20                  25                  30

Gly Phe Met Ala Pro His Lys Val Ala Cys Ala Ile Val Asn Thr Ala
             35                  40                  45

Gly Arg Glu Thr Gly Gly Glu His Trp Leu Ala Phe Ala Trp Asn Pro
         50                  55                  60

Arg Ser Asn Thr Cys Tyr Leu Phe Asp Pro Phe Gly Phe Ser Asp Gln
 65                  70                  75                  80

Arg Leu Lys Gln Ile Tyr Gln Phe Glu Tyr Glu Gly Leu Leu Arg Arg
                 85                  90                  95

Ser Ala Leu Ala Thr Lys Asp Arg Cys Val Thr Trp Lys Ser His Gln
            100                 105                 110

Thr Cys Arg Val Arg Val Gly Arg Cys Gly Phe Ser Ala Ala Cys Ser
            115                 120                 125

Thr Ala Cys Ala Trp Pro Thr Pro Met Asp Lys Asn Pro Thr Met Asn
        130                 135                 140

Leu Leu Thr Gly Val Pro Asn Gly Met Leu Gln Ser Pro Gln Val Glu
145                 150                 155                 160

Pro Thr Leu Arg Arg Asn Gln Glu Ala Leu Tyr Arg Phe Leu Asn Ser
                165                 170                 175

His Ser Ala Tyr Phe Arg Ser His Arg Ala Arg Ile Glu Lys Ala Thr
            180                 185                 190

Ala Phe Asp Arg Met Asn Gln Asp Met
            195                 200
```

(2) INFORMATION FOR SEQ ID NO:20:

(i) SEQUENCE CHARACTERISTICS:
        (A) LENGTH: 204 amino acids
        (B) TYPE: amino acid
        (C) STRANDEDNESS:
        (D) TOPOLOGY: linear (xi) SEQUENCE DESCRIPTION: SEQ ID NO:20:

```
Met Gly Ser Arg Glu Glu Glu Leu Arg Phe Ile Leu His Asp Leu Gly
 1               5                  10                  15

Val Gly Pro Tyr Phe Leu Gly Thr Phe Asp Lys His Phe Pro Gly Phe
                20                  25                  30

Ile Ser Lys Asp Arg Met Ser Cys Ala Ile Val Asn Thr Ala Gly Arg
             35                  40                  45

Glu Thr Gly Gly Val His Trp Leu Ala Met Ala Trp His Pro Ala Ser
         50                  55                  60

Gln Thr Phe Tyr Met Phe Asp Pro Phe Gly Phe Ser Asp Gln Lys Leu
 65                  70                  75                  80

Lys Gln Ile Tyr Asn Phe Glu Tyr Gln Gly Leu Leu Lys Arg Ser Ala
                 85                  90                  95

Leu Thr Ser Thr Ala Asp Arg Cys Leu Thr Leu Ile Gln Ser Thr Gln
            100                 105                 110
```

Ser Val Gln Gly Pro Asn Ser Ala Ala Cys Gly Leu Phe Cys Cys Met
            115                 120                 125

Phe Leu His Ala Phe Val Arg Trp Pro Leu Arg Ala Met Asp Asn Asn
        130                 135                 140

Pro Thr Met Asn Leu Ile His Gly Val Pro Asn Asn Met Leu Glu Ser
145                 150                 155                 160

Pro Ser Ser Gln Asn Val Phe Leu Arg Asn Gln Gln Asn Leu Tyr Arg
                165                 170                 175

Phe Leu Arg Arg His Ser Pro His Phe Val Lys His Ala Ala Gln Ile
        180                 185                 190

Glu Ala Asp Thr Ala Phe Asp Lys Met Leu Thr Asn
        195                 200

(2) INFORMATION FOR SEQ ID NO:21:

(i) SEQUENCE CHARACTERISTICS:
        (A) LENGTH: 202 amino acids
        (B) TYPE: amino acid
        (C) STRANDEDNESS:
        (D) TOPOLOGY: linear (xi) SEQUENCE DESCRIPTION: SEQ ID NO:21:

Met Ser Gly Leu Ser Glu Lys Glu Val Phe Leu Leu Ser Ser Leu
1               5                   10                  15

Gln Cys Thr His Gly Phe Leu Gly Thr Phe Asp Cys Arg Phe Pro Gly
            20                  25                  30

Phe Ile Asn Lys Val Lys Val Gln Thr Ala Ile Ile Asn Thr Gly Pro
        35                  40                  45

Arg Glu Gln Gly Gly Ile His Trp Ile Ala Leu Ala Trp Asp Pro Lys
    50                  55                  60

Ser Tyr Gln Met Phe Ile Phe Asp Pro Leu Gly Trp Lys Asn Asp Gln
65                  70                  75                  80

Leu Met Lys Tyr Tyr Lys Phe Ser Tyr Ser Asn Leu Ile Lys Arg Ser
                85                  90                  95

Ala Leu Ser Ser Pro Asp Lys Cys Val Lys Val Ile Lys Asn Ser Gln
            100                 105                 110

Ser Val Gln Cys Thr Cys Ala Gly Ser Cys Gly Leu Phe Cys Val Phe
        115                 120                 125

Phe Leu Tyr Cys Phe Tyr Lys Tyr Lys Ser Asn Ala Phe Lys Asn Cys
130                 135                 140

Leu Phe Gln Ser Leu Tyr Gly Ser Ile Pro Ser Leu Thr Pro Pro Asn
145                 150                 155                 160

Pro Thr Asn Leu His Lys Asn Gln Asp Phe Leu Tyr Lys Phe Phe Lys
                165                 170                 175

Glu Lys Ser Leu Tyr Phe Arg Gln Asn Glu Glu Tyr Ile Val Ser Asn
            180                 185                 190

Thr Lys Ile Gly Leu Ile Lys Ser His Ile
            195                 200

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:22:

```
CCCGTCGACC CATATGGGCT CCAG                                                    24
```

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:23:

```
GGCCCTTTCG TCTTCAAG                                                           18
```

(2) INFORMATION FOR SEQ ID NO:24:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:24:

```
CCCCATATGG GCTCCTCAGA TCTTGGTTGT GGGCC                                        35
```

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:25:

```
TAATACGACT CACTATAGGG AGA                                                     23
```

(2) INFORMATION FOR SEQ ID NO:26:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:26:

```
CTTGGATCCA TTATTTTTAC ATGTTCTTAA GGTGACAA                                     38
```

(2) INFORMATION FOR SEQ ID NO:27:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:27:

```
TTAAGAACAT GGGTCACCAC CACCATCACC ATAACATGTA AAAATAATG                         49
```

(2) INFORMATION FOR SEQ ID NO:28:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:28:

GATCCATTAT TTTTACATGT TATGGTGATG GTGGTGGTGA CCCATGTTC           49

(2) INFORMATION FOR SEQ ID NO:29:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (xi) SEQUENCE DESCRIPTION: SEQ ID NO:29:

CCCGTCGACC CATATGGGTT CAAGC                                    25

(2) INFORMATION FOR SEQ ID NO:30:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (iv) ANTI-SENSE: YES (xi) SEQUENCE DESCRIPTION: SEQ ID NO:30:

CCCAAGCTTG TACTCCAATG                                          20

(2) INFORMATION FOR SEQ ID NO:31:

(i) SEQUENCE CHARACTERISTICS:
           (A) LENGTH: 13 amino acids
           (B) TYPE: amino acid
           (C) STRANDEDNESS:
           (D) TOPOLOGY: linear (v) FRAGMENT TYPE: N-terminal (xi) SEQUENCE DESCRIPTION: SEQ ID NO:31:

Ala Lys Lys Arg Ser Asp Gln His Pro Val Arg Val Arg
1               5                   10

(2) INFORMATION FOR SEQ ID NO:32:

(i) SEQUENCE CHARACTERISTICS:
           (A) LENGTH: 249 amino acids
           (B) TYPE: amino acid
           (C) STRANDEDNESS:
           (D) TOPOLOGY: linear (xi) SEQUENCE DESCRIPTION: SEQ ID NO:32:

Met Ala Ser Met Thr Gly His His His His His His Gly Met Ser Gly
1               5                   10                  15

Gly Met Ala Lys Lys Ile Phe Thr Ser Ala Leu Gly Thr Ala Glu Pro
            20                  25                  30

Tyr Ala Tyr Ile Ala Lys Pro Asp Tyr Gly Asn Glu Glu Arg Gly Phe
        35                  40                  45

Gly Asn Pro Arg Gly Val Tyr Lys Val Asp Leu Thr Ile Pro Asn Lys
    50                  55                  60

Asp Pro Arg Cys Gln Arg Met Val Asp Glu Ile Val Lys Cys His Glu
65                  70                  75                  80

Glu Ala Tyr Ala Ala Ala Val Glu Glu Tyr Glu Ala Asn Pro Pro Ala
                85                  90                  95

Val Ala Arg Gly Lys Lys Pro Leu Lys Pro Tyr Glu Gly Asp Met Pro

```
                100                 105                 110
Phe Phe Asp Asn Gly Asp Gly Thr Thr Thr Phe Lys Phe Lys Cys Tyr
            115                 120                 125
Ala Ser Phe Gln Asp Lys Lys Thr Lys Glu Thr Lys His Ile Asn Leu
130                 135                 140
Val Val Val Asp Ser Lys Gly Lys Lys Met Glu Asp Val Pro Ile Ile
145                 150                 155                 160
Gly Gly Gly Ser Lys Leu Lys Val Lys Tyr Ser Leu Val Pro Tyr Lys
                165                 170                 175
Trp Asn Thr Ala Val Gly Ala Ser Val Lys Leu Gln Leu Glu Ser Val
            180                 185                 190
Met Leu Val Glu Leu Ala Thr Phe Gly Gly Gly Glu Asp Asp Trp Ala
            195                 200                 205
Asp Glu Val Glu Glu Asn Gly Tyr Val Ala Ser Gly Ser Ala Lys Ala
210                 215                 220
Ser Lys Pro Arg Asp Glu Ser Trp Asp Glu Asp Glu Glu Ser
225                 230                 235                 240
Glu Glu Ala Asp Glu Asp Gly Asp Phe
                245
```

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:33:

TTTTGCTAGC ATGGGCTCCA GTG      23

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:34:

GGCCCTTTCG TCTTCAAG      18

(2) INFORMATION FOR SEQ ID NO:35:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:35:

CCTACATATG GCTTCTATGA CTGGTCACCA CCACCA      36

(2) INFORMATION FOR SEQ ID NO:36:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO:36:

CCCGGTCACC ACCACCATCA CCATGGTATG AGCGGCGGCA TGGCTAAGAA GAT      53

(2) INFORMATION FOR SEQ ID NO:37:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

```
Met Ala Ser Met Thr Gly His His His His His His Gly Met Ser Gly
1               5                   10                  15

Gly
```

(2) INFORMATION FOR SEQ ID NO:38:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

```
Met Ser Gly Gly
1
```

(2) INFORMATION FOR SEQ ID NO:39:

(i) SEQUENCE CHARACTERISTICS:
        (A) LENGTH: 1158 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 21..236
        (D) OTHER INFORMATION: /product= "Ad12 pMu and pVI"

(ix) FEATURE:
        (A) NAME/KEY: CDS
        (B) LOCATION: 296..1090
        (D) OTHER INFORMATION: /product= "Ad12 pMu and pVI"

(xi) SEQUENCE DESCRIPTION: SEQ ID NO:39:

```
CTGCGCTGCC GTTTTTTCAG ATG GCT CTT ACT TGC CGA ATG CGC ATA CCC          50
                      Met Ala Leu Thr Cys Arg Met Arg Ile Pro
                       1               5                  10

ATT CCA GGA TAC AGA GGA CGA CCC CGC CGG AGG AAA GGG CTG ACC GGG         98
Ile Pro Gly Tyr Arg Gly Arg Pro Arg Arg Arg Lys Gly Leu Thr Gly
               15                  20                  25

AAC GGT CGA TTT CGG CGG CGT AGT ATG CGC AGA CGC ATG AAG GGT GGG        146
Asn Gly Arg Phe Arg Arg Arg Ser Met Arg Arg Arg Met Lys Gly Gly
                30                  35                  40

GTG CTG CCC TTC CTA ATT CCA CTT ATT GCT GCG GCC ATT GGA GCC GTT        194
Val Leu Pro Phe Leu Ile Pro Leu Ile Ala Ala Ala Ile Gly Ala Val
             45                  50                  55

CCC GGA ATT GCC TCA GTA GCC TTG CAG GCT TCT CGA AAA AAT                236
Pro Gly Ile Ala Ser Val Ala Leu Gln Ala Ser Arg Lys Asn
         60                  65                  70

TAAAATAAAA TAAACTTCC AACTTATTAC TGGTACTATG ACTGTTTTAT GCAGACTAA         295
```

```
ATG GAA GAC ATC AAT TTT TCG TCG CTG GCC CCG CGA CAC GGC ACG CGG      343
Met Glu Asp Ile Asn Phe Ser Ser Leu Ala Pro Arg His Gly Thr Arg
 1               5                  10                  15

CCG TAC ATG GGC ACC TGG AAC GAG ATC GGC ACG AGC CAG CTG AAC GGG      391
Pro Tyr Met Gly Thr Trp Asn Glu Ile Gly Thr Ser Gln Leu Asn Gly
             20                  25                  30

GGC GCC TTC AAT TGG AAC AGT ATC TGG AGC GGT CTT AAA AAT TTT GGT      439
Gly Ala Phe Asn Trp Asn Ser Ile Trp Ser Gly Leu Lys Asn Phe Gly
                 35                  40                  45

TCC ACG ATT AAG ACA TAT GGC ACC AAG GCG TGG AAC AGC CAA ACC GGC      487
Ser Thr Ile Lys Thr Tyr Gly Thr Lys Ala Trp Asn Ser Gln Thr Gly
         50                  55                  60

CAG ATG CTA AGG GAC AAG TTA AAA GAC CAA AAT TTT CAA CAG AAA GTT      535
Gln Met Leu Arg Asp Lys Leu Lys Asp Gln Asn Phe Gln Gln Lys Val
 65                  70                  75                  80

GTA GAT GGT CTG GCT TCG GGA ATT AAT GGA GTT GTA GAC ATA GCC AAT      583
Val Asp Gly Leu Ala Ser Gly Ile Asn Gly Val Val Asp Ile Ala Asn
                 85                  90                  95

CAG GCT GTA CAG AAA AAA ATT GCC AAC CGT TTA GAG CCG CGG CCC GAC      631
Gln Ala Val Gln Lys Lys Ile Ala Asn Arg Leu Glu Pro Arg Pro Asp
             100                 105                 110

GAG GTA ATG GTA GAG GAA AAG CTG CCA CCT CTA GAA ACT GTG CCC GGA      679
Glu Val Met Val Glu Glu Lys Leu Pro Pro Leu Glu Thr Val Pro Gly
         115                 120                 125

TCC GTT CCA ACC AAA GGA GAA AAG CGG CCA CGG CCG GAT GCA GAG GAA      727
Ser Val Pro Thr Lys Gly Glu Lys Arg Pro Arg Pro Asp Ala Glu Glu
130                 135                 140

ACC TTA GTA ACG CAC ACA ACA GAA CCG CCG TCC TAT GAG GAA GCA ATA      775
Thr Leu Val Thr His Thr Thr Glu Pro Pro Ser Tyr Glu Glu Ala Ile
145                 150                 155                 160

AAA CAA GGA GCC GCT CTG TCA CCT ACC ACC TAT CCC ATG ACC AAG CCT      823
Lys Gln Gly Ala Ala Leu Ser Pro Thr Thr Tyr Pro Met Thr Lys Pro
                 165                 170                 175

ATT TTA CCC ATG GCT ACT AGA GTG TAT GGA AAA AAC GAA AAT GTG CCT      871
Ile Leu Pro Met Ala Thr Arg Val Tyr Gly Lys Asn Glu Asn Val Pro
             180                 185                 190

ATG ACC CTT GAG CTG CCT CCT TTG CCA GAA CCC ACT ATC GCG GAT CCC      919
Met Thr Leu Glu Leu Pro Pro Leu Pro Glu Pro Thr Ile Ala Asp Pro
         195                 200                 205

GTA GGT TCC GTT CCT GTT GCA TCT GTT CCA GTT GCA TCG ACA GTG AGC      967
Val Gly Ser Val Pro Val Ala Ser Val Pro Val Ala Ser Thr Val Ser
210                 215                 220

CGT CCA GCA GTG CGG CCT GTT GCC GTG GCT AGC TTG CGA AAC CCA CGA     1015
Arg Pro Ala Val Arg Pro Val Ala Val Ala Ser Leu Arg Asn Pro Arg
225                 230                 235                 240

TCC AGT AAT TGG CAA AGT ACC CTA AAC AGT ATT GTG GGA CTG GGA GTA     1063
Ser Ser Asn Trp Gln Ser Thr Leu Asn Ser Ile Val Gly Leu Gly Val
                 245                 250                 255

AAG TCT CTC AAA CGC CGA CGC TGC TAC TAACATTAAA AGACGAGTGT           1110
Lys Ser Leu Lys Arg Arg Arg Cys Tyr
             260                 265

TAATTCCCAT CTGTGTATAC GCCTCCTATG TTAGCGCCAG AGGACCAA                1158
```

(2) INFORMATION FOR SEQ ID NO:40:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:40:

Met Ala Leu Thr Cys Arg Met Arg Ile Pro Ile Pro Gly Tyr Arg Gly
1               5                   10                  15

Arg Pro Arg Arg Arg Lys Gly Leu Thr Gly Asn Gly Arg Phe Arg Arg
                20                  25                  30

Arg Ser Met Arg Arg Arg Met Lys Gly Gly Val Leu Pro Phe Leu Ile
            35                  40                  45

Pro Leu Ile Ala Ala Ala Ile Gly Ala Val Pro Gly Ile Ala Ser Val
        50                  55                  60

Ala Leu Gln Ala Ser Arg Lys Asn
65                  70

(2) INFORMATION FOR SEQ ID NO:41:

(i) SEQUENCE CHARACTERISTICS:
       (A) LENGTH: 265 amino acids
       (B) TYPE: amino acid
       (D) TOPOLOGY: linear (ii) MOLECULE TYPE: protein (xi) SEQUENCE DESCRIPTION: SEQ ID NO:41:

Met Glu Asp Ile Asn Phe Ser Ser Leu Ala Pro Arg His Gly Thr Arg
1               5                   10                  15

Pro Tyr Met Gly Thr Trp Asn Glu Ile Gly Thr Ser Gln Leu Asn Gly
                20                  25                  30

Gly Ala Phe Asn Trp Asn Ser Ile Trp Ser Gly Leu Lys Asn Phe Gly
            35                  40                  45

Ser Thr Ile Lys Thr Tyr Gly Thr Lys Ala Trp Asn Ser Gln Thr Gly
        50                  55                  60

Gln Met Leu Arg Asp Lys Leu Lys Asp Gln Asn Phe Gln Gln Lys Val
65                  70                  75                  80

Val Asp Gly Leu Ala Ser Gly Ile Asn Gly Val Val Asp Ile Ala Asn
                85                  90                  95

Gln Ala Val Gln Lys Lys Ile Ala Asn Arg Leu Glu Pro Arg Pro Asp
            100                 105                 110

Glu Val Met Val Glu Glu Lys Leu Pro Pro Leu Glu Thr Val Pro Gly
        115                 120                 125

Ser Val Pro Thr Lys Gly Glu Lys Arg Pro Arg Pro Asp Ala Glu Glu
130                 135                 140

Thr Leu Val Thr His Thr Thr Glu Pro Pro Ser Tyr Glu Glu Ala Ile
145                 150                 155                 160

Lys Gln Gly Ala Ala Leu Ser Pro Thr Thr Tyr Pro Met Thr Lys Pro
                165                 170                 175

Ile Leu Pro Met Ala Thr Arg Val Tyr Gly Lys Asn Glu Asn Val Pro
            180                 185                 190

Met Thr Leu Glu Leu Pro Pro Leu Pro Glu Pro Thr Ile Ala Asp Pro
        195                 200                 205

Val Gly Ser Val Pro Val Ala Ser Val Pro Val Ala Ser Thr Val Ser
210                 215                 220

Arg Pro Ala Val Arg Pro Val Ala Val Ala Ser Leu Arg Asn Pro Arg
225                 230                 235                 240

Ser Ser Asn Trp Gln Ser Thr Leu Asn Ser Ile Val Gly Leu Gly Val
                245                 250                 255

Lys Ser Leu Lys Arg Arg Arg Cys Tyr
            260                 265

(2) INFORMATION FOR SEQ ID NO:42:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Gly Val Lys Ser Leu Lys Arg Arg Arg Cys Tyr
1               5                   10
```

(2) INFORMATION FOR SEQ ID NO:43:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Gly Val Gln Ser Leu Lys Arg Arg Arg Cys Phe
1               5                   10
```

(2) INFORMATION FOR SEQ ID NO:44:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "Xaa in position 1 is Leu,
            Ile or Met.  Xaa in positions 2 and 5 is any amino acid."

(xi) SEQUENCE DESCRIPTION: SEQ ID NO:44:

```
Xaa Xaa Gly Gly Xaa
1               5
```

(2) INFORMATION FOR SEQ ID NO:45:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "Xaa in position 1 is Leu,
            Ile or Met.  Xaa in positions 2 and 4 is any amino acid."

(xi) SEQUENCE DESCRIPTION: SEQ ID NO:45:

```
Xaa Xaa Gly Xaa Gly
1               5
```

ACTIVATED RECOMBINANT ADENOVIRUS PROTEINASES

RELATED APPLICATION

This application is a divisional application of U.S. Ser. No. 08/155,171, filed Nov. 19, 1993, now U.S. Pat. No. 5,543,264, which is a continuation-in-part of U.S. Ser. No. 07/851,217, filed Mar. 13, 1992, which is a continuation-in-part of U.S. Ser. No. 07/545,585, now abandoned filed Jun. 29, 1990, now abandoned the disclosures of which are incorporated herein by reference.

GOVERNMENT SUPPORT

Work described herein was supported by Grant No. U01 A126049 from the National Institutes of Health and by the U.S. Department of Energy. The Government has certain rights in the invention.

BACKGROUND OF THE INVENTION

Adenoviruses have a double-stranded, linear DNA genome of about 36 Kb. Adenovirus particles are nonenveloped, icosahedral structures composed of multiple copies of each of twelve virus-encoded proteins and a single copy of the DNA genome. Adenoviruses for many different eukaryotic species have been identified. All adenoviruses have a similar genome organization and virion structure, but adenoviruses from one species do not productively infect the cells of another species. ("The Adenoviruses", Ginsberg, ed., New York: Plenum Press, 1984).

The most extensively studied adenoviruses are the human adenoviruses. At least 46 distinct human adenovirus serotypes have been described. These are classified into six subgroups (A–F) on the basis of related biological and physical properties. The most extensively studied human serotypes are types 2 and 5, which belong to subgroup C. Adenovirus type 2 (Ad2) and type 5 (Ad5) are very closely related; the proteins of Ad2 and Ad5 typically differ at only a few amino acid residues. Adenovirus 12 belongs to subgroup A. Subgroup A adenoviruses differ sufficiently from subgroup C viruses in that corresponding gene products of Ad2 normally will not substitute for the Ad12 product, and vice versa.

All adenovirus genomes are believed to encode closely related proteinases (also called proteases and here, also appropriately called endoproteinases), which cleave several virion precursor polypeptides during virion maturation (Krausslich et al., *Ann. Rev. Biochem.* 7: 701–754 (1988)). The adenovirus endoproteinase (EP) is assembled into virions, with only a few copies in each virion. The adenovirus 2 (Ad2) endoproteinase has been shown to cleave six of the twelve proteins from which virions are assembled. The mature virion components resulting from these six precursors have been designated IIIa, VI, VII (major core protein), VIII, Mu, and TP (terminal protein) (Anderson et al., *Virology* 172: 506–512 (1989)). (The full-length initial products of translation are designated with a p prefix; the C-terminal products of endoproteolytic cleavage are designated by a -c suffix.) Precursor processing occurs primarily, if not exclusively, in young, fully assembled virions (Ishibashi et al., *Virology* 57: 409–424 (1974); Lewis et al., *Cold Spring Harbor Symp. Quant. Biol.* 39: 581–590 (1974)). It has been suggested that the endoproteinase is itself processed autocatalytically (Chatterjee et al., *Proc. Natl. Acad. Sci. USA* 84: 714–718 (1987)).

The 23 kilodalton (kDa) Ad2 EP is encoded by a gene that is expressed at late times after virus infection. The endoproteinase gene is located within the L3 family of adenovirus genes. Evidence that the L3 23 kDa open reading frame encodes an endoproteinase was first provided by analysis of the temperature-sensitive Ad2 mutant, H2ts1 (Weber, *J. Virol.* 17: 462–471 (1976)). The H2ts1 mutation changes proline codon 137 of the L3 23 kDa reading frame to a leucine codon (Yeh-Kai et al., *J. Mol. Biol.* 167: 217–222 (1983)). At the non-permissive temperature, virions produced in H2ts1-infected cells assemble efficiently, but contain precursors in place of the mature components found in wild type particles. Such immature virions attach to cells but fail to yield productive infections (Hannan et al., *Intervirology* 19: 213–223 (1983); Mirza et al., *Intervirology* 13: 307–311 (1980)).

Only a few copies of the adenovirus proteinase are present in each virion. As a consequence of the difficulty of obtaining sufficient quantities of this protein from its natural source, the proteinase polypeptide has not been isolated, its enzymatic activity is not fully characterized, nor is the role of the proteinase in virion maturation well understood.

SUMMARY OF THE INVENTION

This invention relates to activatable adenovirus proteinases which, in combination with two cofactors, are activated adenovirus proteinases. The two cofactors, a polyanion cofactor and a short peptide cofactor, have been shown to be necessary complements of adenovirus proteinase activity. Activated adenovirus proteinases and peptide cofactors of adenovirus proteinase activity are included. The present invention further relates to methods for obtaining and purifying activatable recombinant adenovirus proteinases, activated adenovirus proteinases, and peptide cofactors of adenovirus proteinase activity. Expression constructs suitable for expressing activatable recombinant adenovirus proteinases in host cells are further included. This invention further provides antibodies which react specifically with adenovirus proteinases and not with other adenovirus or mammalian cell proteins. Related methods of use, including methods of interfering with activation of the activatable proteinase, are also the subject of the present invention.

BRIEF DESCRIPTION OF THE DRAWINGS

FIG. 1A is the restriction site map of pT7AD23K5; FIG. 1B is the restriction site map of pT7AD23K8. The approximate positions of the human Ad2 proteinase reading frame, the β-lactamase gene (bla), and the *E. coli* origin of replication (ori), and the direction of transcription from the T7 gene 10 promoter (φ10) are indicated.

FIG. 6 shows the peptide sequence analysis of 23k6. Underlining indicates confirmed sequence.

FIG. 7A is a pET expression plasmid pT1HEP1DBP (also referred to as pT7HIS2) which, upon induction, produces an artificial proteinase substrate called HEP1DBP. FIG. 7B shows the results of fluorescence assays of proteinase activity: (A) wild type Ad2 virus; (B) H2ts1 virus; (C) purified recombinant Ad2 proteinase; and (D) H2ts1 virus with proteinase. The change in fluorescence, ΔF, is the magnitude of the fluorescence from the sample minus the magnitude of the fluorescence from an identical solution without enzyme.

FIG. 12 shows the sequences of the peptide cofactor in peaks a, b, and c and of the precursor to the Ad2 virion component VI (p-VI). The locations of the proteinase recognition sequences and of the peptide cofactor sequence in the p-VI sequence are indicated by underlining and bold print, respectively.

A) Coomassie Blue-stained SDS-polyacrylamide gel:

B) Autoradiogram of the Western blot.

Figure 15:
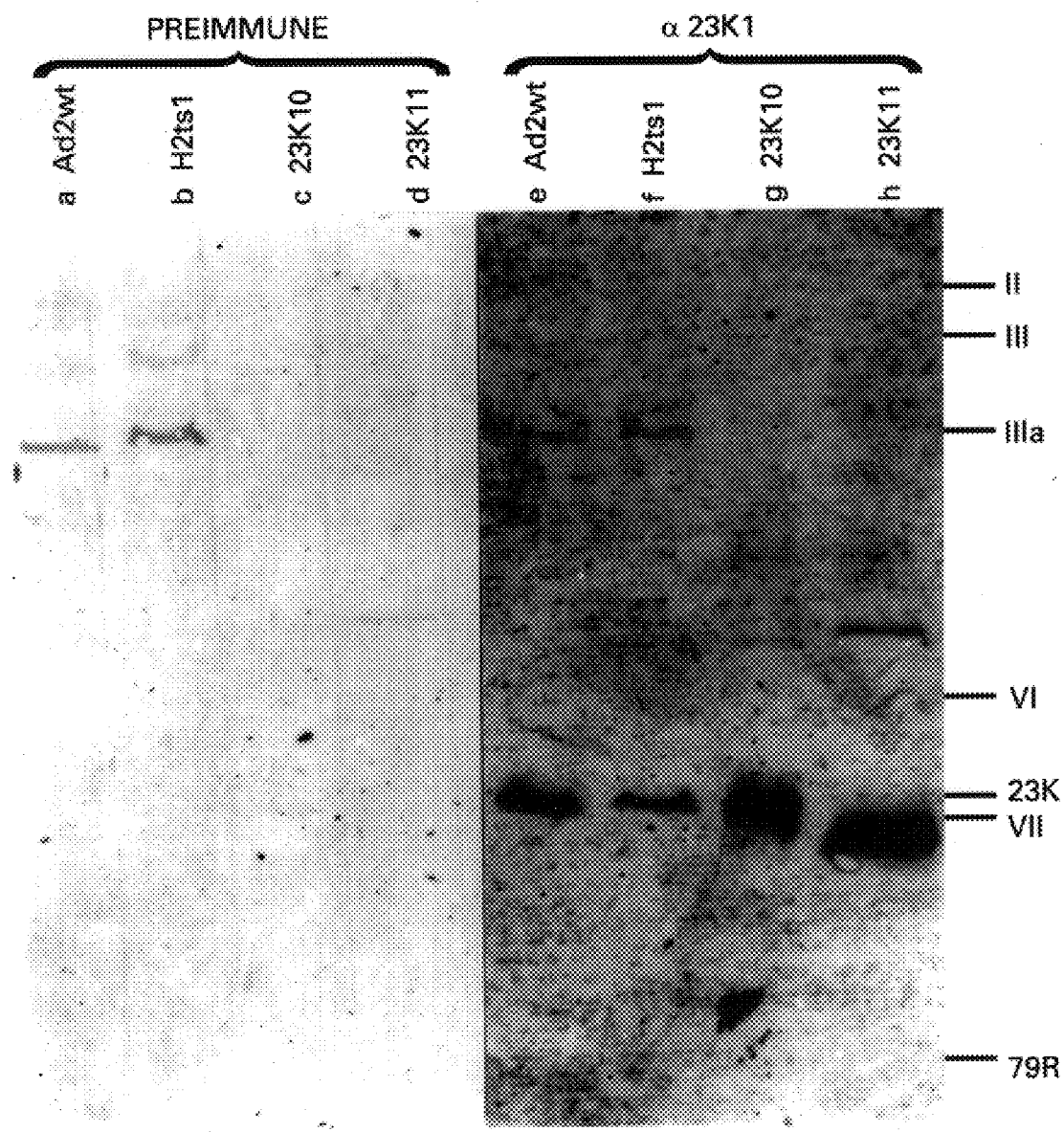

FIG. 15 shows Western blots of virion-derived and recombinant Ad2 proteinases reacted with preimmune and α23K1 sera.

FIGS. 16A and 16B show the predicted amino acid sequences of several adenovirus type proteinases.

Figure 17:
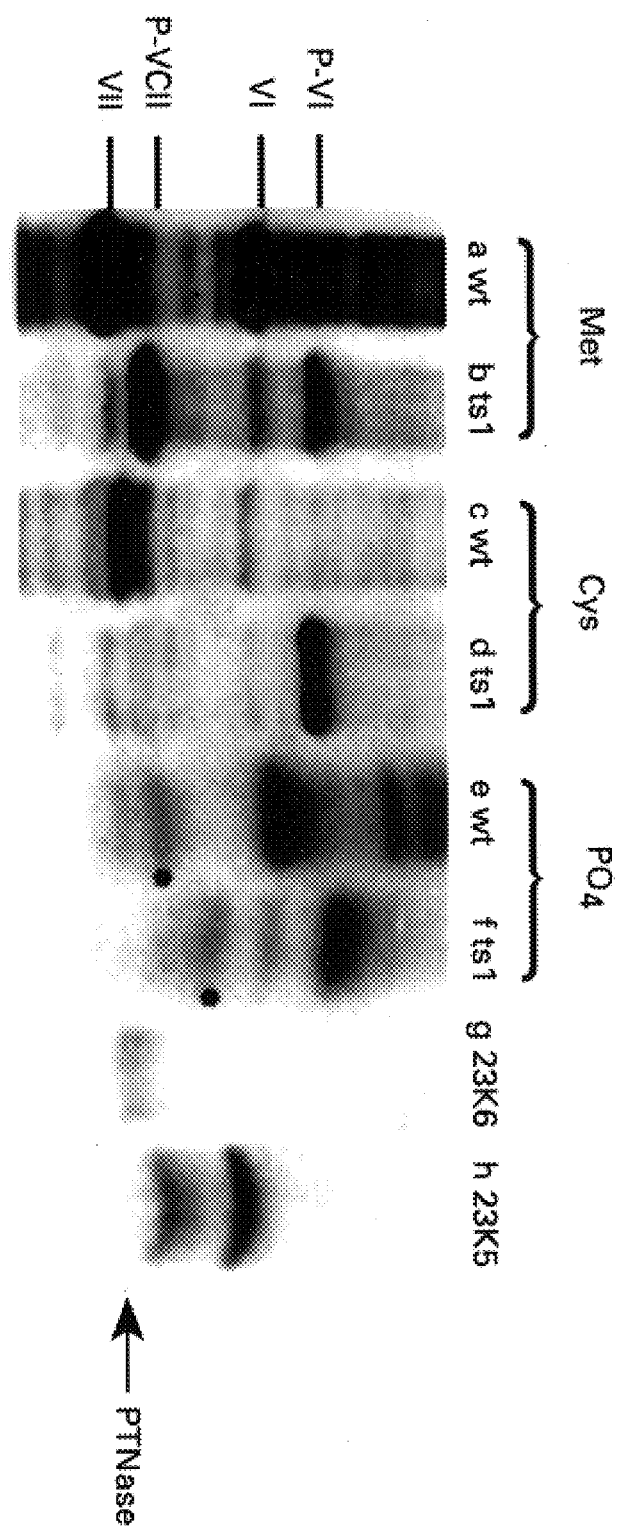

FIG. 17 shows the detection of adenovirus proteinase in radiolabeled virions.

FIG. 18 shows the location of adenovirus proteinase in Ad2 virions.

Figure 19A:
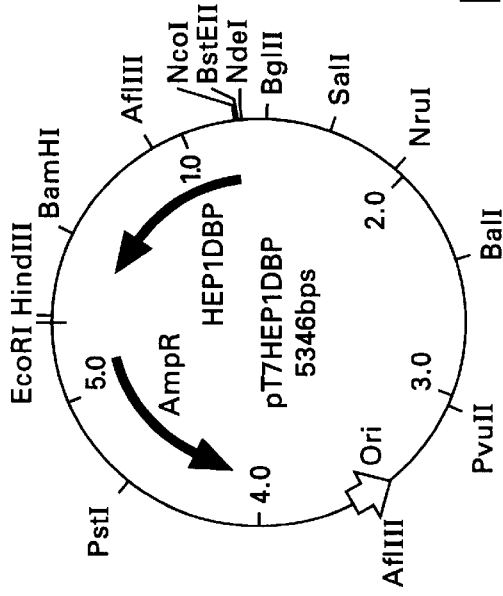
Figure 19B:
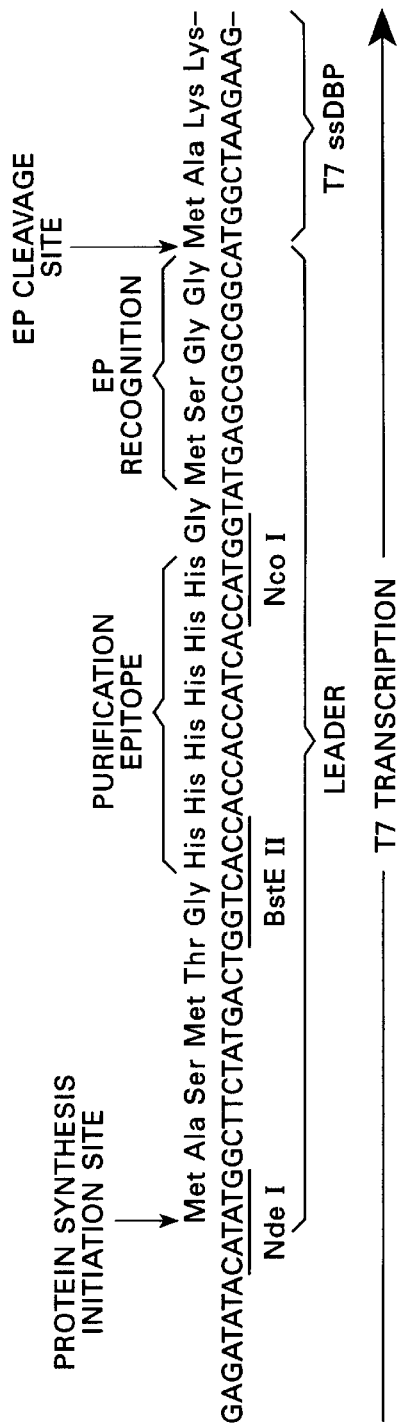

FIG. 19 shows (A) the map of pT1HEP1DBP, an expression vector for an artificial adenovirus substrate and (B) the segment of pT1HEP1DBP encoding the 17-amino acid HEP1DBP leader.

Figure 20A:
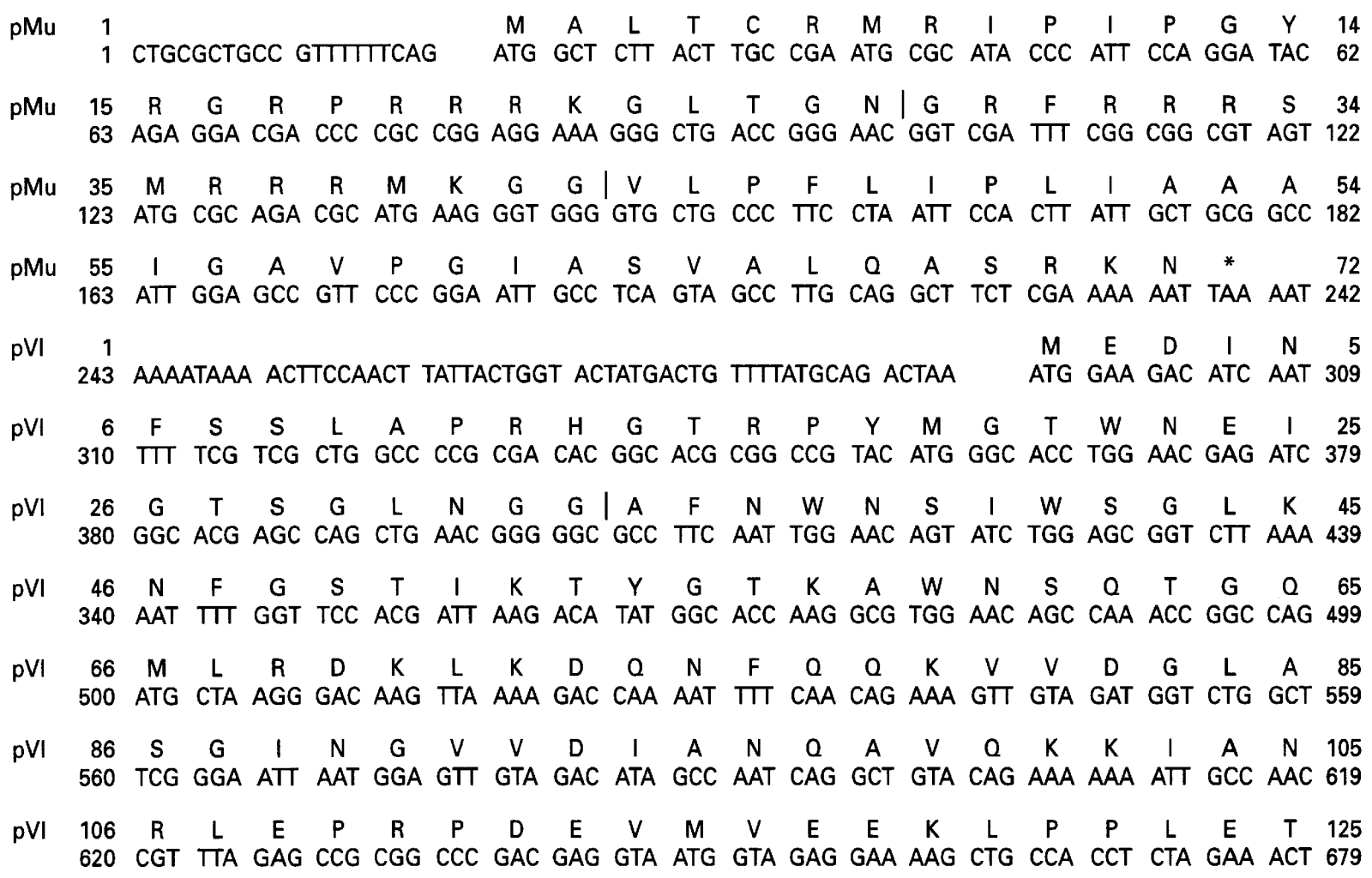

FIG. 20 (2 sheets) shows the nucleotide sequence of the region encoding Ad12 pMu and pVI.

Deposit

A strain of DH-1 containing the plasmid pT7AD23k6 was deposited under the terms of the Budapest Treaty on the International Recognition of the Deposit of Microorganisms for the Purposes of Patent Procedure at the American Type Culture Collection (Rockville, Md., and given the Accession Number on the availability to the public of the deposited material will be irrevocably removed upon the granting of a patent.

DETAILED DESCRIPTION OF THE INVENTION

This invention provides preparations of activated adenovirus proteinases which consist of an activatable recombinant adenovirus proteinase, a DNA cofactor and a peptide cofactor. The peptide cofactor is a short peptide, generally 11 amino acids long, and has an amino acid sequence which is substantially the same as that of the 11 amino acid carboxy-terminus of the precursor to adenovirus virion component VI (p-VI). The polyanion cofactor can consist of any DNA, single-stranded or double-stranded, including genomic, viral, cloned or synthetic oligomeric DNA. RNA, polyglutamic acid, polyaspartic acid and heparin also satisfy the requirement for a polyanion. The activatable adenovirus proteinase can be a recombinant gene product, produced by expression of a construct containing the coding sequence of an adenovirus proteinase inserted into an expression vector which is appropriate for the host cell. As described herein, recombinant adenovirus proteinases expressed in non-mammalian and mammalian host cells fold into activatable proteinases. As also described herein, in the presence of the two mentioned cofactors, the activatable proteinases become activated adenovirus proteinases, which are also the subject of the present invention. The subject invention also includes methods for producing and purifying activatable recombinant adenovirus proteinases from host cells, expression constructs useful for producing activatable adenovirus proteinases, and purified activatable recombinant adenovirus proteinases are provided. This invention further includes antibodies (monoclonal and polyclonal) which recognize adenovirus proteinases antibodies which react specifically with adenovirus proteinases but not with other adenovirus or mammalian cell proteins, and methods of preparing these antibodies. Methods relating to the use of the above materials are also included.

Described below is the production of activatable recombinant adenovirus proteinases in E. coli cells using constructs based on the pET series of bacterial expression vectors (Rosenberg et al., Gene 56: 125–135 (1988)). Production of activatable recombinant proteinase in cultured Sf9 insect (ATCC CRL 1711) cells using a baculovirus vector is also described. As described, activatable recombinant proteinases from two different adenovirus subclasses have been produced (human adenovirus type 2 and type 12) in E. coli. The methods of production and expression constructs used, as well as purification methods, are described. The recombinant proteins produced as described herein have been characterized, and physical and functional characteristics are described. In particular, two cofactors necessary for activation of activatable recombinant adenovirus proteinases have been identified and characterized. Their identification makes it possible to interfere with the activity of adenovirus proteinases, through inhibition of the activity of the cofactors. Preparation and characterization of an anti-proteinase antibody are also described. Uses of the above-mentioned methods and materials are then discussed.

Bacterial Expression Constructs

Several plasmids suitable for expressing recombinant adenovirus type 2 (Ad2) and type 12 (Ad12) proteinases in Bacterial cells were constructed, as summarized in Table 2. As described in Example 2, the plasmids were constructed such that the coding sequences for the adenovirus proteinases were inserted in the expression cassette of a bacterial expression vector, pET-12.

The pET-12 bacterial expression vector is a derivative of the pET-3 expression vector. The pET-3 vector contains an origin of replication (ori) for maintenance of the plasmids in E. coli and the β-lactamase (bla) gene for selection of transformed cells by ampicillin resistance (see e.g., FIG. 1). The pET-3 vector also contains an expression cassette based on transcription from the strong promoter (φ10) of gene 10, which encodes the major capsid protein of bacteriophage T7. The cassette further includes a ribosome binding site or Shine-Dalgarno sequence (AAGGAG; termed SD), the gene 10 translational start site, a transcription terminator, and unique restriction enzyme sites for insertion of foreign genes into the cassette. In the plasmids described below, the adenovirus proteinase reading frames are inserted into the pET expression cassettes such that the proteinase intiation codon is at the correct distance (about 10 bp) from the ribosome recognition site for efficient protein synthesis. In pET vectors, the inserted foreign gene is expressed efficiently only when the T7 RNA polymerase is also expressed in the host cell into which the pET vector is introduced. When protein synthesis is desired, expression plasmids are used to transform an expressing strain, such as BL21(DE3). This strain has the T7 RNA polymerase gene integrated into its bacterial chromosome, under the IPTG-inducible lacUV5 promoter.

Figure 2:
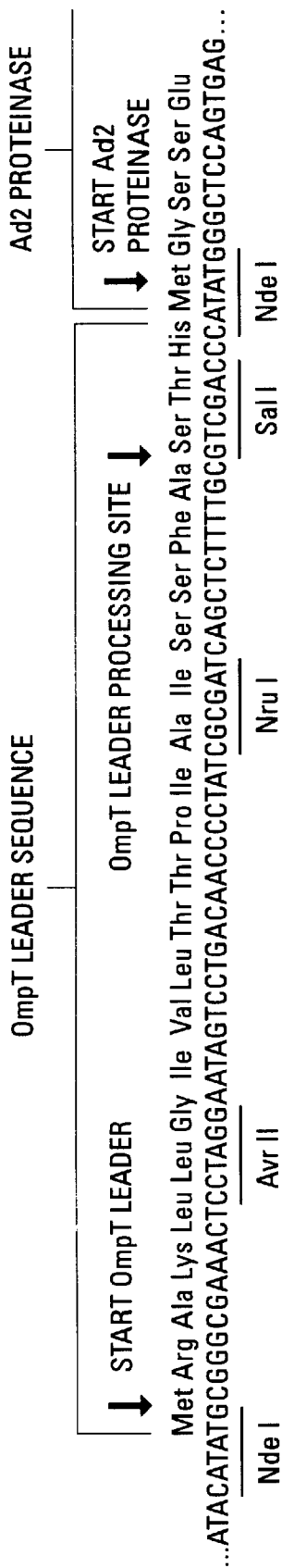
FIG. 2 shows the segment of pT7AD23K5 encoding the junction of the OmpT signal peptide sequence and the human Ad2 proteinase. The signal processing site at the arrow indicates the amino-terminus of the processed 23K5 fusion protein.

The pET-12 expression vector includes, in addition to the expression elements described above, a leader sequence encoding the signal peptide sequence of the E. coli outer membrane protein T (OmpT). The vector was designed to express the product of an inserted foreign gene as an OmpT fusion protein. A fusion protein containing the OmpT signal peptide sequence is expectedto be transported through the E. coli plasma membrane and into the bacterial periplasm. In the process, the OmpT signal peptide is cleaved from the fusion protein by the E. coli signal peptidase. The signal processing site falls between alanine$_{21}$ and serine$_{22}$ of the leader sequence. As a result, cleavage at the signal processing site of OmpT-proteinase fusion proteins, such as the expression products of pT7AD23K5 and pT7AD23k15, leaves three amino acids (Ser-Thr-His) of the signal peptide sequence at the amino-terminus of the proteinase (FIG. 2).

The prototype plasmid for expressing activatable Ad2 proteinase in bacteria is pT7AD23k6. Plasmid pT7AD23k6 contains the 204 codons of the Ad2 proteinase reading frame plus a translational termination codon (TAA). The nucleotide and predicted amino acid sequences of the Ad2 proteinase are shown in the Sequence Listing (SEQ ID NO: 1 and NO: 2).

pT7AD23k6 was derived from the plasmid pT7AD23K5 which encodes an OmpT-Ad2 proteinase fusion protein (FIG. 2). pT7AD23k6 differs from pT7AD23K5 in that it lacks the NdeI fragment containing the OmpT leader sequence (FIG. 2; see SEQ ID NO: 3), and thus, does not encode a protein with a signal peptide sequence.

Plasmid pT7AD23K8 (5226 bp) is a derivative of pT7AD23k6 [Anderson, C. W., Virology, 177;259 (1990)] and also expresses the wild-type 204-amino acid EP polypeptide, but the DNA sequence (TTGAAA) corresponding to codons 200 (Leu) and 201 (Lys) of the proteinase gene [Roberts, R. J. et al., Adenovirus DNA: The Viral Genome and Its Expression (W. Doerfler, Ed.) 1–51 (1986)] in pT7AD23k6 was altered to introduce a unique AflII restriction site (C|TTAAG) without changing the EP protein sequence. The anti-sense strand EP carboxy-terminal oligonucleotide primer, 5'-CTTGGATCCATTATTTTTACA-TGTTCTTAAGGTGACAA-3' (SEQ ID NO: 26) and the sense strand T7 promoter sequence primer, 5'-TAATACGACTCACTATAGGGAGA-3' (SEQ ID NO: 25), were used to copy the EP gene of pT7AD23k6. The anti-sense primer has sequences corresponding to BamHI and AflII restriction sites (underlined); the BamHI site in the PCR product lies just after the position of the natural TAA termination codon in the Ad2 proteinase gene. After amplification, the NdeI (CA|TATG) and BamHI (G|GATCC)-cleaved PCR product was ligated with similarly cleaved pET-3C DNA to produce pT7AD23K8.

Figure 1A:
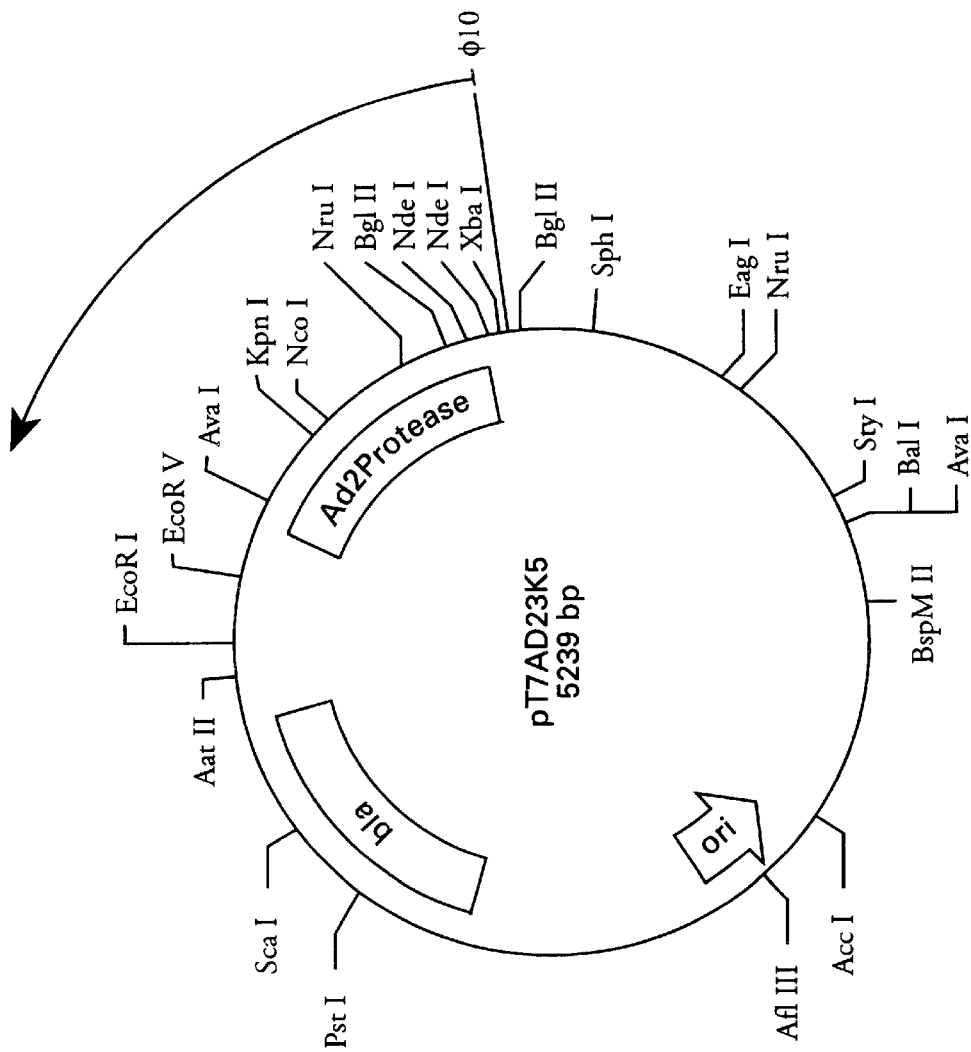
Figures 1A and 1B relate to a restriction site map of two Ad2 proteinase expression plasmids.
Figure 1B:
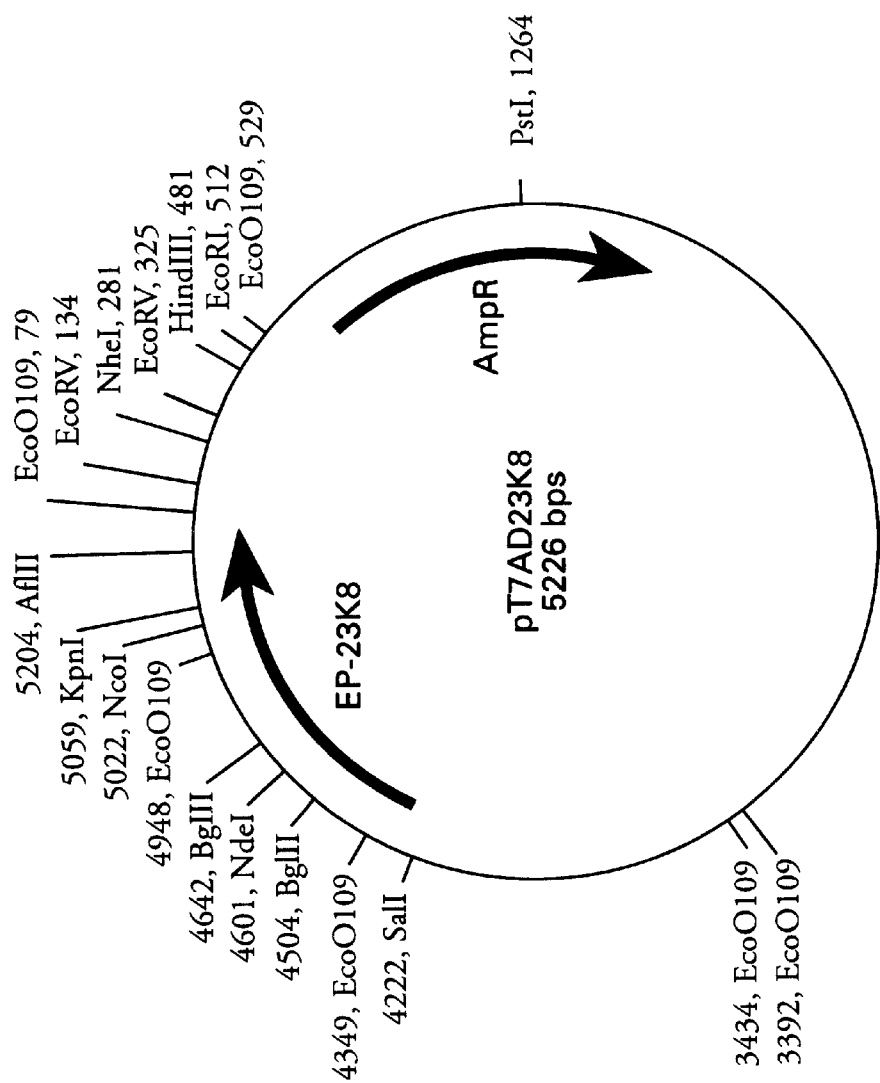

Both pT7AD23K8 and pT7AD23K10 differ from pT7AD23k6 in that adenovirus sequences 3' of the termination codon, which are not important for proteinase expression in E. coli, were removed, and a terminator for T7 polymerase transcription was placed in these plasmids to reduce excessive expression of the bla ampicillin-resistance gene (see FIG. 1).

pT7AD23K10 and pT7AD23K10 encode variants of the Ad2 proteinase. pT7AD23K10 encodes a deletion mutant missing the nine amino acids, Glu$_5$-Gln-Glu-Leu-Lys-Ala-Ile-Val-Lys$_{13}$ (see SEQ ID NO: 2), of the wild type Ad2 proteinase.

Plasmid pT7AD23K13 (5253 bp) is a derivative of pT7AD23K8 that expresses the wild-type Ad2 proteinase sequence with a 9-amino acid extension, -GHHHHHHNM (SEQ ID NO: 4), at the carboxy terminus. The oligonucleotides 5'-TTAAGAACATGGGTCACCACCACCATCAC-CATAACATGTAAAAAT-3'GATCCATTATTTTTACA-TGTTATGGTGATGGTGGTGGTGACCCATGTTC-3' (anti-sense strand; SEQ ID NO: 28), when annealed, form the required extension sequence with overlapping ends that are compatible with AflII and BamHI cleavage sites. The annealed oligonucleotides were ligated with AFlII and BamHI-cleaved pT7AD23K8 DNA to produce pT7AD23K13. A unique BstEII cleavage site (G|GTNACC; underlined), occurs in pT7AD23K13 at the beginning of the sequence that encodes the oligohistidine track.

Plasmids pT7AD23K15 and pT7AD23K16 are analogous to pT7AD23K5 and pT7AD23k6 [Anderson, C. W., Virology, 177;259 (1990)] except that they express the Ad12 EP polypeptide [Houde, A. and Weber, J. M., Nucleic Acids Res., 16;7195 (1988)]. The nucleotide and predicted amino acid sequences of the Ad12 proteinase are shown in the Sequence Listing (SEQ ID NO: 5 and NO: 6). The Ad12 EP gene was amplified with oligonucleotide primers 5'-CCCGTCGACCCATATGGGTTCAAGC-3' (sense strand) (SEQ ID NO: 29) and 5' CCCAAGCTTGTACTCCAATG-3' (anti sense strand) (SEQ ID NO: 30). The amino-terminal sense strand primer is homologous to pT7AD23K5 [Anderson, C. W., Virology, 177;259 (1990)] between the SalI site (G|TCGAC) and the NdeI site; following the NdeI recognition sequence are nine nucleotides homologous to the Ad12 EP sequence. The carboxy-terminal anti-sense primer has sequence corresponding the HindIII site (A|AGCTT; underlined) following the Ad12 EP termination codon. The amplified Ad12 EP gene was cleaved with SalI and HindIII and ligated with similarly cleaved pT7AD23K5 DNA. pT7AD23K16 was produced by cleaving pT7AD23K15 DNA with NdeI and relegating. This removed the small NdeI fragment that encodes the OmpT leader sequence [Anderson, C. W., Virology, 177;259 (1990)] and places the initiation codon for the Ad12 EP at the translation start site of the pET-3 expression cassette.

Plasmid pT7AD23K18 (5225 bp) is a derivative of pT7AD23K8 that expresses the EP sequence from the temperature-sensitive mutant, H2ts1 [Weber, J., J. Virol., 17;462 (1976)]. The H2ts1 mutation lies between the BglII site at Ad2 nucleotide 21,816 and the KpnI site at 22,237 [Yeh-Kai, L. et al., J. Mol. Biol. 167;217 (1983)) ] [Roberts, R. J. et al., Adenovirus DNA: The Viral Genome and Its

*Expression* (W. Doerfler, Ed.) 1–51 (1986). This 422-bp fragment was isolated from restriction enzyme-digested H2ts1 DNA by gel electrophoresis, and it was inserted into pT7AD23K8 in place of the corresponding wild-type fragment. The presence of the H2ts1 mutation was confirmed by cleaving pT7AD23K8 and pT7AD23K18 with HaeIII; the ts1 mutation removes a HaeIII restriction site present in the wild-type Ad2 sequence.

Expression of Recombinant Adenovirus Proteinases In Bacterial Cells

To obtain bacterial cells which express the recombinant adenovirus proteinases, the expression plasmids described above were used to transform an *E. coli* strain, BL21(DE3), which is capable of expressing the T7 RNA polymerase. In BL21(DE3), the T7 RNA polymerase ceding sequence is integrated into the bacterial chromosome 3' of the regulatory elements of the lactose operon. Thus, expression of the T7 RNA polymerase can be induced by adding isopropylthiogalactoside (IPTG). T7 RNA polymerase efficiently transcribes a coding sequence inserted into the expression cassette of a pET vector-based plasmid beginning at the T7 $\phi$10 promoter (see FIG. 1). Consequently, after IPTG induction, mRNA transcripts of the coding sequence accumulate rapidly, and the protein product is synthesized at a high rate. Thus, in the pET vector/BL21(DE3) host cell expression system, IPTG induces expression of the recombinant adenovirus proteinase.

BL21(DE3) cells were transformed with each of the above-described adenovirus proteinase expression plasmids. Transformed cells were selected by ampicillin-resistance. Cultures of the transformed cells were grown to mid-log phase, and IPTG was added to induce synthesis of the recombinant proteinase. Soluble extracts of the cells were then prepared for characterization of the expression products.

The following terms will be used in describing the expression and characterization of recombinant adenovirus proteinases. A strain of transformed cells is designated by the plasmid name/host bacterial strain name, e.g., pT7AD23K5/BL21 (DE3). The recombinant proteinase produced by expression of the plasmid is designated by the last four or five characters (i.e., to accommodate 23K10) in the plasmid's name, e.g., 23k5. Precursor and processed forms of OmpT-proteinase fusion proteins, which can be detected as two separate bands on SDS-polyacrylamide gels, may be designated separately, e.g., 23k5a and 23k5b.

Figure 3:
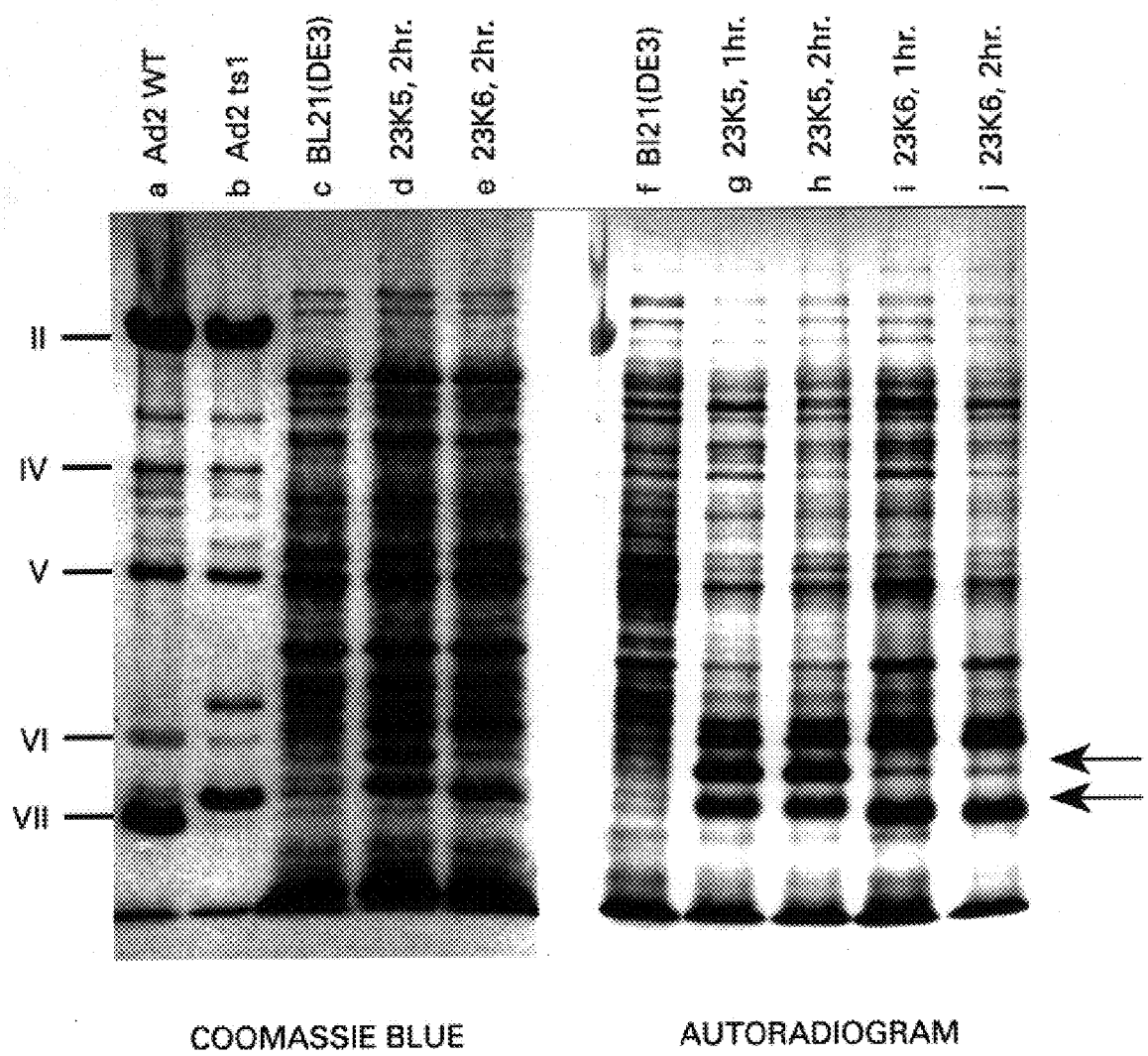
FIG. 3 shows the expression of recombinant Ad2 proteinases 23k5 and 23k6 in *E. coli* after IPTG induction. Left: SDS-polyacrylamide gel stained with Coomassie Blue. Right: Autoradiogram of the pulse-labeled proteins.

FIG. 3 shows the expression of plasmids pT7AD23K5 and pT7AD23k6 in BL21 (DE3) cells after induction. Log phase cultures of untransformed (lanes c and f), pT7AD23K5-transformed (lanes d, g, and h), and pT7AD23k6-transformed (lanes e, i, and j) BL21(DE3) cells were pulse-labeled for 5 minutes with [$^{35}$S]methionine at 1 (lanes g and i) and 2 hours (lanes c–f, h and j) after IPTG induction. Bacterial extracts were prepared immediately after labeling and run on SDS-polyacrylamide gels (SDS-PAG). Shown are a Coomassie Blue-stained gel (left) and an autoradiogram of the gel (right). The positions of the proteinases, including precursor and processed fusion proteins, are indicated (arrows). The well-induced polypeptide just above these (lanes g–j) is probably $\beta$-lactamase. Proteins of purified Ad2 (lane a) and H2ts1 mutant virions (lane b) were also run on the gel.

As shown in FIG. 3, the recombinant proteinases quickly became the most rapidly synthesized protein after induction, and rapid synthesis continued for more than 2 hours after induction (lanes f–j). Synthesis of the active 23k6 proteinase did not decrease over this prolonged period.

Nearly equal amounts of a 25 kDa protein (23k5a) and a 23 kDa protein (23k5b) were produced from pT7AD23K5 (lane d), suggesting that 23k5a and 23k5b are the precursor and cleaved forms of the encoded OmpT-proteinase fusion protein. Pulse-chase experiments confirmed that a portion of the 25 kDa protein was rapidly processed to the 23 kDa protein. The 25 kDa protein that was not processed within about 5 minutes of synthesis was stable, even several hours after synthesis. Amino-terminal sequence analysis indicated that the 23 kDa protein begins with serine$_2$ (see FIG. 2; SEQ ID NO: 10). Similar results were obtained from expression of pT7AD23K2 (Table 1). These results indicate that processing of the OmpT signal peptide sequence of the fusion proteinases occurred as would be expected if the OmpT leader were processed by the *E. coli* membrane-associated signal peptidase.

The 23k5 and 23k6 products were tested for solubility as an indication of protein folding. Induced bacteria were harvested and lysed with lysozyme-EDTA, and 10,000×g supernatants were prepared. In each case, the majority of the proteinase was found in the insoluble pellet. When pellet fractions were analyzed by SDS-polyacrylamide gel electrophoresis (SDS-PAGE) in the absence of a reducing agent, only a small fraction of the proteinase protein entered the stacking gel, indicating that most of the bacterially synthesized proteinase was misfolded and crosslinked through disulfide bonds. This was observed for both 23k5 precursor and processed proteins, as well as for the 23k6 proteinase.

Expression of the Mutant Proteinase Found in H2ts1 Ad2 Virus

Plasmid pT7AD23K18 expresses the mutant EP found in H2ts1 virus [Yeh-Kai, L. et al., *J. Mol. Biol.* 167;217 (1983)]. This plasmid was made by replacing the BglII-KpnI fragment in the EP gene of pT7AD23K8 with the equivalent fragment from H2ts1 DNA. The recombinant H2ts1 EP was expressed as well as the wild-type EP polypeptide, but it bound poorly to the Zn-affinity column. A Sepharose column was substituted for the Zn-affinity column purification step. No EP activity was observed when DEAE flow-through fractions from pT7AD23K18/BL21(DE3) were assayed in the presence of H2ts1 virions even though the H2ts1 proteinase had been synthesized in cultures grown at 30° C., a temperature below that required to obtain activity from H2ts1 virions. *E. coli* cytosol appears to be a marginal environment for folding of the wild-type adenovirus EP; the H2ts1 EP may be sufficiently destabilized that it is unable to fold correctly in this foreign environment.

Activity and Amino-Terminal Sequences of the Recombinant Proteinases

The expression products of the above-described Ad2 and Ad12 proteinase plasmids were tested for their ability to cleave the Ad2 major core protein precursor, pVII, in crude extracts from adenovirus-infected cells. The extracts were obtained from human cells infected with the temperature-sensitive mutant Ad2 strain, H2ts1, which has a defective proteinase. As described below, adenovirus proteinase activity requires the presence of two cofactors. Since these two cofactors are provided by the crude extract in the assay, the proteinase activity determined by this assay indicates that the adenovirus proteinase is functional, or activatable. The recombinant proteinases were also characterized by peptide sequence analysis of their amino-termini. Table 1 summarizes the results of the activity assays and amino-terminal sequence analysis.

Figure 4:
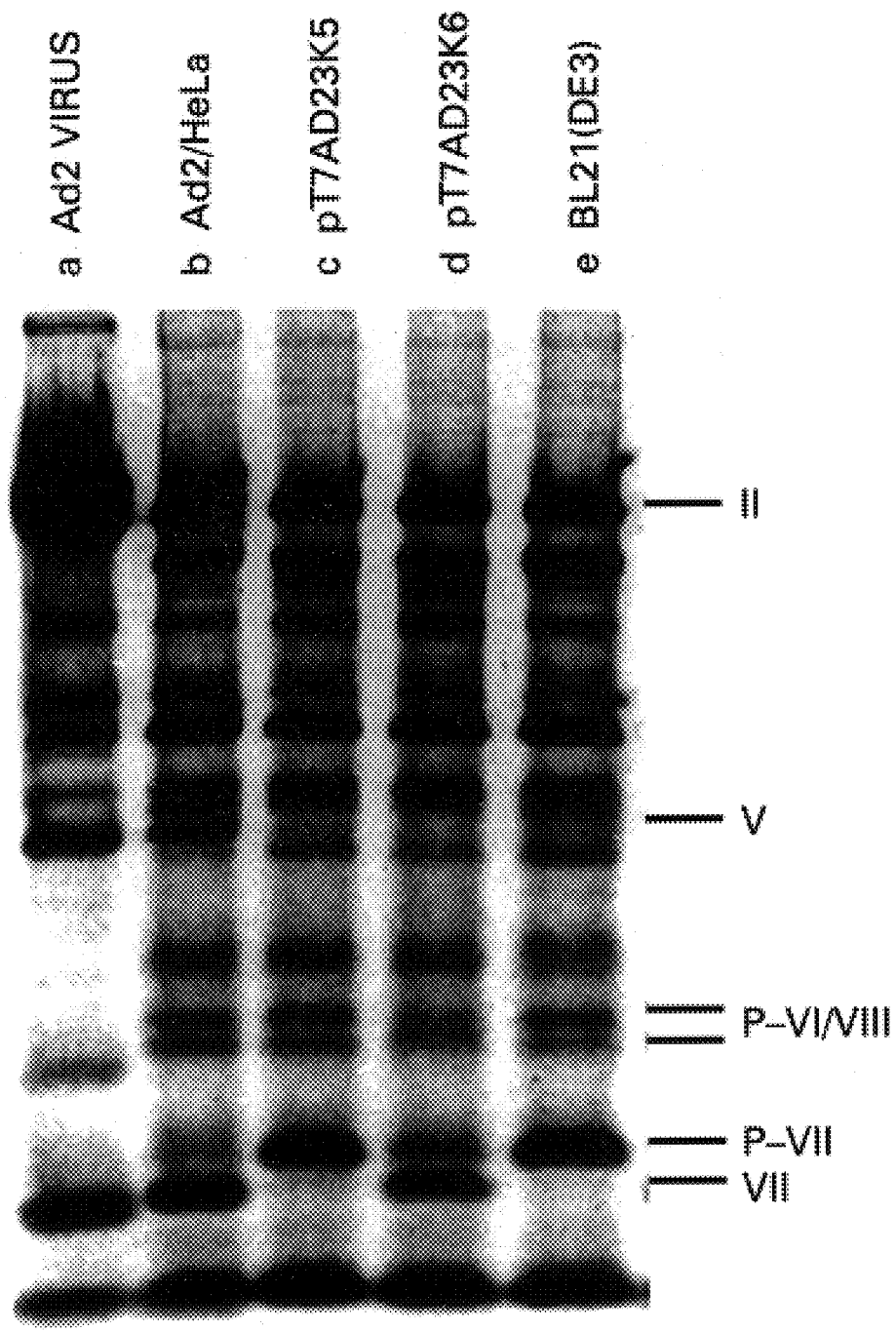
FIG. 4 is an autoradiogram of an Ad2 proteinase assay experiment.

FIG. 4 shows the results of activity assays on 23k6 and 23k5. Bacterial extracts were incubated with the radiolabeled substrate (pVII). Samples were removed at different times and analyzed by SDS-PAGE and autoradiography. FIG. 4 shows an autoradiogram of samples taken after 90 minutes of incubation. Appearance of the processed VII band and concurrent decrease of the precursor pVII band indicates proteinase activity. Radiolabeled proteins of Ad2 virions were run on the gel to indicate the positions of pVII, VII, and other virion components (lane a). Extracts from Ad2-infected HeLa cells were assayed as a positive control for proteinase activity (lane b). Lane e shows the results of a negative control, in which extracts from nontransformed BL21(DE3) cells were assayed.

As shown in FIG. 4, the 23k6 proteinase possesses significant proteinase activity (lane d) in this assay system. Comparison of the assay at various time points indicated that the 23k6 proteinase caused rapid processing of the precursor pVII to VII. By 2 hours virtually all of pVII had been converted to VII. 23k6 proteinase activity was distributed equally between soluble and insoluble fractions of the E. coli extract, despite the fact that the majority of the 23k6 was in the insoluble fraction.

The recombinant Ad2 proteinases 23k6, 23K8, 23K10, and 23K13 and the recombinant Ad12 proteinase 23K16 were all found to be active in the assay. 23k6, 23K8, and 23k10 were further characterized by amino-terminal sequence analysis and found to have a mixture of amino-termini with and without the initiating methionine (Table 1). During synthesis of these polypeptides, the amino-terminal methionine of the nascent product appears to be occasionally removed by enzymes that are present in E. coli. The 23k6, 23K8, and 23K10 proteinases are thus expected to be a mixture of 204 and 203 amino acid polypeptides. The relative amounts of the amino-termini with and without $Met_1$ for each of these proteinases differed from experiment to experiment and could be as much as 50%. Deletion of the initiating methionine did not seem to be detrimental to the function of the recombinant proteinase produced.

23K13, an Ad2 proteinase variant, was found to be as active as 23k6 in the assay. Thus, the addition of a peptide sequence (SEQ ID NO: 4) to the carboxy-terminus of the proteinase did not appear to be detrimental to proteinase function. 23K11, the Ad2 proteinase deletion variant, which lacks the nine amino acids from $Glu_5$ to $Lys_{13}$ (see SEQ ID NO: 2) near the amino-terminus, was not active in cleaving P-VII, suggesting that the amino-terminal region is critical for the function of the proteinase.

In FIG. 4, the absence of the VII band in lane c indicates that the 23k5 precursor and processed fusion proteins had no detectable activity. No activity was observed even after a 20 hour incubation. This finding is significant in the context of production of foreign proteins in E. coli. Many foreign proteins fold improperly or inefficiently when expressed in E. coli. pT7AD23K5 was constructed with the hope that the proteinase polypeptide might be transported by the OmpT signal sequence through the plasma membrane to the periplasm, where, after cleavage of the signal sequence, the polypeptide might fold into soluble, active proteinase. The processing of the 23k5 fusion protein in bacterial cells indicated that, although signal sequence cleavage occurred, proper folding and/or disulfide bond formation did not.

Although no detectable activity was produced in pT7AD23K5-transfected cells when grown to log phase and induced with IPTG, some proteinase activity was observed in extracts from uninduced cells grown to stationary phase. This activity was less than the activity of 23k6 produced in induced, log phase cells. The other fusion proteinases, 23K1 and 23K2, gave similar results. No proteinase activity was observed for the deletion mutant protein, 23K11, when produced in either uninduced, stationary or induced, log phase cells.

Sequence Confirmation of the 23k6 Proteinase

Two amino-terminal sequences were identified for 23k6, which were identical except for the initial methionine (Table 1). The relative amounts of the two amino-termini varied from experiment to experiment. Assuming that the structure of the proteinase coding sequence in pT7AD23k6 is correct and that no processing occurred at the carboxy-terminus, these amino-terminal sequences predict a 203 amino acid proteinase without the initiating methionine and a 204 amino acid proteinase with the methionine. Further sequence analysis was performed on tryptic peptides derived from 23k6. Together with the amino-terminal sequence, tryptic peptide analysis directly confirmed one-third of the predicted proteinase sequence, including 24 residues of the carboxy-terminal sequence (FIG. 6). Radiochemical sequence analysis of the insoluble fraction after trypsin digestion was also consistent with the presence of $Cys_{17}$ and/or $Cys_{67}$, and $cys_{122}$, $Cys_{126}$, and $Cys_{127}$. Thus, peptide sequence analysis confirmed that the 23k6 protein is the 204 (or 203 without the initial methionine) amino acid Ad2 proteinase predicted from the nucleotide sequence of the Ad2 genome (SEQ ID NO: 1 and NO: 2).

Purification of Activatable Recombinant Adenovirus Proteinase from E. coli

A preferred scheme for purifying activatable recombinant proteinases from E. coli is described in Examples 8 and 9. Briefly, a culture of transformed bacterial cells was grown to mid-log phase, and IPTG was added to induce synthesis of the recombinant proteinase. The lysed bacteria were centrifuged to separate the soluble (supernatant) and the insoluble (pellet) fractions. Recombinant proteinase was purified from the soluble or supernatant fraction of lysed bacteria by DEAE-Sepharose chromatography, followed by affinity chromatography on zinc-loaded Chelating-Sepharose. Greater than 90% of the protein in the eluate from the Chelating-Sepharose column is adenovirus proteinase as judged by SDS-PAGE. If required, the proteinase can be further purified on other supports such as gel filtration and cation exchange columns. Recombinant proteinase, such as 23k6, purified by this method is highly active in the crude extract assay.

Approximately 1–2 mg of purified, activatable Ad2 proteinase can be obtained from a liter of pT7AD23k6-transformed cells (Example 9). The high yield of functional 23k6 proteinase was found to be obtained if the transformed cells were incubated at 30° C. rather than 37° C. after induction. Incubation at 37° produces a preparation in which most of the polypeptides are misfolded; however, if the incubation temperature is lowered to 30° at addition of IPTG, approximately half of the recombinant proteinase folds into a soluble protein and a higher yield of activatable proteinase is obtained.

The substantial activity observed for the recombinant proteinase, 23k6, in the crude extract assay is significant in the context of bacterial production of foreign proteins. Expression of high amounts of a foreign protein in bacterial host cells was expected to be detrimental to the growth of the bacterial cells or to solubility and correct folding of the protein in the cells, leading to poor yields of recombinant proteinase. However, prolonged synthesis of the 23k6 polypeptide in induced cells (FIG. 3) and substantial yields of activatable 23k6 and other recombinant proteinases mentioned above indicated that these were not critical problems in the method of production described herein. As discussed, lowering the incubation temperature of the host cells after induction of proteinase expression to about 30° C. improves the yield of activatable protein. This is probably due to a slowing down of the rate of accumulation of the protein in the cell, which may favor functional folding of a higher proportion of the proteins expressed. This advantage is offset by the lower rate of total protein synthesis. Longer incubation times at lower temperatures than about 30° (e.g., 20°) may result in even better activity yields, if the recombinant proteins are stable in the cell. Optimization of the incubation temperature and testing of other growth conditions to improve yield, especially growth conditions which slow the rate of protein synthesis in the host cells, can be performed using the methods of production and proteinase assays described herein.

Production of Activatable Recombinant Proteinase in a Baculovirus Vector/Insect Cell Expression System A baculovirus vector, vNPVAd2EP, was made for expressing the Ad2 proteinase in Sf9 insect cells (Example 10). In the vector, the Ad2 proteinase coding sequence replaces the polyhedron protein gene. The recombinant Ad2 proteinase was purified by a procedure similar to that described above for purification from E. coli, and found to be active in the crude extract assay.

Adenovirus Proteinase Activity Requires Two Cofactors

Two assays were developed to monitor proteinase activity in the absence of adenovirus virions or infected cell extracts. The first involved use of recombinant proteins containing a leader sequence connected to a protein through an amino acid segment corresponding to an adenovirus proteinase recognition and cleavage sequence. The second involved synthesis of a fluorogenic compound, a peptide derivative of rhodamine which, when cleaved by the adenovirus proteinase, becomes highly fluorescent.

Figure 7A:
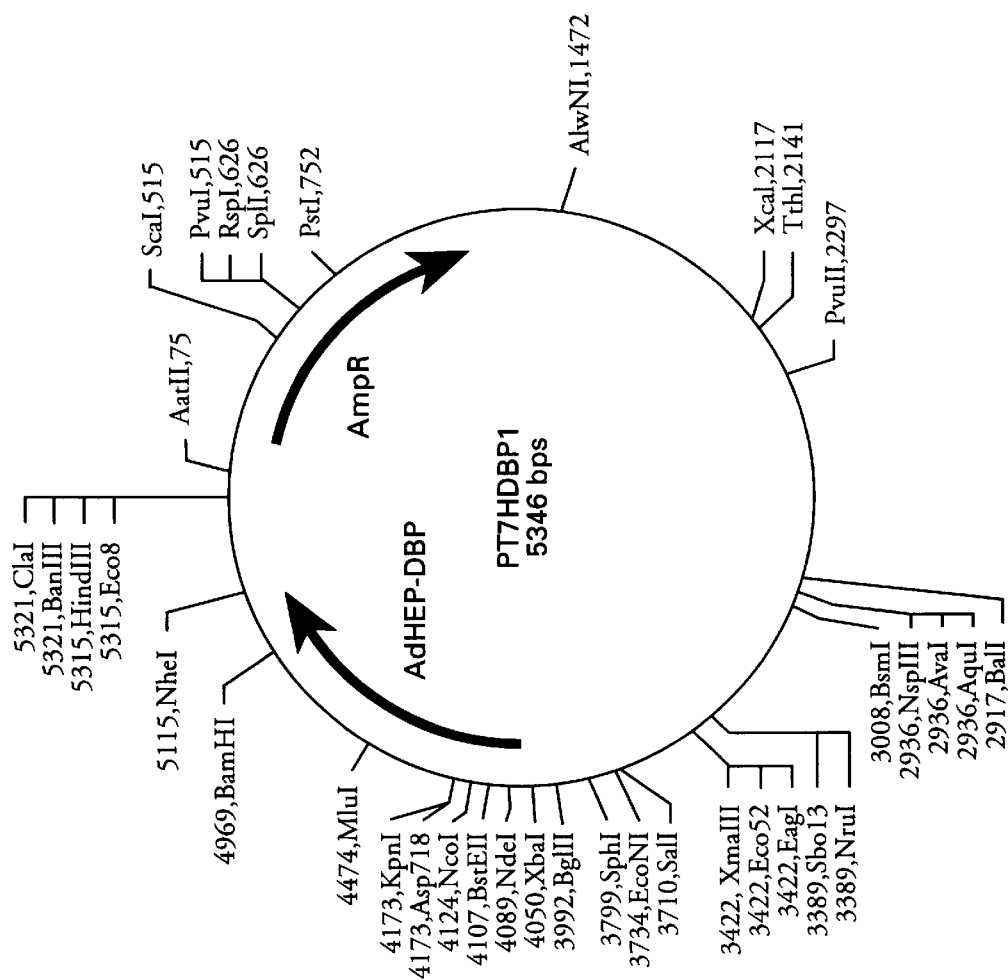
FIGS. 7A and 7B relate to monitoring of proteinase activity.

Recombinant protein substrates that resemble natural virion precursors, such as pVI, can be produced in E. coli by genetic engineering methods similar to those used for expression of recombinant adenovirus proteinase. The recombinant substrate may have an artificial leader sequence that can be removed by proteinase-mediated cleavage. The leader can be designed to aid in purification of the substrate; thus the recombinant substrate can be produced and purified much more efficiently than natural adenovirus substrates. Recombinant protein substrates also serve as prototypes of potential commercial products, showing that the adenovirus proteinase will remove an artificial leader sequence from a recombinant protein that is not related to any adenovirus protein. The first artificial protein substrate was called HEP1DBP. It consists of a 17 amino acid leader (Met-Ala-Ser-Met-Thr-Gly-His-His-His-His-His-His-Gly-Met-Ser-Gly-Gly-) (SEQ ID NO: 37) attached to the initiating methionine of the 232 amino acid DNA binding protein (DBP), of bacteriophage T7. The T7 DBP is the product of gene 2.5. The recombinant proteinase substrate is produced by induction of a pET expression plasmid called pT7HEP1DBP (also called pT7HIS2) (FIG. 7A and Example 11); the predicted sequence of the expressed substrate is given in Table 1. The leader sequence contains six consecutive histidine residues to permit purification by metal affinity chromatography in a manner analogous to purification of the adenovirus proteinase. Immediately preceding the methionine corresponding to the initiation site of the T7 DBP is the tetra-amino acid element -Met-Ser-Gly-Gly- (SEQ ID NO: 38). This segment corresponds to the proteinase recognition sequence in the adenovirus virion precursor polypeptide pVI. The size of the leader sequence was chosen so that the substrate precursor HEP1DBP, and the predicted major product after cleavage, the T7 DBP, could easily be distinguished by SDS-polyacrylamide gel electrophoresis.

TABLE 1

Predicted Sequence and Composition of the Expression Product Recombinant Adenovirus Proteinase Substrate AdHEP-DBP Segment: 4092–4841
Composition 249 Residues

| 22 Ala A | 3 Cys C | 8 His H | 8 Met M | 11 Thr T |
|---|---|---|---|---|
| 6 Arg R | 3 Gln Q | 7 Ile I | 9 Phe F | 3 Trp W |
| 8 Asn N | 26 Glu E | 10 Leu L | 13 Pro P | 11 Tyr Y |
| 20 Asp D | 24 Gly G | 25 Lys K | 14 Ser S | 18 Val V |

```
            5          10          15         20
  1 M A S M T G H H H H H H G M S G G M A K
 21 K I F T S A L G T A E P Y A Y I A K P D
 41 Y G N E E R G F G N P R G V Y K V D L T
 61 I P N K D P R C Q R M V D E I V K C H E
 81 E A Y A A A V E E Y E A N P P A V A R G
101 K K P L K P Y E G D M P F F D N G D G T
121 T T F K F K C Y A S F Q D K K T K E T K
141 H I N L V V V D S K G K K M E D V P I I
161 G G G S K L K V K Y S L V P Y K W N T A
181 V G A S V K L Q L E S V M L V E L A T F
201 G G G E D D W A D E V E E N G Y V A S G
221 S A K A S K P R D E E S W D E D D E E S
241 E E A D E D G D F *
```

NBC: Ad2 proteinase cleaves after residue 17; residues 14–17 correspond to the sequence of Ad2 virion component pVI immediately before the aminoterminal cleavage site; T7 Gene product 2.5 sequence starts at residue 18.

When purified HEP1DBP was incubated with disrupted wild-type adenovirus 2 virions, it was cleaved, as determined from the change in its mobility during SDS-polyacrylamide gel electrophoresis. No cleavage was observed when incubation was with disrupted H2ts1 virions alone. Surprisingly, no cleavage was observed when HEP1DBP was incubated with purified 23k6 or 23K8 alone, but cleavage was obtained when purified 23K8, HEP1DBP, and disrupted H2ts1 virions were incubated together. Furthermore, protein sequence analysis showed that cleavage occurred between the last amino acid of the leader sequence and the methionine corresponding to the start of T7 DBP, as expected for Ad2 proteinase activity. These results showed that one or more additional components are required for activation of the Ad2 proteinase and that these cofactors are present in adenovirus virions. The addition of purified adenovirus DNA to reactions containing 23K8 and HEP1DBP did not stimulate cleavage of the HEP1DBP substrate. This result suggested that one proteinase cofactor was a protein or peptide. That one cofactor was protein was confirmed by the finding that pre incubation of H2ts1 virions with trypsin, and subsequent inactivation of the trypsin (by adding a trypsin inhibitor, soybean trypsin inhibitor, that does not inhibit the adenovirus proteinase) inactivated a component in H2ts1 virions required for proteinase activity.

The nature of the proteinase cofactor(s) was pursued with the aid of the second assay, which utilizes the substrate (Leu-Arg-Gly-Gly-NH)$_2$-rhodamine. The design of this substrate was based on two facts. (1) It was known that the proteinase present in disrupted Ad2 virions would cleave small peptides with sequence similar to that found at natural cleavage sites in adenovirus virion precursors (Webster et al., 1989). (2) Cleavage of either tetra-peptide sequence from the substituted rhodamine substrate produces a very large increase, up to a 3500-fold, in fluorescence. Under conditions where only a small fraction of the rhodamine substrate is cleaved, the increase in fluorescence is proportional to the amount of proteinase present and to the time of incubation. Thus, the fluorescence assay provides a quantitative method for assessing proteinase activity that is more sensitive convenient and rapid than the gel electrophoresis assay.

Figure 7B:
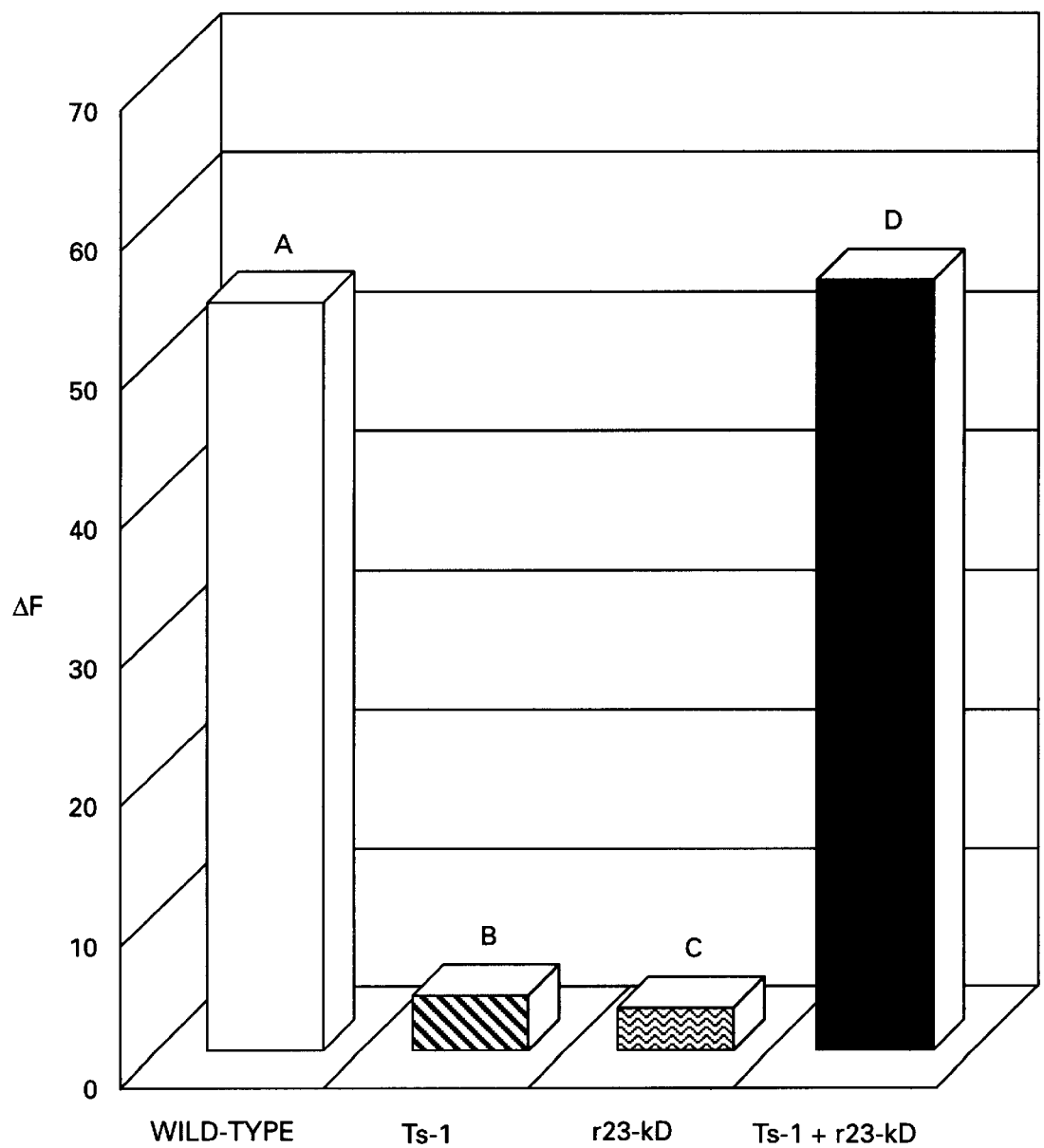

FIG. 7B shows the initial results of the fluorescence assay. Disrupted wild type Ad2 virus was positive and disrupted H2ts1 virus was negative for activity, as expected. However, purified recombinant Ad2 proteinase gave no activity. Activity was obtained from the recombinant proteinase complemented with disrupted H2ts1 virus. This suggested that cofactors present in adenovirus are required for activation of the proteinase. As described herein, it has been determined that activation of the purified recombinant proteinase (referred to as rEP or an activatable proteinase) required the presence of two cofactors.

Figure 8:
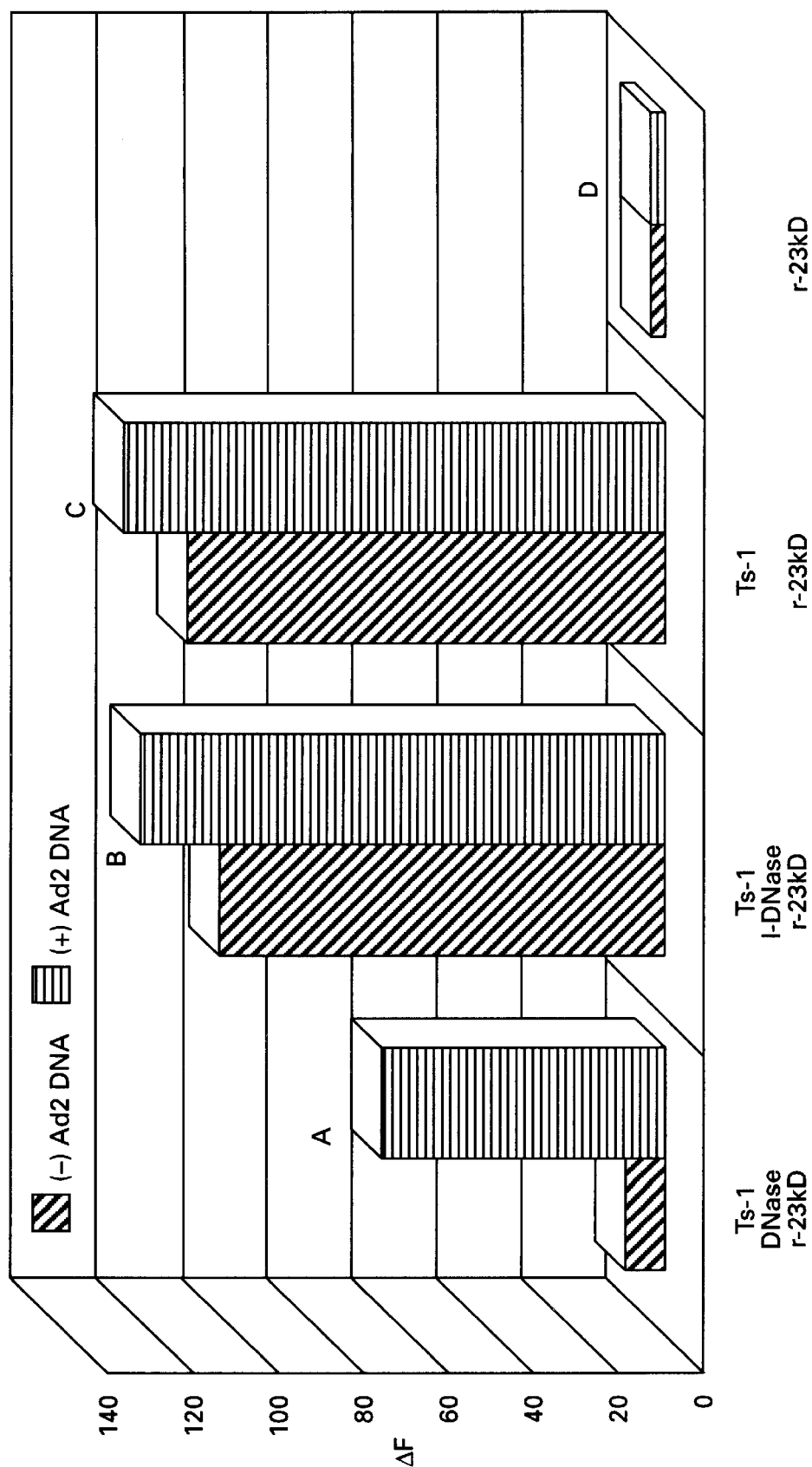
FIG. 8 shows the effect of DNase and Ad2 DNA on cofactor activity in H2ts1 virus: (A) DNase-treated H2ts1 virus; (B) H2ts1 treated with inactivated DNase; (C) untreated H2ts1 virus; and (D) no H2ts1 virus. Dark and open bars indicate without and with addition of Ad2 DNA, respectively.

One cofactor was found to be DNA. When disrupted H2ts1 virus was treated with DNase prior to the assay, 94% of the proteinase activity obtained with untreated H2ts1 virus was lost (FIG. 8). Subsequent addition of Ad2 viral DNA restored activity to about 70% of that obtained with untreated H2ts1 virus (A and C). To determine whether proteinase activity was dependent on specific nucleotide sequences, various polymers were later substituted for Ad2 DNA (Table 3). No sequence-specific requirement was evident. Not only did T7 DNA substitute for Ad2 DNA, but also single-stranded DNAs, circular single- and double-stranded DNAs, and even transfer RNA. Rather, it appeared as if the requirement was for a polymer with high negative charge density. Polyglutamic acid, polyaspartic acid and heparin substituted for Ad2 DNA in vitro but not the four deoxyribonucleoside monophosphates, glutamic acid, aspartic acid or polylysine (Table 3).

The use of DNA as a cofactor of adenovirus proteinase activity is novel for a proteinase, and suggests the existence of a new class of DNA-dependent proteinases. The viral DNA is most probably required for proteinase activity in Ad2 virions, because proteinase activity with disrupted ts-1 virions is lost on treatment with DNase and is restored on addition of Ad2 DNA.

Figure 9:
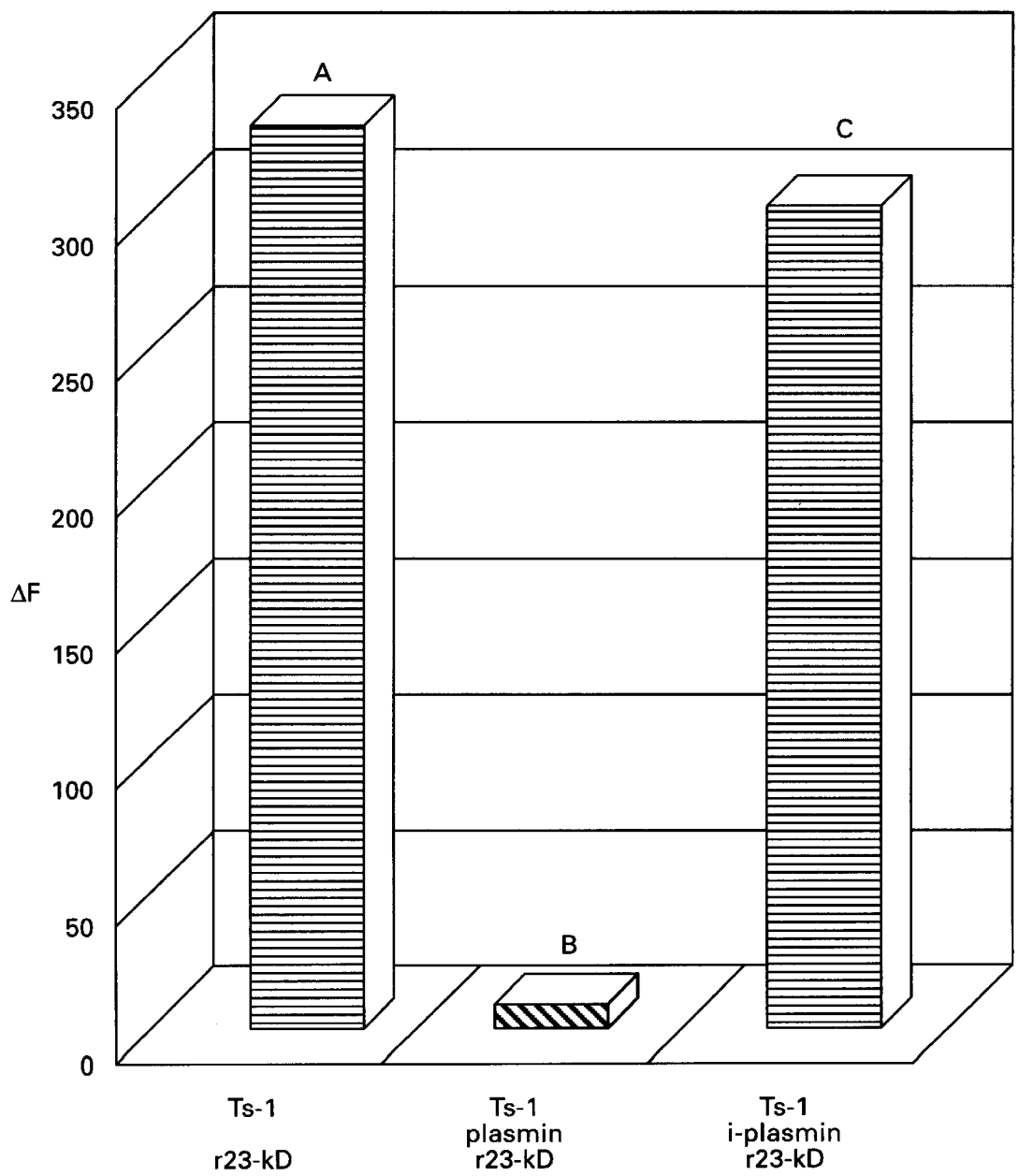
FIG. 9 shows the effect of plasmin on cofactor activity in H2ts1 virus: (A) untreated H2ts1 virus; (B) plasmin-treated H2ts1 virus; and (C) H2ts1 virus treated with inactivated plasmin.

Adenoviral DNA along with the recombinant proteinase was insufficient to reconstitute proteinase activity (FIG. 8D), suggesting the requirement for another cofactor. As described above, results indicated that the second cofactor is a protein (FIG. 9).

Figure 10:
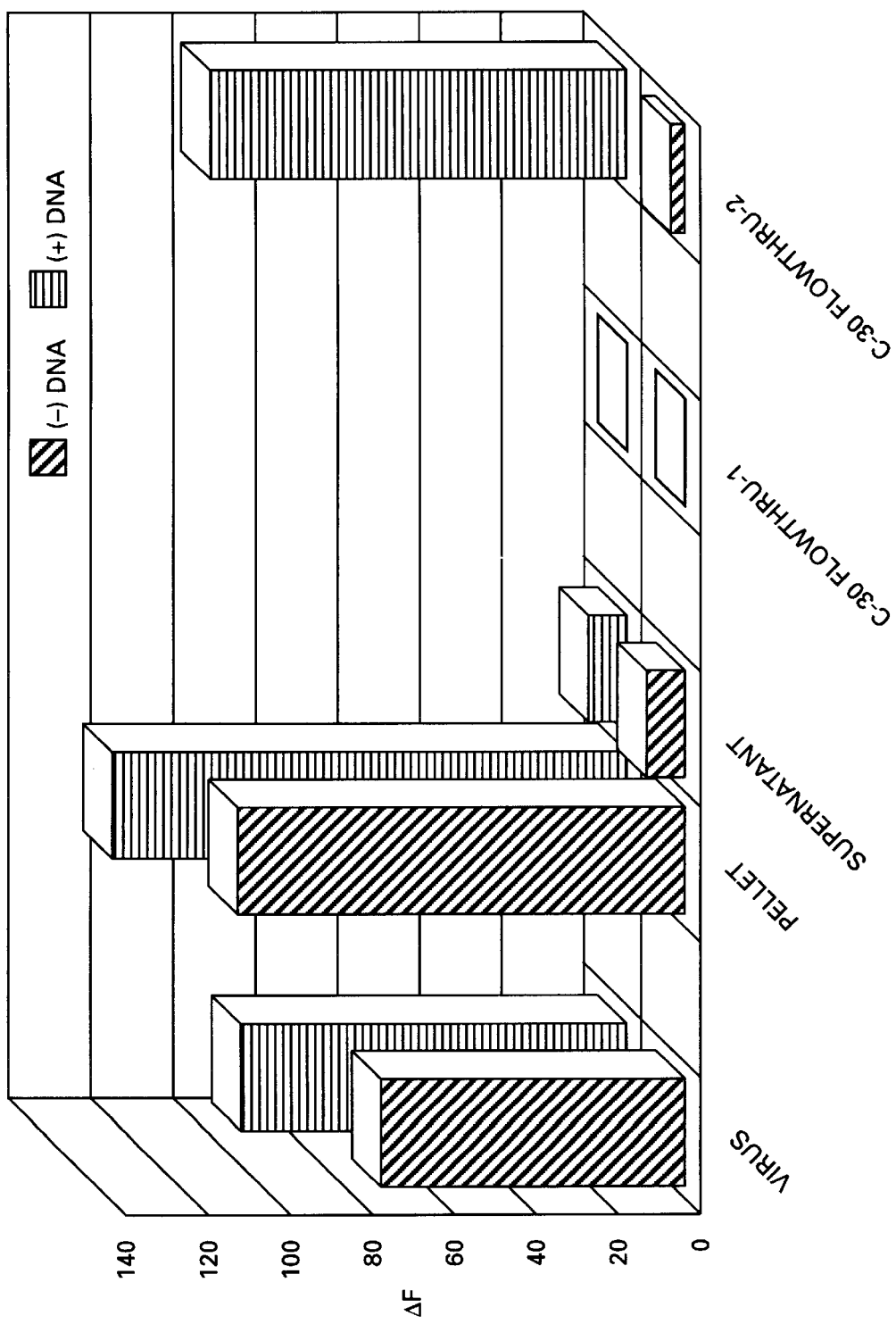
FIG. 10 shows purification of the peptide cofactor by filtration in Centricon-30.
Figure 11A:
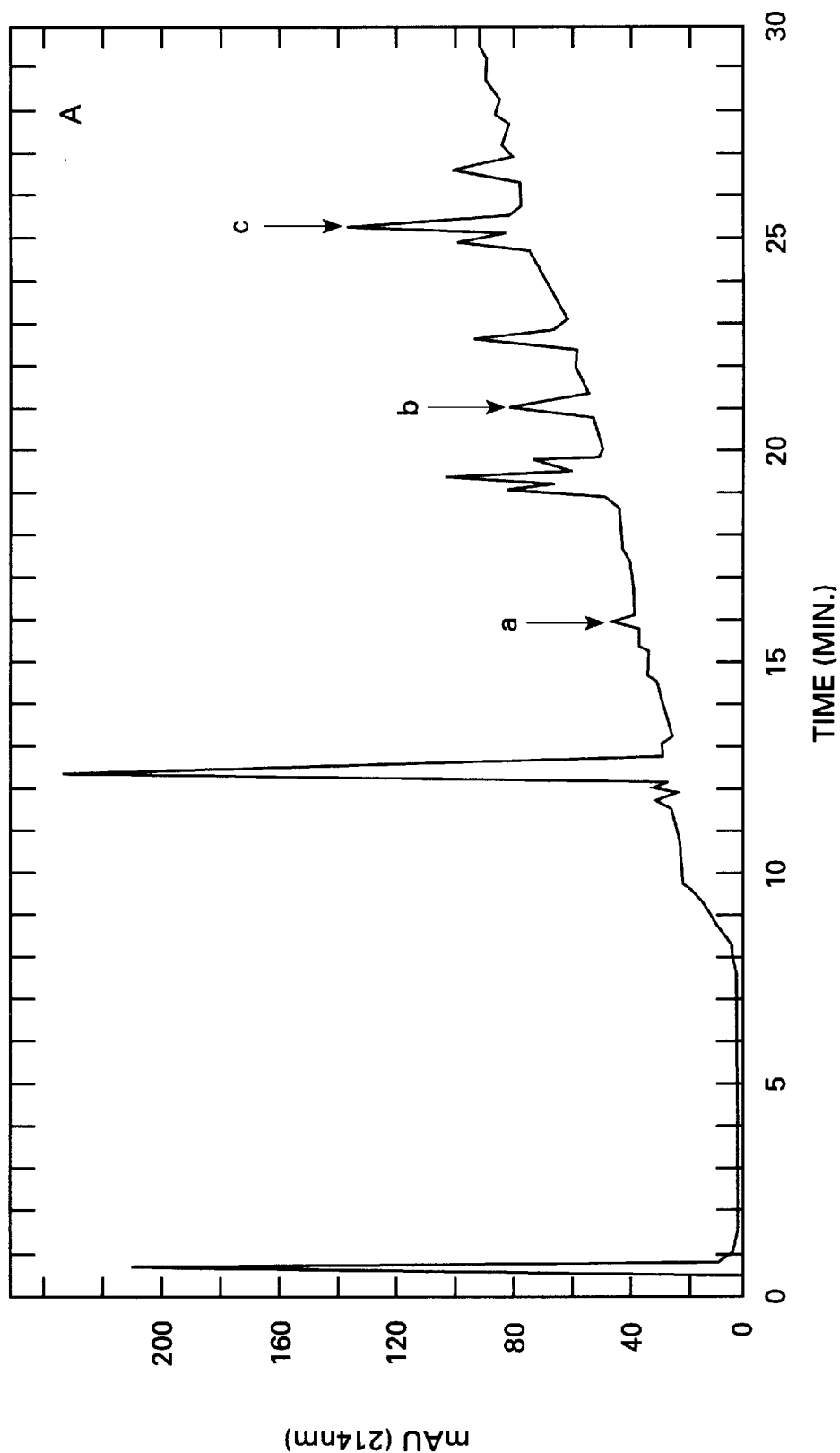
FIG. 11A shows the elution profile from the reverse phase column. Arrows indicate peaks containing peptide cofactor activity.
Figure 11B:
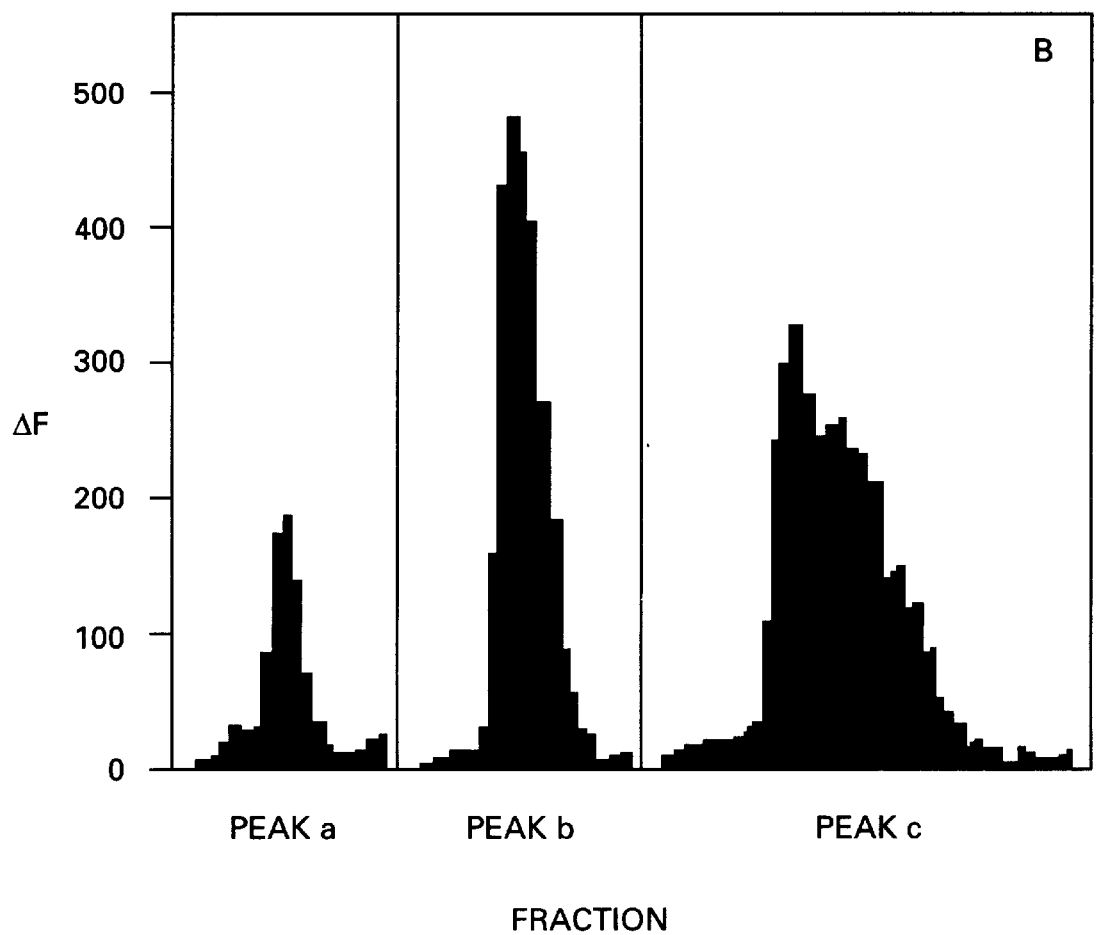
FIG. 11B shows the proteinase activity obtained in fluorescence assays of the fractions in each peak.

The protein cofactor was purified by filtration through a membrane with a 30 Kda molecular weight cutoff pore size, followed by reverse phase chromatography (FIGS. 10 and 11; Example 12). Three peaks from the reverse phase column contained proteinase activity (FIG. 11). Of the total cofactor activity applied to the column, 7% was recovered in peak a, 22% in peak b, and 14% in peak c. The final yield was greater than 49%.

The amino acid sequence of the proteins in each of the three peaks was determined. The results indicate that the proteins in the three peaks have almost identical amino acid sequences (FIG. 12; amino acids 240–250 of SEQ ID NO: 15). The differences were in the yield of lysine at position 6, suggesting a modified lysine residue at this position. No amino acid was detected at position 10 where a cysteine is expected. The 11 amino acid sequence corresponds to the carboxyterminus of the precursor to the Ad2 virion component VI (pVI, whose predicted amino acid sequence is also shown in FIG. 12; SEQ ID NO: 15). The pVI sequence has two consensus cleavage sequences, one beginning at residue 29, MSGG, and the other at 236, IVGL (underlined). Cleavage at the latter site would liberate the 11 amino acid cofactor.

The requirement for the 11-amino acid second cofactor from the carboxy terminus of pVI seemed to be specific. A peptide similar in character, Cys-Gly-Tyr-Gly-Pro-Lys-Lys-Lys-Arg-Lys-Val-Gly-Gly, did not substitute for the pVI-c peptide.

The viral DNA and pVI-c peptide may be required for proteinase activity in vivo to ensure that virion precursor proteins are processed only after virion assembly; otherwise, they may not be able to assemble into a virus particle. Perhaps the viral DNA serves as a scaffold for the assembly of proteinase complexes adjacent to the >3,000 processing sites that must be cleaved to produce an infectious virus particle.

Alternatively, the viral DNA could serve as a guide wire on which the proteinase complex moves as it cleaves precursor proteins.

Figure 13A:
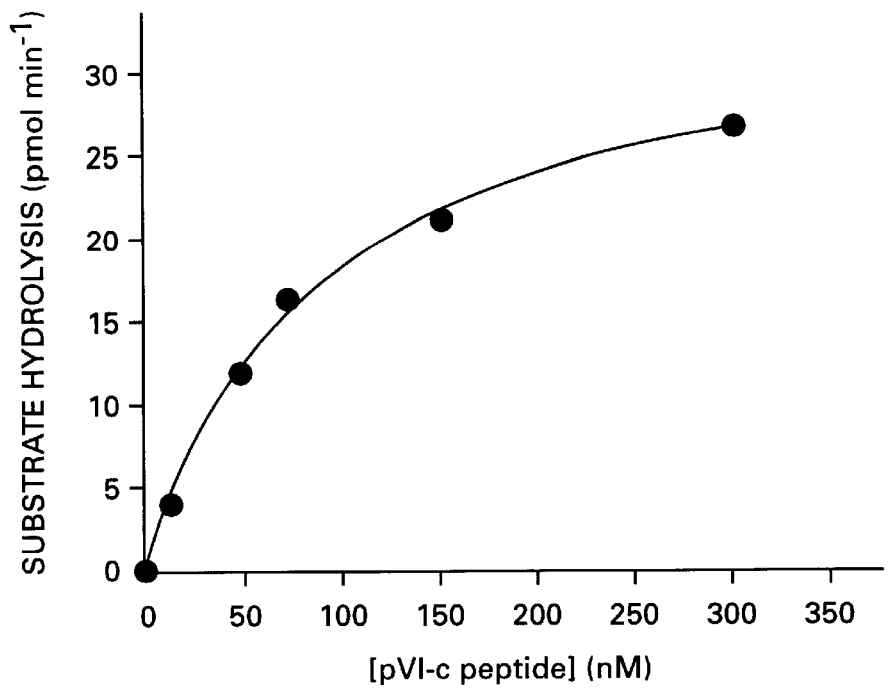
FIG. 13 shows reconstitution of proteinase activity in vitro with purified components: (A) Titration of the pVI-c peptide cofactor; (B) Titration of Ad2 DNA.
Figure 13B:
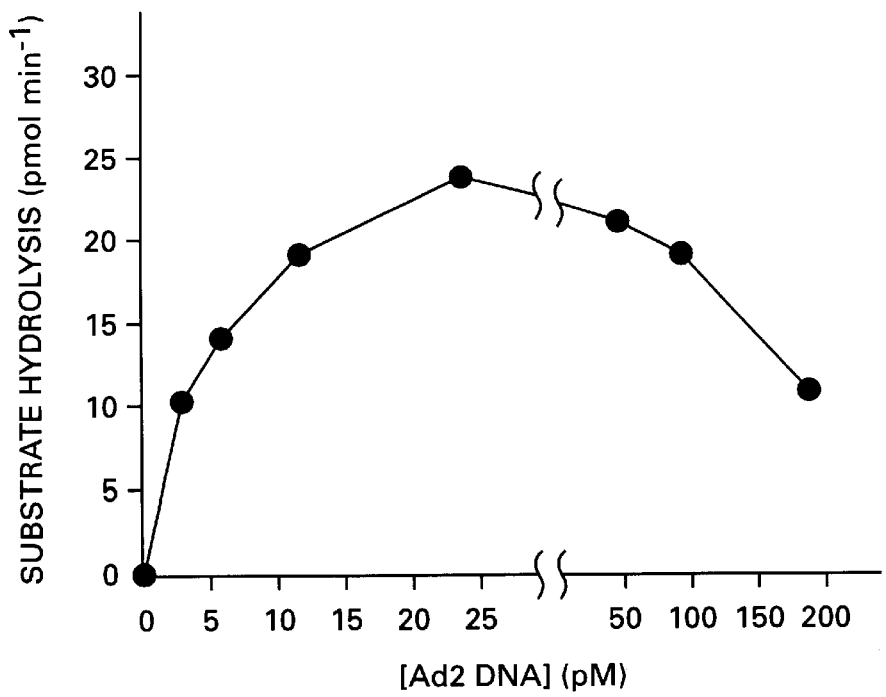

After determining the identity of the two cofactors, reconstitution of adenovirus proteinase activity in vitro with purified components was accomplished. FIG. 13 shows titration with (a) pVI-c peptide and (b) Ad2 DNA. In (a), Assays in 1 ml contained 1.2 nM rEP protein, 11.9 pM Ad2 DNA and the indicated concentrations of pVI-c peptide. The rate of substrate hydrolysis is the rate in the reaction minus the rate with the rEP protein and Ad2 DNA alone which was 0.068 pmol min$^{-1}$. In (b), Assays in 1 ml contained 1.2 nM rEP protein, 36 nM pVI-c peptide and the indicated concentrations of Ad2 DNA. The rate of substrate hydrolysis is the rate in the reaction minus the rate with the rEP protein and pVI-c alone which was 2.76 pmol min$^{-1}$. The concentration of (Leu-Arg-Gly-Gly-NH)$_2$-rhodamine was 5 $\mu$M, and its rate of hydrolysis to Leu-Arg-Gly-Gly-NH-rhodamine was determined by measuring the increase in fluorescence every 3 minutes for 15 minutes. The pVI-c peptide was assembled in a peptide synthesizer.

The Carboxy-Terminal Fragment of Ad12 pVI is Also a Proteinase Co-factor

After the 11-amino acid pVI-c fragment was shown to be a cofactor for Ad2 proteinase, the equivalent fragment from Ad12 was tested for cofactor activity. The equivalent Ad12 fragment differs from the corresponding Ad2 fragment at only two amino acids.

The proteinase activity in disrupted, wild-type Ad12 virions will cleave the HEP1DBP substrate, but the Ad12 virion EP activity is poor compared to the activity from an equivalent number of Ad2 virions. Cleavage of the [$^{35}$S]-methionine-labeled HEP1DBP substrate was greatly enhanced, however, by the presence of purified Ad2 rEP (Example 21). This result showed that Ad12 virions also contain components that complement and activate the Ad2 EP polypeptide.

To determine if the Ad12 carboxy-terminal fragment of pVI functioned as the EP co-factor, the corresponding synthetic peptide was mixed with recombinant Ad2 proteinase and Ad2 DNA, and incubated with the HEP1DBP substrate.

Rapid and complete cleavage of the HEP1DBP substrate was obtained when the incubations contained either Ad12 or Ad2 synthetic pVI carboxy-terminal peptide, but no cleavage was observed in incubations with a control peptide of similar length and composition.

Sequence of the Ad12 genes for pMu and pVI.

Ad2 and Ad12 virions have similar polypeptide compositions but several components differ significantly in apparent molecular weight. Virion precursors pMu and pVI are encoded by adjacent genes in the L3 region of adenovirus genomes, between the genes for the minor core protein (V) and hexon (II). Each of these Ad2 components is cleaved at two EP consensus sites, one near the amino termini, the other near the carboxy termini. Ad2 Mu is a 19 amino acid peptide that binds strongly to DNA; component VI is associated with hexons.

By analogy with the Ad2 genome (Genbank codename ADRCG), the Ad12 genes for pMu and pVI were predicted to lie within the adjacent BamHI endounclease cleavage fragments I, J, and F. These fragments were cloned into the BamHI site of pBR322 and sequenced, using a primer-directed strategy as in Example 8. The Ad12 Bam J fragment is 236 bp long and was sequenced entirely using vector-specific sequencing primers. Both ends of the BamHI I and F fragments were sequenced. Sequence from one end of the F fragment was homologous to Ad2 sequence near the carboxy terminus of pVI and extended toward the hexon gene. A reverse primer, corresponding to sequence near the amino terminus of the hexon gene, was used to obtain the complementary sequence. Sequence from one end of the I fragment was complementary to the late (sense) strand of Ad2, and this sequence was extended to the carboxy terminus of the gene for component V with appropriate primers; the complementary sequence was determined in the same manner. The portion of the sequence determined on both strands is given in SEQ ID NO: 39, together with the deduced amino acid sequences of pMu and pVI. Consensus EP cleavage sites are present in both sequences at positions equivalent to the cleavage sites in the Ad2 percursors.

The Ad12 precursor for Mu has only 72 residues compared to 80 residues for Ad2 pMu; Ad12 Mu has only 15 residues. Ad12 and Ad2 pMu are identical at 45 of 72 amino acid positions (62.5% identity). The main difference in length results from a 15 base pair deletion immediately before the amino-terminal EP cleavage site and a 12 bp deletion after the cleavage site. It is remarkable, therefore, that an amino-terminal EP cleavage site has been retained; however, this cleavage site has not been completely conserved. Ad2 pMu has a type I cleavage site (-LTGGI-|-M-) at this position with glycine at both the P1 and P2 positions, Ad12 pMu has a type II site (-LTGN-|-G-), which has glycines at the P2 and P1' positions. Although changes at the nucleotide level are evident at each of the other three cleavage sites (the carboxy-terminal pMu site and both pVI sites), these sites are more highly conserved.

The carboxy-terminal fragments of the two pMu sequences are highly conserved with identity at 24 of 29 positions (83%). This observation suggests that the carboxy-terminal fragment may be a functional domain that, for example, associates with another virion component. Both central Mu domains are highly basic and are expected to bind strongly to DNA. Thus, pMu may cement the core to the shell or help to condense the core. EP cleavage after assembly would disrupt such associations.

The Ad12 pVI sequence is predicted to be 265 residues in length, fifteen residues longer than Ad2 pVI (Akusjarvi and Persson, 1981). The amino-terminal cleavage fragment of Ad12 pVI is predicted to be 33 residues, the same length as the Ad2 amino-terminal fragment. The carboxy-terminal fragment is 11 residues in length as is the Ad2 fragment (Anderson, 1990). The 15 residue difference in length falls entirely with the body of VI and results primarily from four short insertions in the Ad12 genome. Ad12 VI has a notably slower mobility than Ad2 VI during SDS-polyacrylamide gel electrophoresis. As noted above, the carboxy-terminal halves of Ad12 and Ad2 VI are the least conserved portions of pVI. The two cleavage fragments are highly conserved with most differences due to conservative substitutions. These observations suggest that the terminal domains of pVI also may have biological function.

The Ad12 EP polypeptide is very similar in sequence to the Ad2 EP polypeptide sequence (Houde and Weber, 1988); thus, we expect that the Ad12 EP has similar requirements for cofactors. Although we have not tested this hypothesis directly, the high homology between the carboxy-terminal fragments of Ad12 and Ad2 pVI suggested that the Ad12 fragment might substitute for its Ad2 counterpart; this was found to be the case. Both peptides are very basic (~50% Arg plus Lys), and like Mu, should interact strongly with a polyanion, such as DNA (Anderson et al., 1989). Because of a glutamine-to-lysine substitution at the second position, the Ad12 fragment has one more positively charged residue than the Ad2 fragment. The other amino acid difference is at the carboxy-terminal residue; the Ad12 fragment has a tyrosine in place of the phenylalanine of Ad2. Both fragments have a cysteine at the tenth position, and the effect of derivitizing this residue suggests that it may be important for co-factor activity.

Identification of Ad12 Cleavage Sites.

To determine if the postulated Ad12 pMu and pVI cleavage sites were functional, CsCl-purified Ad12 virions were fractionated as in Example 20, and individual components were subjected to amino acid sequence analysis. Because the cleavage products of Mu and the carboxy-terminal fragment of pVI were expected to be small peptides, virion components were fractionated first by size, using a filter with a molecular weight cut-off of 10,000 Da. After collecting the filtrate from virions disrupted in 10 percent pyridine, the retentate was treated with 1M ammonium bicarbonate to release DNA-bound peptides, and this wash was again subjected to filtration. Peptides in each filtrate were concentrated and then fractionated separately by reverse phase HPLC. Each peptide peak was then subjected to automated Edman degradation. For several components, no sequence was detected. This result was expected because the precursors to adenovirus structural proteins are thought to be acetylated. Clear sequence was obtained, however, for six components. These sequences were homologous to expected cleavage fragments from the Ad2 precursors pIIIa, pVIII, pMu, and pVI. One component corresponded to the predicted fifteen amino acid sequence of Ad12 Mu, another corresponded to the amino terminus of the predicted carboxy-terminal fragment of pMu, and a third to the predicted eleven amino acid carboxy-terminal fragment of pVI. Thus, pMu clearly must be cleaved at the two sites predicted from the Ad2 EP consensus recognition sequence, and pVI is cleaved at the predicted carboxy-terminal site. For the other three fragments that yielded sequence, two are provisionally identified by homology with the corresponding Ad2 sequence for pvIII, and the other by homology with the carboxy-terminus of Ad2 pIIIa. The amino terminus of each fragment corresponds to the position of an EP cleavage site in the corresponding Ad2 protein.

To determine if the amino-terminal pVI site was cleaved, CsCl-purified Ad12 virions were fractionated by SDS-polyacrylamide gel electrophoresis, and the separated polypeptides were transferred electrophoretically to a PVDF (Immobilon) membrane. Portions of the membrane corresponding to the positions of VI and VII were excised and then sequenced. The sequence from VI corresponded to the expected sequence beginning at the predicted cleavage site (FIG. 2). The sequence obtained from Ad12 VII was strikingly similar to the amino-terminal sequence of Ad2 VII. These results indicated that Ad12 pVI cleaved at sites homologous to the Ad2 pVI cleavage sites. The sequence of the Ad12 pVII gene has not been determined and confirms the predicted cleavage site.

Preparation and Characterization of an Anti-Ad2 Proteinase Antibody

Figure 14A:
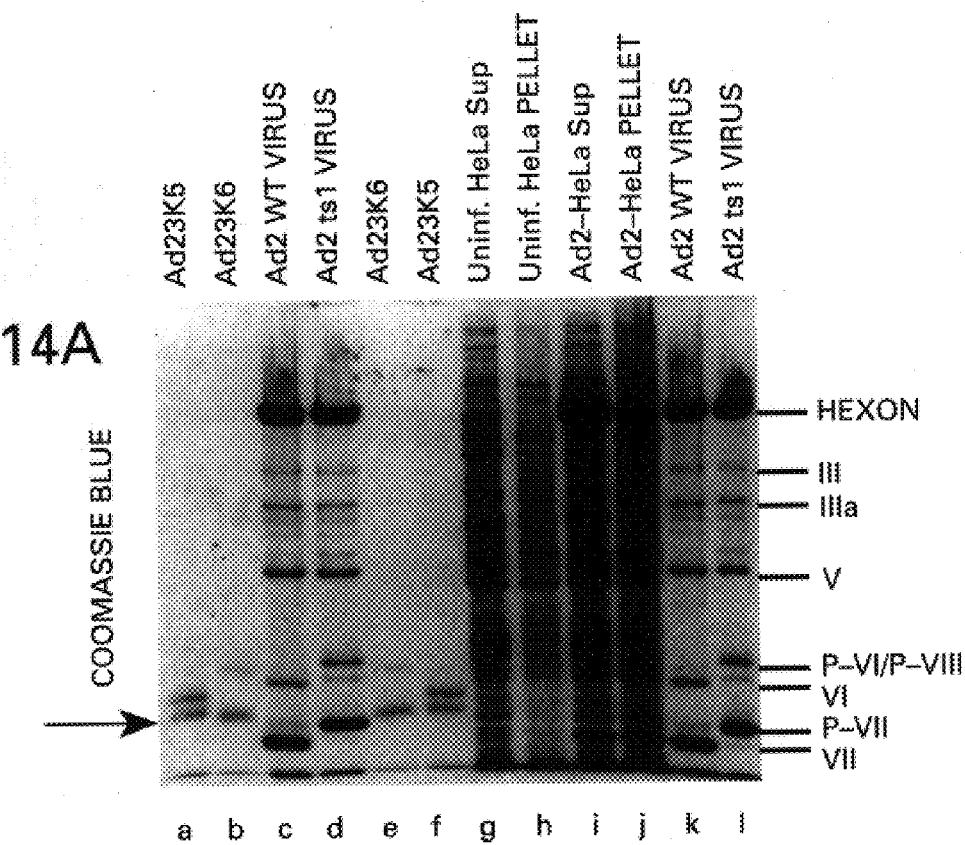
FIG. 14 shows the Western blot analysis of virion-derived and recombinant Ad2 proteinases.

A polyclonal antiserum was prepared by immunizing rabbits with purified 23K1 polypeptide. 23K1 is a fusion protein composed of the T7 gene 10 protein joined to the Ad2 proteinase (Table 2). The antiserum, designated α23K1, was strongly immunoreactive with Ad2 proteinase and not significantly reactive with other adenovirus or mammalian cell proteins (FIGS. 14 and 15). The α23K1 antiserum reacted with Ad2 proteinases in purified virions, virus-infected HeLa cells, and bacterial extracts. It was immunoreactive with wild type Ad2, mutant H2ts1, recombinant fusion (23k5) and recombinant variant (23K11) proteinases. This antibody recognized active (23k6 and 23K10) and inactive (23K11) proteinases. Thus, the α23K1 antibody was characterized as immunospecific for Ad2 proteinase.

Uses of the Invention

This invention provides a method for producing activatable recombinant adenovirus proteinases in nonmammalian and mammalian host cells. The method comprises: a) obtaining an expression construct comprising an adenovirus proteinase coding sequence inserted in a vector suitable for expressing heterologous proteins in a suitable host cell; b) introducing the expression construct into the host cell, thereby, obtaining a host cell containing the expression construct; and c) growing the host cell containing the expression construct under conditions suitable for expressing the adenovirus proteinase coding sequence, thereby, producing host cells which express the recombinant adenovirus proteinase.

This invention further provides expression constructs for producine activatable recombinant adenovirus proteinases in host cells. The expression constructs comprise an adenovirus proteinase coding sequence inserted in a vector suitable for expression of heterologous proteins in the host cell used. Besides bacterial expression vector/host cell systems (such as described above), other expression systems, such as yeast or insect, as well as mammalian expression systems, may be used. The expression constructs are introduced into the host cells by known methods (e.g., transformation, transfection, or infection). The adenovirus proteinase coding sequence may exist as an episome or be integrated into the chromosome of the host cell. Several vector/host cell systems for expressing foreign proteins and methods of introducing constructs into cells have been described in the published literature or are commercially available.

Two proteinase expression constructs of this invention useful for proteinase production are the plasmid pT7AD23k6 and the plasmid pT7AD23K8, whose expression results in the production of activatable recombinant Ad2 proteinase (23k6 and 23K8, respectively). Proteinase variants with altered carboxy-terminal sequences, such as 23K13, can also be synthesized to provide proteinases with additional potentially useful properties. As described above, addition of up to nine amino acids to the carboxy-terminus of the Ad2 proteinase does not appear to have a detrimental effect on activity. In contrast, variants of the Ad2 proteinase which have amino acid additions or deletions in the amino-terminal region are less activatable or inactive. Thus, proteinase expression constructs with alterations of the amino-terminal region of the coding sequence may not be useful for production of functional recombinant proteinase. The above results show that deletions in the amino-terminal region as short as nine codons and additions to the amino-terminus as short as three codons can significantly reduce or abolish the yield of proteinase activity. Post-translational deletion of the initiating methionine does not appear to affect the yield of activity.

pT7AD23k6 can also serve as a prototype for the construction of expression constructs encoding other adenovirus type proteinases. The work described herein demonstrates that activatable recombinant proteinase of an adenovirus (Ad12) from a different subclass can be produced using a plasmid, pT7AD23K16, which follows the design of the prototype construct. A high degree of homology has been demonstrated among the proteinase genes of various serotypes of adenovirus. This DNA sequence homology extends even to serotypes of different host ranges (see, e.g., Cai and Weber, Virology 196, 358 and references therein). Because of this homolgy, production of activatable proteinases of other adenovirus types is expected using the expression constructs and methods taught by this invention. FIG. 16 shows the predicted amino acid sequences of several adenovirus proteinases (Example 19; SEQ ID NO: 2, NO: 6, and NOS: 16–21). Nucleotide sequences encoding these proteinases can be inserted into known expression vectors, such as pET bacterial vectors.

Nucleic acid (DNA or RNA) encoding adenovirus proteinases can be obtained from a number of sources, including adenovirus stock, from cloned adenoviral DNA, and by using polymerase chain reaction techniques. Expression constructs can be obtained using recombinant DNA techniques (see, e.g., Sambrook et al., *Molecular Cloning: A Laboratory Manual*, 2nd *Edition*, Cold Spring Harbor Laboratory Press; Ausubel et al. (eds.), Current Protocols in Molecular Biology, Greene Publishing Associates and Wiley-Interscience, New York).

The activity of other recombinant adenovirus type proteinases can be assayed as described herein for the recombinant Ad2 proteinase. As shown above, recombinant Ad12 proteinase is active in an assay using a substrate (pVII) and cofactors derived from Ad2-infected cells. Furthermore, the cleavage site sequences of the Ad2 and Ad12 pVI precursor proteins are conserved. In addition, heat inactivated Ad12 virions complement the recombinant Ad2 proteinase (23k6 or 23K8) to produce proteinase with even higher activity than is produced with an equivalent number of heat inactivated Ad2 virions. This result suggests that Ad12 co-factors work as well or better to produce an activated enzyme with 23K8 than do the homologous cofactors in Ad2 virions. Thus, an optimal proteinase enzyme may be produced by combining co-factors and sequence elements from different adenovirus serotypes. These may be created and expressed using standard genetic engineering techniques and the teaching provided in this document. These results suggest that all adenovirus type proteinases have very similar or identical cleavage sites.

This invention provides the means to obtain quantities of activatable adenovirus proteinase not previously possible. The recombinant proteinase produced can be purified to near homogeneity as determined by SDS-polyacrylamide gel electrophoresis. The recombinant adenovirus proteinase produced is functional and can be used in studies on the structure, biochemical properties, and function of the adenovirus proteinase. It can also be used to study virion assembly and maturation and virion protein processing in adenoviruses.

As reported herein, activation of the adenovirus proteinase requires two cofactors. The cofactors have been identified and, together with purified recombinant proteinase, have been shown to reconstitute adenovirus proteinase activity in vitro using purified components. Thus, this invention provides preparations of activated adenovirus proteinase and methods for producing the activated preparations.

A preparation of activated adenovirus proteinase consists essentially of an activatable recombinant adenovirus proteinase, polyanion, and a peptide cofactor of adenovirus proteinase activity. The polyanion cofactor can be single-stranded or double-stranded DNA, RNA, polyglutamic acid, polyaspartic acid or heparin.

A peptide cofactor of adenovirus proteinase activity is a protein, generally a short peptide, which is able to activate an activatable adenovirus proteinase in combination with DNA. Peptide cofactors of adenovirus proteinase activity can be identified by a method comprising: a) obtaining a peptide; b) combining the peptide with an activatable recombinant adenovirus proteinase, DNA, and an appropriate substrate of adenovirus proteinase, under conditions suitable for cleavage of the substrate by the recombinant adenovirus proteinase; and c) determining cleavage of the substrate wherein cleavage of the substrate indicates that the peptide is a peptide cofactor of adenovirus proteinase activity.

An appropriate substrate of adenovirus proteinase is any molecule containing the peptide recognition sequence of an adenovirus proteinase. For example, the substrate protein may contain the Ad2 proteinase recognition sequence. The Ad2 EP consensus recognition sequence was determined to be -(L, I, M)-X-G-G|X- or -(L, I, M)-X-G-X|G-, where the vertical line denotes the position of cleavage; the P3 (X) position appears to be unimportant for cleavage [Anderson, C. W., *Virology*, 177;259 (1990); Webster, et al., *J. Gen. Virol.*, 70;3225 (1989)]. As described herein, both recombinant Ad2 and Ad12 proteinases cleave peptides containing this sequence, and it is expected that proteinases of other adenovirus types will also recognize this sequence. A fluorogenic substrate, (Leu-Arg-Gly-Gly-NH)$_2$, has been described. Other peptide-rhodamine substrates have been described in the publications of Walter Mangel. Cleavage of the substrate can be detected by changes in size, for instance, as seen by SDS-PAGE, in fluorescence, or some other property.

A peptide cofactor from Ad2 is described herein, which is 11 amino acids long and has the carboxy-terminal sequence, GVQSLHRRRCF, of the Ad2 protein, pVI (SEQ ID NO: 15), in which the lysine may be modified. This 11 amino acid peptide cofactor can be obtained in crude extracts from adenovirus-, including H2ts1-, infected cells, or purified by the methods described in Example 12. The equivalent 11amino acid carboxy terminal peptide from Ad12 pVI (see SEQ ID NO: 41) can substitute as the peptide cofactor.

Activated adenovirus proteinase preparations can be used to cleave a selected protein at a specific site by a method comprising: a) obtaining a substrate protein comprising the selected protein and an adenovirus proteinase recognition sequence located at the desired cleavage site; and b) combining the substrate protein with an activated adenovirus proteinase preparation. The substrate protein can be constructed using recombinant DNA techniques. The cleavage of the target protein may occur in a purified system or in cellular extracts. The timing of the cleavage event may be controlled by combining the substrate with the proteinase and DNA cofactor, then, initiating the cleavage by adding the peptide cofactor. For example, an activated proteinase preparation used in this method may contain purified recombinant 23k6 proteinase, bacterial DNA, and purified peptide cofactor.

Specific cleavage of proteins can be used to purify proteins or portions of proteins. For example, the method can be used to purify small peptides which are difficult to purify. A fusion protein can be engineered which contains the peptide linked to a reagent moiety with a proteinase cleavage site at the junction of peptide and binding moiety. After the fusion protein is purified through a property conferred on the fusion protein by the reagent moiety, such as specific binding to an affinity column or increased size, the peptide can be purified from the reagent moiety by cleavage of the fusion protein with the activated proteinase preparation.

In another example, a substrate protein can be genetically engineered to contain the proteinase recognition sequence at a position in its primary structure such that cleavage of the protein results in deletion of a functional domain of the protein.

This invention also provides variant or mutant adenovirus proteinases with unusual, potentially useful properties, such as altered cleaving ability. An activatable variant Ad2 proteinase, 23K13, has been described herein. Studies of 23K13 and other proteinase variants (23K11, 23k5) lead to the expectation that other variant proteinases with alterations of the carboxy-terminal region of the proteinase will be functional, but variants with alterations of the amino-terminal region (except loss of the initiating methionine) will be inactive or much less active. For example, a specific deletion of amino-terminal sequences produces an inactive proteinase. It is likely that the deletion or change of conserved residues (as indicated in FIG. 16) will produce inactive or less active proteinase, whereas changes to or insertions at non-conserved sequences may do little harm and may permit engineering of proteinase with enhanced or specialized properties. In addition, a proteinase which would be particularly useful in commercial applications is produced by coupling the carboxy-terminal sequence of pVI to the carboxy terminus of the recombinant proteinase. It is also possible to produce a mutant proteinase that does not require DNA for activity.

Furthermore, this invention provides a method to identify novel variant adenovirus proteinases with altered proteinase activity. The method comprises: a) obtaining a recombinant variant adenovirus proteinase; by combining the recombinant variant proteinase with an adenovirus proteinase substrate, DNA and a peptide cofactor of adenovirus proteinase activity; and c) comparing the activity of the recombinant variant proteinase with that of the wild type proteinase, wherein a difference in activity indicates that the adenovirus proteinase variant has altered proteinase activity.

The primary structure of the proteinase variant can be determined before identification.ming the identification. A mutation resulting in a defective proteinase can then be engineered into an adenovirus strain by recombinant techniques, thus, producing adenovirus strains which are defective in aspects of virion maturation. Such mutant adenovirus strains may be useful as vaccine strains or to produce virions as delivery vehicles for gene therapy. The temperature sensitive mutant Ad2 strain, H2ts1, has been shown to produce immature virions at nonpermissive temperatures, which attach to cells but do not productively infect them (Weber, 1976 supra; Hannan et al., 1983 supra; Mirza et al., 1980 supra).

The above-described method can be used to generate and screen novel adenovirus strains with mutant proteinases. For example, mutant proteinases can be generated by random mutagenesis of a construct such as pT7AD23k6 and produced in *E. coli*. The recombinant proteinases can then be assayed as described previously. Production and preliminary screening of variant adenovirus proteinases in vitro or in fast-growing microbial cell culture can reduce the time and cost of developing improved adenovirus strains.

Analysis of structural variations (or mutations) resulting in altered proteinase activity can also provide insights into adenovirus proteinase function, such as the interaction of the cofactors with the proteinase.

Alternatively, variants of the above-described 11 amino acid peptide cofactops can be generated and identified by a similar method. Variant peptide cofactors with mutations or side-chain modifications of the 11 amino acid peptide can be produced by recombinant techniques, synthesized, and chemically modified. The variant cofactors can then be tested for effect on proteinase activity in assays as described previously. Variations in size and sequence may result in functionally equivalent peptide cofactors of proteinase activity, or they may result in peptides with altered ability to activate adenovirus proteinases. Adenovirus strains with variant cofactors can be engineered by altering the coding sequence of the P-VI protein.

Activated recombinant proteinase preparations can also be used to identify substances which affect proteinase activity agonistically or antagonistically. A method for identifying a substance which is an agonist or antagonist of adenovirus proteinase activity comprises: a) obtaining an activated adenovirus proteinase preparation; b) combining the activated proteinase with the substance; and c) comparing the proteinase activity obtained with the substance to proteinase activity without the substance, wherein a difference in activity indicates that the substance is an agonist or antagonist of adenovirus proteinase activity. Substances identified by this assay method may affect primarily the recombinant proteinase or the peptide cofactor in the preparation. Such substances are expected to affect adenovirus virion production in vivo, and thus, are potential pharmaceuticals for treating adenovirus infections or modulating adenovirus vaccines.

This invention also provides a method for preparing antibodies which are immunoreactive with an adenovirus proteinase. The method comprises eliciting an immune response against a recombinant adenovirus proteinase, or a portion of an adenovirus proteinase. Described herein is a polyclonal antiserum, α23K1, which was prepared by immunizing rabbits with the 23K1 recombinant proteinase. 23K1 is a fusion protein composed of the T7 gene 10 protein fused to the Ad2 proteinase. α23K1 antibody recognizes Ad2 wild type, mutant, and recombinant proteinases but is not significantly reactive with other adenovirus or mammalian cell proteins. Polyclonal and monoclonal antibody preparations immunospecific for a variety of adenovirus proteinases can be prepared by using recombinant proteinases, or portions thereof, as immunogens or as haptens. Techniques for preparing antibodies have been described (see, e.g., Harlow and Lane, Antibodies: A Laboratory Manual, Cold Spring Harbor Laboratory Press, 1988).

Immunospecific anti-proteinase antibodies prepared as described above can be used as immunoprobes for the adenovirus proteinase, for example, in Western blot analysis or in immunoassays. A method for detecting an adenovirus proteinase in a sample comprises: a) obtaining an antibody prepared as described above, which is immunospecific for the adenovirus proteinase in distinction from other adenovirus or mammalian cell proteins; b) combining the antibody with the sample under conditions appropriate for specific binding of the antibody to the adenovirus proteinase in the sample; and c) detecting the specific binding of the antibody to the adenovirus proteinase, wherein specific binding of the antibody indicates the presence of the adenovirus proteinase in the sample.

Immunospecific anti-proteinase antibodies can be used to isolate adenovirus proteinases, for example, by affinity chromatography. They can also be used to study adenovirus virion maturation and structure, and particularly, the function of the adenovirus proteinase. For example, described herein is use of the α23K1 antiserum to identify the Ad2 proteinase peptide, to study the processing of a virion component, to detect the Ad2 proteinase in radiolabeled virions (Example 16), to determine the location of the proteinase in virions (Example 17), and to estimate the number of proteinase polypeptides per virion (Example 18).

In addition, antibodies can be raised against a peptide cofactor of adenovirus proteinase activity. Such antibodies may be useful for investigating the function of the cofactor in activating adenovirus proteinase. Antibodies which neutralize the peptide cofactor may be useful as antiviral agents against adenovirus.

EXAMPLES

The present invention will now be illustrated by the following examples, which are not intended to be limiting in any way.

1. Cells, Viruses, and Viral DNA

HeLa cells were grown in suspension culture in Joklik's modified MEM with 5% bovine serum, or on plates in an atmosphere of 5% $Co_2$ in Dulbecco's modified MEM with 10% bovine serum and without antibiotics. Wild type Ad2 and the mutant, H2ts1 (Weber, *J. Virol.* 17: 462–471 (1976)), were propagated in HeLa cells, as described previously (Anderson, et al., *J. Virol.* 12: 241–252 (1973); Anderson, *Virology* 111: 263–269 (1981)), except that H2ts1 was grown at 34° C. Adenovirus virions were purified by two bandings in pre-formed CsCl gradients, essentially as described previously (Pettersson et al., *J. Mol. Biol.* 73: 125–130 (1973)), except that infected cells were lysed in isotonic buffer containing 0.5% Nonidet-P40 (NP-40), and virions were purified from the low-speed supernatant. Wild type Ad2 and Ad12 viruses can be obtained from the American Type Culture Collection (Rockville, Md). Adenoviral DNA was isolated as described (Anderson et al., *J. Virol.* 48: 31 (1983)).

2. Bacterial Cells, Plasmids, and Plasmid Construction

T7 expression vectors, such as pET-1, pET3, and pET-12 are available from Novagen, Inc. (Madison, Wis.). Vectors pET-1 and pET-3 and the host strain BL21 (DE3) are described by Rosenberg et al. (*Gene* 50: 125–135 (1988)). The pET-12 vectors are similar to pET-1 vectors, but they contain a segment encoding the signal peptide sequence of the *E. coli* outer membrane protein T (OmpT) in place of the amino-terminal fragment of T7 gene 10 (Studier et al., *Methods in Enzvmoloay* 185: 60–89 (1990); Grodberg et al., *Nucleic Acids Res.* 16: 1209 (1988)).

*E. coli* B strain BL21 (DE3) expresses T7 RNA polymerase under control of the lac regulatory elements (Rosenberg et al. (1988) supra). It also lacks the OmpT protein, but has a functional outer membrane signal peptidase.

*E. coli* strain DH-1 was from D. Hanahan (Cold Spring Harbor Laboratory). Proteinase expression plasmids were propagated and maintained in non-expressing host strains (strains which do not express the T7 RNA polymerase), such as DH-1, to minimizselee selection of variants that are not capable of expressing the proteinase or that express inactive proteinase (Hanahan, *J. Mol. Biol.* 166: 557–580 (1983)).

The adenovirus proteinase expression plasmids and their predicted gene products are summarized in Table 2.

In order to construct plasmids encoding the Ad2 proteinase, DNA containing the open reading frame of the Ad2 proteinase (SEQ ID NO: 1) was excised from a preparation of virus DNA and inserted into a bacterial plasmid, using standard cloning techniques. Adenovirus DNA sequences flanking the initiation and termination codons were removed, and recognition sites for the NdeI and SalI restriction enzymes were created 5' of the initiation codon (see FIG. 2). These restriction sites facilitated insertion of the proteinase coding sequence into the expression cassette of the pET-12 bacterial expression vector. The NdeI restriction site permitted placing the proteinase initiation codon at the correct distance (about 10 bp) from the ribosome recognition site (or Shine-Dalgarno sequence) in the pET-12 vector to obtain efficient protein synthesis (see Rosenberg et al., *Gene* 50: 125–135 (1988)).

The Ad2 reading frame (SEQ ID NO: 1) corresponds to nucleotides 21,781 to 22,445 of the nucleotide sequence of the Ad2 genome (Yeh-Kai et al., 1983 supra; Roberts et al., in *Adneovirus DNA: The Viral Genome and Its Expression*, W. Doerfler (ed.), Nijhoff, Boston, pp. 1–51 (1986)). The complete sequence of the Ad2 genome is available from Genbank and other molecular sequence databases.

Plasmid pCA93a contains the PvuII fragment of the Ad2 genome, extending from nucleotide 21,769 to 23,386, cloned with BamHI linkers into the BamHI site of pBR322. The PvuII fragment contains the Ad2 proteinase coding sequence (SEQ ID NO: 1).

Plasmid pT7AD23K1 was constructed by inserting the BamHI to EcoRV fragment of pCA93a (including Ad2 nucleotides 21,769 to 22,667) between the BamHI and the EcoRV sites of the bacterial expression vector pET-1a. pT7AD23K1 encodes a fusion protein; it contains the Ad2 proteinase reading frame inserted behind a 12 codon segment of bacteriophage T7 gene 10 (the gene for the major capsid protein).

Plasmid pT7AD23K2 contains the same Ad2 DNA fragment as pT7AD23K12 but cloned between the BamHI and EcoRV sites of the expression vector pET-12b. It encodes a fusion protein in which the Ad2 proteinase has the signal peptide sequence of the *E. coli* outer membrane protein T (OmpT) attached at its amino-terminus. The OmpT signal peptide sequence directs the fusion protein throught the *E. coli* plasma membrane, where it is cleaved between amino acids Ala$_{20}$ and Ser$_{21}$ by a membrane-associated signal peptidase (FIG. 2; SDQ ID NO: 10).

Plasmid pT7AD23K5 (FIG. 1) is similar to pT7AD23K2 but has the SalI to RI linker sequence just before the proteinase translation initiation codon removed. pT7AD23K5 encodes an OmpT signal peptide-Ad2 proteinase fusion protein (FIG. 2). The inserted Ad2 fragment in pT7AD23K5 was copied from plasmid pT7AD23K2 using the polymerase chain reaction (PCR) technique and two primer oligonucleotides, one sense-strand primer, 5' CCCGTCGACCCATATGGGCTCCAG 3' (SEQ ID NO: 22), which is similar to the coding sequence near the proteinase initiation codon, and a second anti-sense strand primer, 5' GGCCCTTTCGTCTTCAAG 3' (SEQ ID NO: 23), which is similar to the opposite strand at a site just distal to the EcoRI site of pBR322. The first primer has a SalI site (G/TCGAC) incorporated near its 5' end, and an NdeI site (CA/TATG) at the initiating methionine codon (nucleotide 21,778 of the Ad2 genome). After cleavage with SalI and RI, the PCR-produced fragment was ligated to the RI to SalI fragment of pET-12b, resulting in pT7AD23K5.

The prototype plasmid pT7AD23k6 was derived from pT7AD23K5 by removing the small NdeI fragment containing the OmpT leader sequence (see FIG. 2; SEQ ID NO: 3). Thus, unlike its parent plasmid, pT7AD23k6 does not encode a fusion protein. In this construct, the initiation codon for the Ad2 proteinase is immediately preceded by the nucleotides CAT; together with the ATG initiation codon, this sequence forms a recognition site for the NdeI restriction enzyme (CATATG).

Plasmid pT7AD23K10 was derived from pT7AD23k6. It was constructed by replacing the PstI to NdeI fragment of pT7AD23k6 with the equivalent fragment of pET-3c; it has the same proteinase reading frame as pT7AD23k6.

Plasmid pT7AD23K11 has a deletion of the codons for Glu$_5$-Gln-Glu-Leu-Lys-Ala-Ile-Val-Lys$_{13}$ (SEQ ID NO: 2) from the Ad2 proteinase reading frame. It was constructed by PCR amplification of pT7AD23k6 using a sense-strand primer, 5' CCCCATATGGGCTCCTCAGATCTTGGT-TGTGGGCC 3' (SEQ ID NO: 24), which extends from the NdeI site 3' to a point beyond the BglII restriction site in the proteinase reading frame (see FIG. 1), and the same anti-sense primer as was used to make pT7AD23K5. The fragment between the NdeI site and the KpnI site within the proteinase coding sequence was cloned into pT7AD23k6 cut with NdeI and KpnI.

pT7AD23K8 has a unique AflII site at codons 202–204 of the Ad2 proteinase reading frame. This plasmid was constructed by PCR amplification of the proteinase reading frame from pT7AD23k6 using a sense primer with a sequence upstream of the proteinase initiation codon, 5' TAATACGACTCACTATAGGGAGA 3' (SEQ ID NO: 25), and a downstream anti-sense primer containing AflII and BamHI sites, 5' CTTGGATCCATTATTTTTACATGTTCT-TAAGGTGACAA 3' (SEQ ID NO: 26). The amplified fragment was cloned into a pET-3c vector at the NdeI and BamHI sites.

pT7AD23K13 has a nine-amino acid addition, GHHHHHHHNM, to the wild type Ad2 proteinase carboxy-terminus. This plasmid was derived from pT7AD23K8. A doublestranded DNA cassette containing the nine codons between an AflII and a BamHI site was formed by annealing two oligomers: a sense strand oligomer, 5' TTAAGAA-CATGGGTCACCACCACCATCACCATAA-CATGTAAAAATAATG 3' (SEQ ID NO: 27), and a complementary antisense strand oligomer, 5' GATCCATTATT-TTTACATGTTATGGTGATGGTGGTGGT-GACCCATGTTC - 3' (SEQ ID NO: 28). The double-stranded cassette was then cloned into a pT7AD23K8 vector fragment from which the 22 bp AflII-BamHI fragment had been removed.

Plasmids encoding the Ad12 proteinase were constructed similarly, except that the Ad12 proteinase reading frame was copied directly from a preparation of Ad12 viral DNA (Strain Huie) using polymerase chain reaction (PCR) techniques. Amplification was performed using a sense primer for the N-terminus:

5'-CCCGTCGACCCATATGGGTTCAAGC-3' (SEQ ID NO: 29)
SalI NdeI and an antisense primer for the region beyond the carboxy-terminus:
5'-CCCAAGCTTGTACTCCAATG-3'. (SEQ ID NO: 30).
HindIII Using the restriction sites in the primers, the Ad12 proteinase coding sequence was cloned in-frame with the OmpT leader sequence in the pET-12 vector to make pT7AD23K15. pT7AD23K16 was then derived from pT7AD23K15 by removing the NdeI fragment which contains the OmpT leader sequence.

The Ad12 coding sequence (SEQ ID NO: 5) corresponds to nucleotides 127 to 809 of the published sequence of the Ad12 proteinase (Houde and Weber, *Nucleic Acids Res.* 16: 1795 (1988)). This sequence is also available in Genbank; The complete sequence of the Ad12 genome has not been determined.

The recombinant DNA procedures used in plasmid construction have been described (Maniatis et al., *Molecular Cloning: a Laboratory Manual*, Cold Spring Harbor Laboratory, NY (1982)). PCR was performed with Taq polymerase according to the instructions supplied by Cetus, Inc. Oligonucleotide primers were prepared using a Microsyn 1450 oligonucleotide synthesizer manufactured by Systec, Inc.

3. Expression of Recombinant Proteinases in *E. coli*

BL21 (DE3) cells were transformed with each of the above-described plasmids, and transformants were selected for ampicillin resistance as described (Maniatis et al., 1982 supra). Cultures of transformants were grown to mid-log phase (about $5 \times 10^8$ bacteria per ml) at 37° C. in L-broth or in M9 medium containing 40 $\mu$g ampicillin. IPTG was added to 0.4 $\mu$M to induce expression of the proteinase, and the temperature was lowered to 30° C. After incubation for two to six hours at 30° C. in IPTG, the culture was harvested by centrifugation, washed once with Suspension Buffer (50 mM Tris-HCl, p 8.0, 5 mM EDTA, 1 mM mercaptoethanol, 4% glycerol) as described (Rosenberg et al., 1988 supra). Harvested cultures may be stored frozen in Suspension Buffer at −20° or −70° C.

To prepare soluble extracts containing the proteinase, a harvested culture is resuspended in 10 ml Suspension Buffer per 100 ml of initial culture. The bacterial suspension was put through three cycles of freezing in a dry ice-ethanol bath and thawing. The suspension was then incubated with 100 $\mu$g/ml lysozyme for 15 minutes at 37° C. to lyse the bacteria. After addition of $MgCl_2$ to 10 mM and DNAse I to a concentration of 100 $\mu$g/ml, the suspension was incubated for another 15 minutes at 37° C. to degrade DNA and reduce the viscosity. Soluble and insoluble components were separated by centrifugation at 10,000×g for 20 minutes at 4° C. or at 12,000×g (in microcentrifuge tubes) for 10 minutes at room temperature.

FIG. 3 shows the expression of plasmids pT7AD23K5 and pT7AD23k6 in BL21 (DE3) cells after induction. Log-phase cultures of BL21 (DE3) (lanes c and f), pT7AD23K5/BL21 (de3) (lanes d, g, and h), and pT7AD23k6/BL21 (DE3) (lanes e, i, and j) were labeled for 5 minutes with Y$^{35}$S]-methionine at 1 (lanes g and i) and 2 hours (lanes c–f, h, and j) after IPTG induction. Bacterial extracts were prepared immediately after labeling and run on SDS-polyacrylamide gels. Shown are a Coomassie Blue-stained SDS-polyacrylamide gel (left) and an autoradiogram (right) of the gel. Arrows mark the positions of the induced proteinase fusion proteins. Also shown are the polypeptides of purified Ad2 (lane a) and H2tsl (lane b) virions.

As shown in FIG. 3, the recombinant proteinase quickly became the most rapidly synthesized polypeptide after induction, and rapid synthesis continued for more than 2 hours after induction (lanes f–j), even with pT7AD23k6, which makes active Ad2 proteinase. As judged from the Comassie Blue-stained gel, plasmid pT7AD23K5 produced nearly equal amounts of a 25 kDa (23k5a) polypeptide and a 23 kDa (23k5b) polypeptide (lane d). This suggests that the OmpT signal peptide sequence is cleaved from a portion of the pT7AD23K5 expression product. Pulse-chase experiments confirmed that a portion of the 25 kDa polypeptide was rapidly processed to the 23 kDa product. However, the 25 kDa polypeptide that was not processed within about 5 minutes of synthesis was stable, even several hours after synthesis. The sequence analysis summarized in Table 2 shows that the 23 kDa polypeptide begins with serine$_{21}$. Similar results were obtained from expression of pT7AD23K2 (Table 2).

The expressed proteinase polypeptides were then tested for solubility. Induced bacteria were harvested and lysed with lysozyme-EDTA, and 10,000×g supernatants were prepared. In each case, the majority of the proteinase polypeptide was found in the 10,000×g pellet. When pellet fractions were analyzed by SDS-polyacrylamide gel electrophoresis in the absence of a reducing agent, only a small fraction of the proteinase polypeptides entered the stacking gel, showing that most of the bacterially synthesized proteinase was misfolded and crosslinked through disulfide bonds. This finding was true for both pT7AD23K5 products (23k5a and 23k5b) as well as for the 23k6 polypeptide.

4. Assay of Adenovirus Proteinase Activity in Crude Extracts

Adenovirus proteinase activity was monitored by the cleavage of [$^{35}$S]-methionine-labeled major core precursor (pVII) essentially as described (Bhatti and Weber, *Biochem. Biophys. Res. Comm.* 81: 973–797, (1978)). The proteinase substrate was prepared from Ad2Ad2tsl-infected HeLa cells grown at 39° C. and labeled with [$^{35}$S]-methionine (200 $\mu$Ci/plate) from approximately 28 to 30 hours after infection. Labeled cultures were harvested, washed twice in Phosphate Buffered Saline (PBS), resuspended in 1.0 ml of 10 mM sodium phosphate buffer, pH 7.4, per plate, and sonicated for 40 seconds using a water-cooled sonicator horn (Branson Sonic Power Co., Danbury, Conn.). The extract was then centrifuged at 12,000×g for 10 minutes, and the pellet was resuspended in 10 mM phosphate buffer.

Extracts of Ad-infected cells, harvested 40 hours after infection at 37° C. were used as a source of viral proteinase. Harvested cultures were washed twice with PBS, resuspended in 10 mM phosphate buffer, frozen and thawed once, and centrifuged at 12,000×g for 10 minutes. Pellets were resuspended in 1.0 ml phosphate buffer, pH 7.4, per $10^6$ infected cells and sonicated 4×10 seconds; samples were stored at −70° C. Bacterial extracts were prepared by lysozyme-EDTA treatment of cultures harvested 2 hours after IPTG induction.

Assays were performed by mixing equal volumes of [$^{35}$S]-labeled substrate and test extract and incubating at 37° C. At different times, 25 $\mu$l samples were removed, mixed with 25 $\mu$l of SDS Sample Buffer, heated to 90° C., and analyzed by SDS-polyacrylamide gel electrophoresis and autoradiography as described (Anderson et al., *J. Virol.* 12: 241–252 (1973)).

5. Activity of Recombinant Adenovirus Proteinases

Recombinant proteinase polypeptides were assayed for proteinase activity by incubating whole-cell extracts of BL21 (DE3), pT7AD23K5/BL21(DE3), and pT7AD23k6/BL21(DE3), prepared as described above, with extracts of [$^{35}$S]-methionine-labeled Ad2 virion precursor polypeptides. Incubation of the labeled extract at 37° C. for up to 20 hours, alone or with an extract prepared from uninfected HeLa cells, produced little change in the pattern of labeled polypeptides.

FIG. 4 is an autoradiogram of an Ad2 proteinase assay for the processing of pVII by wild type and recombinant Ad2 proteinases. Proteinase assays were performed as described above. An extract prepared from HeLa cells harvested 40 hours after infection with wild type Ad2 (lane b) served as a source of authentic proteinase. Bacterial extracts (unfractionated) were prepared from untransformed BL21 (DE3) (lane e), pT7AD23K5/BL21(DE3) (lane d), and pT7AD23k6/BL21 (DE3) (lane c) 2 hours after IPTG induction. Samples were removed after at different times after induction and analyzed by SDS-polyacrylamide gel electrophoresis; the autoradiogram in FIG. 4 shows the assay at a 90 minute time point. The positions of several Ad2 virion components are given on the right; [$^{35}$S]-methionine-labeled wild type Ad2 virions were applied to lane a.

Incubation with extracts of wild type Ad2-infected HeLa cells caused the rapid disappearance of the major core protein precursor, pVII (lane b), and of L2-79R, the precursor to mu (Anderson, et al., *Virology* 172: 506–512 (1989)). Simultaneously, a polypeptide the size of component VII appeared. Mu and its precursor were not resolved on the gel shown in FIG. 4. Processing of pVI and pVIII was not apparent.

Incubation of the [35S]-methionine-labeled Ad2 polypeptides with extracts prepared from BL21(DE3) (lane e) or from pT7AD23K5/BL21(DE3) (lane c) produced little change in the polypeptide pattern, even after a 20 hour incubation. Two unidentified polypeptides, with a mobility similar to component V, disappeared when incubated with *E. coli* extracts; these components were stable when incubated with infected or uninfected HeLa extracts.

Incubation with an extract prepared from pT7AD23k6/BL21(DE3) caused rapid processing of the precursor, pVII (lane d) and L2-79R (pMu). The amount of processed VII increased as the amount of pVII decreased. By 2 hours virtually all of pVII had been converted to VII. Processing activity in the bacterial extracts was stable for only about 2 hours at 37° C. As judged by the pVII assay, 23k6 proteinase activity was distributed equally between soluble and insoluble fractions of the *E. coli* extract, despite the fact that the majority of the 23k6 polypeptide was in the insoluble fraction.

To confirm that processing by the *E. coli* expressed proteinase was accurate, component VII was purified from a 2 ml assay that was incubated with the pT7AD23k6/BL21 (DE3) extract for 2 hours and its amino-terminus sequence was determined. The expected amino-terminal sequence of component VII (Sung et al., *J. Biol. Chem.* 258: 8266–8272 (1983)), Ala-Lys-Lys-Arg-Ser-Asp-Gln-His-Pro-Val-Arg-Val-Arg$_{13}$ (SEQ ID NO: 31), was observed indicating that pVII had been correctly processed by the recombinant 23k6 proteinase.

Virion component VII was purified from the in vitro cleavage reaction by phosphocellulose chromatography in 40 mM methylamine phosphate, pH 5.6, 6M urea as described (Hosokawa et al., *J. Virol.* 17: 924–934 (1976)). Component VII eluted between 0.4 and 0.8M NaCl. Partially purified virion-derived proteinase and recombinant proteinase polypeptides can also obtained by this method. The virion proteinase elutes from phosphocellulose between 0.1 and 0.4M NaCl.

Although no proteinase activity was observed with extracts prepared from pT7AD23K5/BL21(DE3) 2 hours after induction (FIG. 4, lane c), processing activity was observed in extracts from uninduced cells grown to stationary phase. Extracts from uninduced pT7AD23K1- and pT7AD23K2-transformed cells grown to stationary phase also exhibited proteinase activity. Extracts from uninduced, stationary phase cells which express the proteinase fusion proteins 23k5, 23K1, and 23K2 had less proteinase activity than similarly prepared extracts from cells expressing 23k6. No processing activity was detected in extracts from cells expressing the deletion variant 23K11 after either IPTG induction or growth to stationary phase.

6. Amino-Terminal and Tryptic Peptide Sequencing Methods

Purified (to near homogeneity), carboxymethylated, recombinant proteinases obtained as described in Example 3 were resuspended in 0.1M NH$_4$HCO$_3$, and incubated with approximately 1/50 weight trypsin at 37° C. for 6 hours. The vacuum-dried digest was resuspended in 20% formic acid, clarified by centrifugation at 12,000×g for 10 minutes, and applied to a C8 reverse-phase column (Aquapore RP-300, 4.6×220 mm from Pierce Chemical co., Rockford, Ill.) equilibrated in 0.1% trifluoroacetic acid (TFA). Peptides were eluted with a linear gradient of acetonitirile in 0.1% TFA at 1 ml/minute; the column was monitored at 214 nm, and 1 ml fractions were collected.

Tryptic peptide and amino-terminal sequences were determined as described (Anderson, *Genetic Engineering: Principles and Methods*, Setlow et al. (eds.), 4: 147–167 (1982); Lees-Miller and Anderson, *J. Biol. Chem.* 264: 2431–2437 (1989); Lees-Miller and Anderson, *J. Biol. Chem.* 264: 17,275–280 (1989) using an Applied Biosystems 470A "gas-phase" sequencer with a Model 120 on-line PTH analyzer and Hewlett-Packard 3396A integrator (Applied Biosystems, Inc., Foster City, Calif.). Amino acid compositions were determined using the Aminoquant system manufactured by Hewlett-Packard after hydrolysis of samples with 6N HCl in vacuo at 110° C.

7. Peptide Sequence Analysis of Recombinant Proteinases

The amino-terminal sequence obtained for each recombinant proteinase is indicated (by underlining) in Table 2. In each case analyzed, the amino-terminal sequence obtained was that expected from the structure of the plasmid encoding the recombinant proteinase. Exceptions were the expression products of pT7AD23k6, pT7AD23K8, pT7AD23K10, and pT7AD23K16, which had a mixture of proteinase amino-termini with and without the initiating methionine. The relative amounts of the two amino-termini differed from experiment to experiment for each expression product.

Amino-terminal sequence analysis allowed prediction of the exact size of each recombinant proteinase (Table 2). This prediction assumes that the structure of the cloned reading frame is correct and that no processing occurred at the carboxy-terminus. To confirm these assumptions, the structure of 23k6 was analyzed in greater detail.

Figure 5:
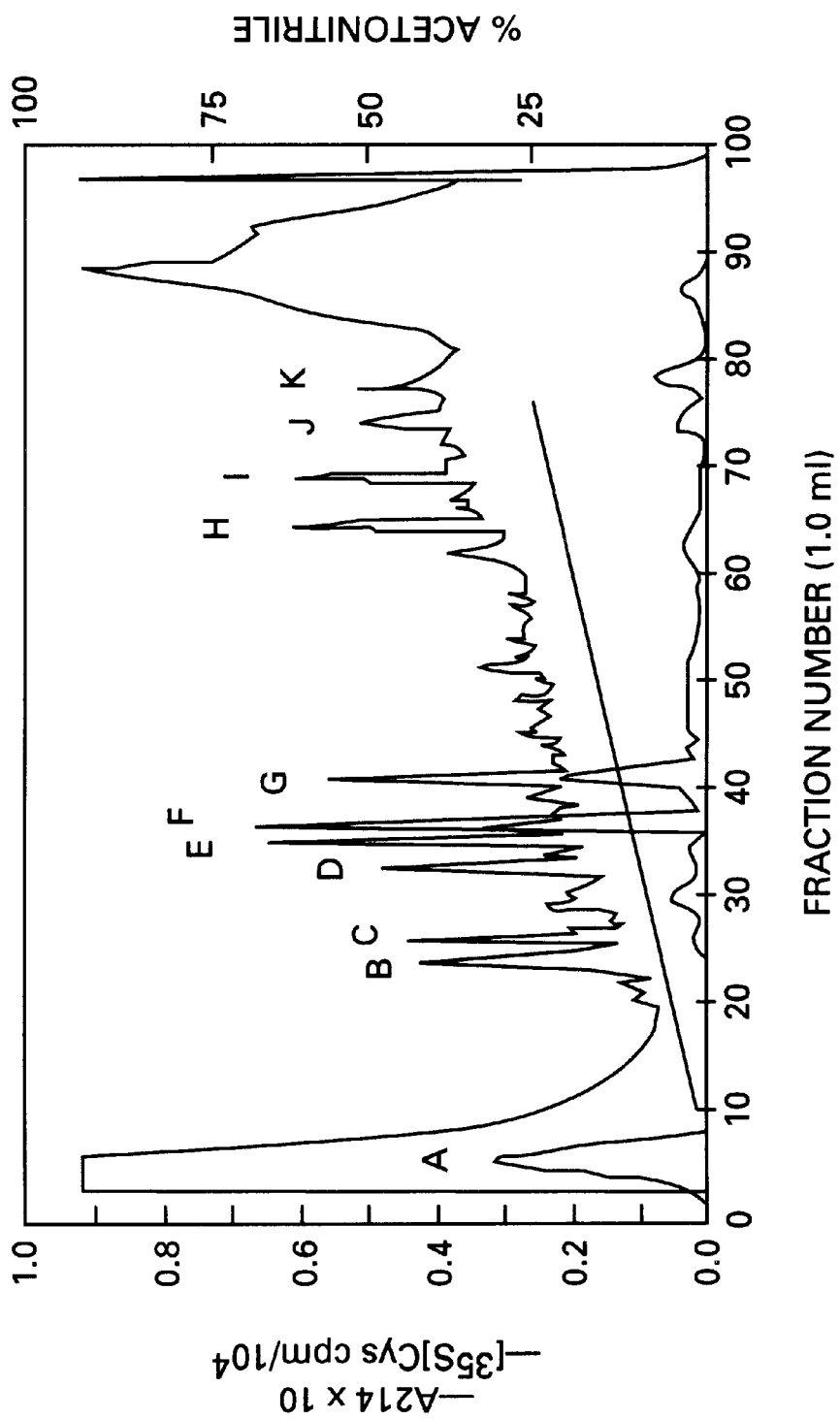
FIG. 5 is a chromatogram of tryptic peptide fractions of 23k6.

About 100 μg of bacterially produced 23k6 polypeptide were labeled with [$^{35}$S]-cysteine, carboxymethylated to disrupt disulfide bonds, and then digested with trypsin. The peptides that were soluble in 20% formic acid were applied to a C8 reverse phase column equilibrated in 0.1% TFA, and eluted with a gradient of acetonitrile. FIG. 5 shows a chromatogram indicating the acetonitrile gradient (dotted line) and the elution profile as detected at 214 nm (solid line) or by scintllation counting (short dashed line). Six tryptic peptides with eight cysteines distributed among them are predicted from the Ad2 proteinase amino acid sequence (SEQ ID NO: 2). The prominent peaks are labeled with letters. The chromatogram shows that while eight unlabeled peptides were detected by absorption at 214 nm, only three peaks of radioactivity were found in the chromatogram and only a quarter of the radioactivity was soluble after trypsin digestion, suggesting that some of the adiolabeled cysteines were in hydrophobic tryptic eptides. This was confirmed by radiochemical sequence nalysis of the insoluble fraction after trypsin igestion, indicating the presence of $Cys_{17}$ and/or $Cys_{67}$, $Cys_{122}$, $Cys_{126}$, and $Cys_{127}$ in the insoluble fraction. The three [$^{35}$S]-cysteine-containing peaks and several of the unlabeled tryptic peptides were analyzed for amino acid content and amino-terminal sequence.

Fractions 6 and 7 contained three expected dipeptides corresponding to Ser-$Lys_{65}$, Leu-$Lys_{81}$, and Asn-$Met_{204}$. Asn-Met is the predicted carboxy-terminal tryptic dipeptide of the Ad2 proteinase. Carboxymethylcysteine was not detected in fraction 65 or 7 by amino acid analysis, nor was a cysteinecontaining peptide observed after sequence analysis. The radioactivity in fractions 6 and 7 may have resulted from unincorporated [$^{35}$S]-cysteine.

[$^{35}$S]-Cysteine-labeled peptides were detected in fractions 37 and 42. Sequence analysis identified the peptide Cys-Ile-Thr-Leu-Glu-$Lys_{109}$ (see SEQ ID NO: 2) in fraction 37 (peak F), and Ser-Ala-Thr-Ser-Phe-Cys-His-Leu-$Lys_{202}$, the carboxy-terminal cysteine-containing peptide, in fraction 42 (peak G). Other identified internal tryptic peptides included: Gln-Val-Tyr-Gln-Phe-Glu-Tyr-Glu-Ser-Leu-Leu-$Arg_{93}$ (peak I); Ser-Ala-Ile-Ala-Ser-Ser-Pro-Asp-$Arg_{103}$ (peak C); Asn-Gln-Glu-Gln-Leu-Tyr-Ser-Phe-Leu-Glu-$Arg_{180}$ (peak H); His-Ser-Pro-Tyr-Phe-Arg-Ser-His-Ser-Ala-Gln-Ile-$Arg_{193}$ (peak B); and the related peptide His-Ser-Pro-Tyr-Phe-$Arg_{186}$ (peak E). Peak D is a peptide that extends from $Ser_{187}$ through the carboxy-terminus of the proteinase. (Peak C was not identified; peaks J and K have not been analyzed.)

In summary, amino-terminal and tryptic peptide sequence analysis together directly confirmed one-third of the predicted sequence of the 23k6 proteinase (FIG. 6). Peptide analysis therefore supports the conclusion that 23k6 is exactly the 204 (or 203 without the initial methionine) amino acid Ad2 proteinase predicted from the nucleotide sequence of the Ad2 genome (SEQ ID NO: 1).

8. Cloning and DNA sequencing of Ad12

Ad12 DNA was cleaved with BamHI and the resulting fragments were cloned into the BamHI site of plasmid pBR322 by standard techniques (Sambrook et al., 1989). Plasmid pPF2109 carries the Ad12 BamHI J fragment, pPF2112 carries the BamHI I fragment, and pPF2137 carries the BamHI F fragment.

The DNA sequence was obtained by the dideoxynucleotide triphosphate terminator method using Sequence version 2.0 (U.S. Biochemical, Cleveland, Ohio) and oligonucleotide primers. Both strands of the reported sequence were determined. Where required, band compressions were resolved by performing parallel reactions with dITP.

9. Preparation and Yield of Purified Activatable Recombinant Ad2 Proteinase

Growth and induction of plasmid-containing BL21 (DE3) strains, harvesting, and lysis were described [Anderson, C. W., *Virology*, 177;259 (1990)] [Studier, W. F. et al., *methods enzymol.* 185;60 (1990)] except that the incubation temperature for growth was 30° C. instead of 37° C. After clarification by centrifugation at 10,000 g for 10 min, the lysate from 100 ml of culture was applied to a DEAE column (~3-ml bed volume) equilibrated in 50 mM Tris-HCl, pH 8.0, 1 mM DTT, and the flow-through was collected. Pooled flow-through fractions were dialyzed briefly (~2 h) against 50 mM Tris-HCl, pH 8.0, 100 mM NaCl (Zn-column buffer) to remove EDTA and then applied to an ~2-ml (per 100 ml of culture) column of iminodiacetic (IDA or chelating) Sepharose (Pharmacia-LKB, Inc.) saturated with $Zn^{2+}$ [Hochuli, E. et al., *J. Chromatogr,* 411;177 (1987)] and equilibrated in the same buffer. After washing with 5 column vol of Zn-column buffer containing 25 mM imidazole, then 5 vol of 50 mM Tris-HCl, pH 8.0, 1.0M NaCl, and finally 1–2 vol of Zn-column buffer without imidazole, the proteinase was eluted with 25 mM EDTA, pH 8.0, containing 100 mM NaCl. The EDTA-eluted proteinase was concentrated by centrifugation using a Centricon 10 concentrator (Amicon, Inc.), washed once or twice by centrifugation with 25 mM Tris-HCl, pH 8.0, containing 2.5 mM DTT and 10 mM octglucoside (EP Assay Buffer), and stored at −70° C.

The yield of purified proteinase was determined with the Bio-Rad dye-binding assay using BSA as the standard. HEP1DBP was purified from pT1HEP1DBP/BL21(DE3) cells by the same procedure. In some cases, cultures were labeled with [$^{35}$S]methionine after induction as described [Anderson, C. W., *Virology*, 177;259 (1990)].

For cation-exchange chromatography on MonoS, the column was equilibrated in 25 mM Hepes, pH 7.5, 0.2 mM EDTA, and 0.1 mM DTT, and elution was with a linear gradient of KCl in the same buffer. Gel filtration on Superdex 55 HR30/10 was in 25 mM Hepes, pH 8.2, 0.02% NP-40, and 0.2 mM DTT. Buffers were applied using the fast protein liquid chromatography (FPLC) system (Pharmacia-LKB) at room temperature.

A 100 ml culture yields approximately 200 μg of adenovirus proteinase purified to near homogeneity. The eluted proteinase is highly active in the presence of cofactors, even in the absence of divalent metal ions, such as zinc. Induced cultures of *E. coli* transformed with pT7AD23k6 can yield 1 to 2 mg of purified, active recombinant Ad2 proteinase per liter of culture.

10. Production of Activatable Recombinant Proteinase in a Baculovirus Vector/Insect Cell Expression System A baculovirus vector (vNPVAd2EP) was made which expresses the Ad2 proteinase. The Ad2 coding sequence from pT7AD23K8 was cloned into a baculovirus transfer vector, pETL, and transferred to the nuclear polyhedrosis baculovirus by transfection and plaque purification; the Ad2 proteinase gene replaces the polyhedron protein gene in the vector. Recombinant baculovirus vNPVAd2EP was constructed as follows:

1. A DNA fragment containing the proteinase gene from pT7AD23K8 was produced by PCR using the primers:

BNL#937 N-Terminal sense-strand PCR primer for Ad2 proteinase. This primer contains an NdeI site at the proteinase initiation sequence and is homologous to the first 13 nucleotides of the Ad2 proteinase gene.

BNL#937 5' TTTTGCTAGCATGGGCTCCAGTG 3' (SEQ ID NO: 38)

BNL#430 This primer is homologous to sequence at the RI site in pBR322 and in pET vectors. It may be used in combination with pET vector promoter primers, or other sense strand primers, to copy by PCR genes inserted into the expression site of pET vectors. The copies sequence will include an RI site corresponding to that in pBR322.

BNL#430 5' GGCCCTTTCGTCTTCAAG 3' (SEQ ID NO: 34)

2. The PCR amplified fragment from pT7AD23K8 was cleaved with NheI and BamHI and the proteinase gene fragment was purified by agarose gel electrophoresis.

3. The PETL vector was cleaved with NheI and BamHI and was purified.

4. The proteinase gene from #2 was ligated with the cleaved vector, and the ligation products were used to transform DH5. Plasmid DNA from several independent colonies was characterized by restriction analysis and four were selected for future use. These became CWA Lab Strains #239A, #239B, #239C, and #123D.

5. DNA from two of these were mixed (separately) with DNA from wild type baculovirus (ACNVP) from P. Tegtmeyer, State University of New York, Stony Brook; the DNA is also available commercially from BRL and Invitrogen). The mixture was used to transfect Sf9 cells by the calcium phosphate techique.
6. After incubation to produce recombinant virus, the lysate was placques on Sf9 cell monolayers overlayed with agar containing Bluo-Gal (BRL Cat. No. 5519UA/UB according to recommendations provided by BRL (Baculovirus Plaque Assay and Purification, GIBCO/LTI, 2/91). Well isolated blue colonies were picked and the virus in these was amplified by infection of Sf9 cells. GIBCO BRL Life Technologies, Inc., 8400 Helgerman Court, Gaithersburg, Md. 20877; (Corporate Headquarters).
7. The resulting virus was tested for expression of proteinase by infection of Sf9 cells. After about 48 hr, the infected cells were harvested, and the proteins in these extracts were analyzed by SDS-polyacrylamide gel electrophoresis and Western blotting. Plaques were chosen for further purification based on the amount of proteinase expressed detected by Western blotting using the 23K1 polyclonal serum, and the (low) level of polyhedron protein (from contaminating wild type virus).
8. Recombinant virus was purified by two additional rounds of plaque purification following standard virology practices, and a high titer stock was produced.
9. The stock was used to infect Sf9 cells, and the expression of proteinase polypeptide was confirmed by Western blotting experiments.
10. An extract of Sf9 cells was prepared by freeze-thaw lysis, and proteinase was prepared from the soluble fraction by DEAE- and zinc-affinity chromatography, as described for purification of proteinase from bacterial extracts.

Recombinant Ad2 proteinase was partially purified from Sf9 cells infected with the recombinant baculovirus by the same procedure for purifying proteinase from bacteria, as described in Example 9. The recombinant proteinase, which was about 5% pure, was shown to have a specific activity equivalent to that of bacterially-produced proteinase using the fluorescence assay, Ad2 DNA and H2ts1 virions to provide cofactor.

Methods, baculovirus vectors, and Sf9 cells have been described (Summers, Max D. and Smith, Gale E., *A Manual of Methods for Baculovirus Vectors and Insect Cell Culture Procedures*, Texas Agricultural Experiment Station Bulletin No. 1555, Texas Agricultural Experiment Station and Texas A&M University College Station, Texas 77843–2475, (409) 845–9730 (1988); Chen et al., *J. Virology* 65(10): 5131–5140 (1991); Vialard et al., *J. Virology* 64(1): 37–50 (1990)). pETL can be obtained from Dr. Christopher D. Richardson, Biotechnology Research Institute, 6100, avenue Royalmount, Montreal, Quebec, Canada H4P 2R2.

11. Assays for Adenovirus Proteinase Activity

Artificial proteinase substrate was expressed upon induction of a pET expression plasmid called pT1HEP1DBP (or pT7HIS2).

Plasmid pT7HEP1DBP (5346 bp) is a pET-3 derivative that expresses the 231-amino acid T7 gene 2.5 protein (a single-stranded DNA binding protein) attached to a 17-amino acid leader sequence (FIG. 19). The 249-amino acid HEP1DBP polypeptide serves as an artificial substrate for the adenovirus EP; the leader peptide, MASMTGHHHHHHGMSGG- (SEQ ID NO: 37), ends with the Ad2 proteinase recognition sequence -MSGG- (SEQ ID NO: 38) [Anderson, C. W., *Virology*, 177;259 (1990)], which is found at the carboxy terminus of the amino-terminal cleavage fragment of virion precursor pVI [Akusjarvi, G. and Persson, H., *J. Virol.*, 38;469 (1981)] [Sung, M. T. et al., *J. Biol. Chem.*, 252;4981 (1977)]. The six consecutive histidine residues in the leader permit the product to be purified by zinc-affinity chromatography [Hochuli, E. et al., *J. Chromatogr*, 411;177 (1987)] [Kagedal, L., *Methods, and Applications* (J-C. Janson and L. Ryden, Eds.), VCH Publishers, NY, 227 (1989)] [Arnold, F. H. and Haymore, B. L., *Science*, 252;1796 (1991)]. pT7HEP1DBP was constructed from elements of plasmid pT7AD23K13 and plasmid p3505; p3505 contains the T7 2.5 gene. First, the 595-bp segment of the pT7AD23K13 from the BstEII site to the ECPRI site was copied using PCR and oligonucleotide primers 5'-CCTA CATATGGCTTCTATGACTGGTCACCACCA-3' (sense strand) (SEQ ID NO: 35) and 5'-GGCCCTTTCGTCTTCAAG-3' (SEQ ID NO: 34). The latter oligonucleotide corresponds to anti-sense sequence just counterclockwise (toward the bla gene) of the EcoRI site in pET-3. The amino-terminal sense strand primer provided an NdeI site with a methionine initiation codon followed by a sequence that encodes the first 6 amino acids of the leader and then a sequence homologous to pT7AD23K13 from the BstEII site at the beginning of the oligohistidine track. After cleavage with NdeI and EcoRI, the amplified fragment was ligated with similarly cut pT7AD23K13 to make the intermediate plasmid pT7His1. Next, the T7 gene 2.5 segment was copied from plasmid p3505 using the amino-terminal sense strand primer 5'-CCC GGTCACCACCACCATCACCATGGTATGAGCGGCGGC ATGGCTAAGAAGAT- 3' (the BstEII recognition sequence and homology to gene 2.5 are underlined) (SEQ ID NO: 36 and the EcoRI site primer, 5'-GGCCCTTTCGTCTTCAAG- 3' (SEQ ID NO: 23). After cleavage with BstEII and EcoRI, the amplified fragment was ligated with similarly cleaved pT7HIS1 DNA to produce pT7HEP1DBP (FIG. 19).

Assays were performed in 400 µl of Assay Buffer (50 mM Tris-HCl, pH 7.4, 25 mM NaCl, 10 mM octylglucoside, and 1 mM dithiothreitol). The concentration of the fluorogenic substrate, (Leu-Arg-Gly-Gly-NH)$_2$-rhodamine was 5 µM. When present, the number of disrupted virus particles was $10^{10}$ and the amount of recombinant proteinase was 0.12 mAU$_{280\ nm}$. (mAU$_{280}$: One thousandth the absorbance of light at 280 nm passing through a 1 cm pathlength. Typical proteins give an optical density at 280 nm of between 0.5 and 2 when dissolved at a concentration of 1 mg/ml. The extinction coefficient for 23k6 has not been determined experimentally, but theoretical calculations suggest that a 1 mg/ml solution of pure 23k6 should have an optical density of about 1). After 30 minutes at 37° C., a 360 µl aliquot of the reaction was added to 340 µl of Assay Buffer minus octylglucoside, and the increase in fluorescence was measured. The excitation wavelength was 492 nm and the emission wavelength was 523 nm, both with a bandwidth of 5 nm. The change in fluorescence, ΔF, is the magnitude of the fluorescence from the sample minus the magnitude of the fluorescence from an identical solution without enzyme.

Disrupted virus was obtained as follows: Twice CsCl-banded virus was dialyzed against 10 mM Tris-HCl, pH 8.0, 1mM EDTA and centrifuged at 100,000×g for 1 hour. The pellet was suspended in 10 mM Tris-HCl, pH 6.8, containing 20% (v/v) glycerol and, after three 10 second bursts of sonication, was stored at −20° C. The fluorogenic substrate was synthesized and purified at BNL by Dr. Walter Mangel, using methods similar to those previously described by Dr. Mangel. These methods are described in two U.S. Patents (U.S. Pat. No. 4,557,862 entitled "Rhodamine derivatives as fluorogenic substrates for proteinases" by Mangel, W. F., Leytus, S., and L. Helhado; issued Dec. 10, 1985; U.S. patent application Ser. No. 780,552; "Novel rhodamine derivatives as fluorogenic substrates" by Mangel, W. F., Leytus, S., and L. Helhado; filing date Sep. 24, 1985) and in other publications by Mangel and co-workers.

DNase-treated disrupted virus was obtained by incubating $2 \times 10^{10}$ disrupted virions in 20 µl containing 0.1M NaAc, pH 5.0, 5 mM $MgCl_2$, and 55 µg/ml DNase I for 4 minutes at 25° C. Then, EDTA to 23 mM and dithiothreitol to 2.3 mM were added, and the reactions were heated at 56° C. for 1 minute to inactivate the DNase.

For the assays shown in FIG. 8, the DNase reactions were diluted by the addition of 380 µl Assay Buffer containing the substrate, the proteinase and either $2 \times 10^{10}$ molecules of Ad2 DNA (+) or no DNA (-). After 30 minutes at 37° C., 360 µl of the reactions were added to 340 µl Assay Buffer minus octylglucoside and the increase in fluorescence was measured. The assays in (B) and (C) were identical to those in (A) except that in (B) H2ts1 virus was added after the DNase was inactivated (i-DNase) and in (C) no Dnase was present. In (D) recombinant proteinase plus $10^{10}$ molecules of Ad2 DNA were preincubated for 10 minutes at 37° C. before adding substrate.

Plasmin-treated disrupted virus was obtained by incubating $4 \times 10^{10}$ disrupted virons in 20 µl of 10 mM Tris-HCl, pH 8.0, 1 mM EDTA, and 33 nM plasmin for 4 minutes at 37° C. Dithiothreitol was added to 2 mM and the solution heated at 56° C. for 1 minute to inactivate the plasmin.

For the assay shown in FIG. 9A, virions and proteinase were preincubated for 10 minutes at 37° C. before adding substrate. The assay in (C) was identical to that in (B) except the plasmin incubated with disrupted virus had previously been inactivated (i-plasmin) by heating to 56° C. in the presence of 2 mM dithiothreitol.

12. Purification and Characterization of the Peptide Cofactor

Purification of the peptide cofactor was performed in two steps. In the first step, Ad2 virus (about $5.8 \times 10^{12}$ virions), purified twice by density gradient centrifugation, was suspended in 0.8 ml of 10 mM Tris-HCl, pH 8, 1 mM EDTA and 10% pyridine. After 1 hour at 25° C., the solution was centrifuged at 12,000×g for 6 minutes. The pellet was resuspended in 0.8 ml of 0.01M Hepes, pH 8, and centrifuged at 12,000×g for 6 minutes. The pellet was resuspended in 0.8 ml of 0.01M Hepes, ph 8, 0.01M octylglucoside and 0.001 mEDTA, and then centrifuged at 5,000×g in a Centricon-30 until 90% of the liquid flowed through the membrane. To the liquid that was retained, the volume was inreased to 0.8 ml with $NH_4C_2H_3O_2$ such that its concentration was 1M. The Centricon-30 was again centrifuged at 5,000×g until greater than 90% of the liquid flowed through the membrane. Assays were performed in the presence of the recombinant proteinase and in the absence or presence of 778 ng/ml Ad2 DNA.

In the second step, the flowthrough from the second Centricon-30 was evaporated to dryness, dissoved in 0.1% trifluoroacetic acid, and applied to a $C_{18}$ reverse phase column (Aquapore OD-300 7 µ, 100 nm long with a 2.1 mm diameter; Pierce Chemiaal Co., Foster City, Calif.). The activity was eluted by a linear gradient from 0–30% acetonitrile in 0.1% trifluoroacetic acid at a rate of 1%/minute.

Assays of fractions from peaks a, b, and c were performed (FIG. 11). The amino acid sequences of the proteins in peaks a–c were determined in a gas phase sequencer, as shown in FIG. 12 (amino acids 240–250 of SEQ ID NO: 15). The "?" at position 6 in this figure indicates a variable yield of lysine.

The two adenovirus proteinase consensus cleavage sequences in pVI are underlined, and the location of the peptide cofactor sequence beginning at position 240 is printed in bold. The amino acid sequence of pVI was from Roberts et al. (1986 supra).

The amino acid sequence of the peptide cofactor is consistent with the bcochemical data. The peptide cofactor was sensitive to plasmin, because it contains three arginine residues. The peptide was not in the flowthrough after the first Centricon-30 centrifugation, because it is a very basic protein and was probably bound to the viral DNA. High ionic strength would dissociate it from the viral DNA, and thus, after the second Centricon-30 centrifugation, it was in the flowthrough. Before the second Centricon-30 centrifugation, fluorescence assays for the peptide cofactor did not require Ad2 DNA, but after the centrifugation, there was an absolute requirement for the DNA. Consistent with the peptide cofactor being a small protein are the observations that boiling for 5 minutes did not irreversibly denature it, that at high ionic strength it flowed through a Centricon-3, and when incubated in 5M urea, it rapidly regained activity upon dilution of the urea.

13. Preparation of Anti-Ad2 Proteinase Serum and Western Blot Analysis of Adenovirus Proteinase Polyclonal antibody against Ad2 proteinase was prepared using the 23K1 polypeptide as an immunogen. 23K1 is a proteinase fusion protein consisting of 12 amino acids of the T7 gene 10 protein fused to the Ad2 proteinase. 23K1 fusion protein was produced from transformed BL21(DE3) cells as described in Example 3. 23K1 protein was solubilized from lysed bacterial pellets with SDS Sample Buffer and fractionated by preparative SDS-polyacrylamide gel electrophoresis. Gels were stained briefly with Coomassie Blue, destained with 50% methanol and 10% acetic acid, and then dried. Gel segments containing the proteinase polypeptide were rehydrated in phosphate-buffered saline (PBS), homogenized, and injected intradermally or subcutaneously at approximately monthly intervals into the backs of New Zealand White (female) rabbits, as described (Zorn and Anderson, J. Virol. 37: 759: 769 (1981)). Blood was withdrawn from the ear 10 and 15 days after each injection; serum was separated from whole blood by centrifugation.

For Western blot analysis, sample proteins were separated by SDS-polyacrylamide gel electrophoresis, then, electrophoretically transferred to nitrocellulose or to Immobilon PVDF (Millipore, Inc., Bedford, Mass.) membranes at 80 V for 30 minutes in Transfer Buffer (25 mM Tris-HCl, about pH 8, 192 mM glycine, 25% methanol) using a Bio-Rad Mini-gel transfer tank. Immunological detection was accomplished following manufacturer's suggested methods (Bio-Rad Richmond, Calif.). Immunological probing with α23K1 antibody was performed at a 1/200 to 1/800 dilution of the unfractionated hyperimmune rabbit serum. Alkaline phosphatase-conjugated anti-rabbit IgG was used for the secondary antibody.

14. Immunodetection of the Ad2 Proteinase

α23K1 antiserum was used to detect bacterially produced Ad2 proteinases and viral Ad2 proteinases from purified wild type and mutant H2tsl virions and Ad2-infected HeLa cells. Ad2 virons were purified by banding in CsCl gradients, as described by Anderson (Viroloav, 1990). Purified recombinant proteins were prepared by HPLC, as described previously. Sample proteins were routinely applied to two parallel SDS-polyacrylamide gels. One gel was stained with Coomassie Blue, dried, and exposed to X-ray film to reveal the migration pattern of the radiolabeled polypeptides. The second gel was electrophoretically transferred to an Immobilon membrane and probed with α23K1 serum to reveal the position of the Ad2 proteinase polypeptides. The immunoblot was then exposed to X-ray film to detect the [$^{35}$S]-labeled Ad2 virion proteins in a control lane. To assist in aligning the immunoblot with the Coomassie Blue-stained gel, small amounts of purified recombinant proteinases 23k5a, 23k5b, and 23K6, labeled with [$^{35}$S]-methionine, were analyzed on each gel.

FIG. 14 shows the identification of the Ad2 proteinase polypeptide in isolated virions and Ad2-infected HeLa cells on SDS-polyacrylamide gel electrophoresis and Western immunoblots. Samples were analyzed by SDS-polyacrylamide gel electrophoresis on identical 10% gels: one gel was stained with Coomassie Blue (A); the other gel was electrophoretically transferred to an Immobilon membrane and probed with α23K1 rabbit serum (B). Lanes a and f show the HPLC-purified proteinase fusion protein products of plasmid pT7AD23K5 (23k5a and 23k5b were mixed). Lanes b and e show HPLC-purified 23k6. Lanes c and k show proteins from purified wild type Ad2 virions. Lanes d and l show proteins from purified Ad2tsl virions. Lanes g and h show the supernatant and pellet fractions, respectively, of freeze-thaw lysed uninfected HeLa cells. Lanes i and j show comparable fractions of Ad2-infected HeLa cells harvested 40 hours after infection.

The Western blot (B) shows that the recombinant proteinases 23k6 (lanes b and e) and processed 23k5b (lanes a and f) have a mobility indistinguishable from that of the virion-derived wild type Ad2 proteinase (lanes c and k). A polypeptide of the same mobility was detected in Ad2-infected HeLa cells (lanes i and j), but not in uninfected cell extracts (lanes g and h). More Ad2 proteinase was present in the insoluble 12,000×g pellet (lane j) than in the soluble, low-salt supernatant fraction (lane i). Comparison of the immunoblot, its autoradiogram, and the parallel Coomassie Blue-stained gel showed that the viral Ad2 proteinase had a mobility during SDS-polyacrylamide gel electrophoresis intermediate between that of pVII and VII.

FIG. 15 shows Western blots of proteinases from Ad2 and H2ts1 virions. Virion proteins were separated on a 17.5% SDS-polyacrylamide gel and transferred to Immobilon. Identical filter sets were incubated overnight without rabbit antiserum, with pre-immune serum at 1/500 dilution (left blot) and with hyperimmune α23K1 serum at 1/500 dilution (right blot). Samples shown are: (lane a) proteins from 4×10$^{10}$ wild type Ad2 virions; (lane b) proteins from 5.3× 10$^{10}$ H2ts1 virions; (lane c) purified 23K10 (recombinant Ad2 proteinase); and (lane d) purified 23K11 (Ad2 proteinase variant with amino-terminal deletion). The positions of Ad2 virion components, determined from an autoradiogram of the immunoblot, are indicated at the right; 79R is the precursor to μ.

The mobility of the proteinase in H2ts1 virions (lane f) was indistinguishable from that in wild-tpe virions (lane e) and from the recombinant proteinase 23K10 (lane g). As expected, the recombinant proteinase variant 23K11 (lane h), which is only 194 amino acids long due to a deletion in the amino-terminal region, migrated distinctly quicker than the wild type proteinase.

No smaller immunoreacting polypeptides were detected in gels that resolved virion proteins of less than 10 kDa (lanes e and f). This suggests that the Ad2 proteinase is not itself proteolytically processed.

Figure 14B:
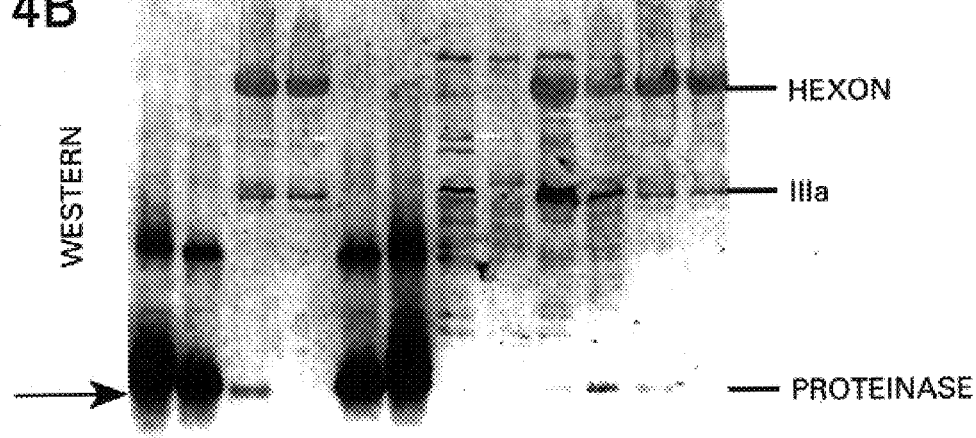

The α23K1 antiserum reacted strongly with the purified recombinant proteinases produced in bacteria, even though these were barely visible by Coomassie Blue staining (FIG. 14B, lanes a, b, e, and f). Reconstruction experiments demonstrated that the sensitivity of immunodetection with the α23K1 antiserum was less than one 23k6 polypeptide per virion under the conditions for Western blot analysis described herein.

The Ad2 proteinase of purified H2ts1 virions was not detected in the western analysis illustrated by FIG. 14. However, as shown in FIG. 15, the proteinase was readily detected when more H2ts1 virions were applied to the gel. A similar difference between amounts of proteinases in Ad2 and H2ts1 virions was observed in virion radiolabeling experiments (FIG. 17). Based on these results, it is estimated that H2ts1 virions contain approximately 5-fold less proteinase than wild type virions. This amount is near the detection limit of the immunoblot assay (about 0.1 ng proteinase) unless gel lanes are overloaded with virus.

15. Immunospecificity of the α23K1 Antibody for the Ad2 Proteinase

FIGS. 14 and 15 testify to the immunospecificity of the α23K1 polyclonal antibody for Ad2 proteinase and its nonreactivity with other adenovirus or mammalian cell proteins. The anti-23K1 serum was made using a gel-purified recombinant proteinase fusion protein, and care was taken to insure that materials used for immunization were not contaminated with virion polypeptides. In FIG. 15, lanes e and f containing purified wild type and mutant Ad2 virion samples indicate no significant reaction of the α23K1 antibody with adenovirus proteins other than the approximately 23 kDa proteinase. The weak immunoreaction observed with virion component IIIa is due to other immunoreactive components in the serum, as shown by lanes a and b in the blot incubated with preimmune serum. Lanes c, d, k, and l of the Western blot in FIG. 14B, which also contain Ad2 virion proteins, confirm this result. The FIG. 14 blot shows an additional weak immunoreaction with the adenovirus hexon protein. The hexon band is a background band resulting from nonspecific reaction with the antiserum: it results because the FIG. 14 blot was developed for maximum sensitivity, and also because the lot of alkaline phosphatase-conjugated anti-rabbit IgG used for this experiment gave a relatively high background. A comparison of the relative amounts of the hexon and proteinase proteins as indicated by Coomassie Blue stain (8A) contrasted with the relative intensity of immunoreaction with the antiserum (8B) further demonstrates the immunospecificity of the α23K1 antibody for Ad2 proteinase and lack of significant immunoreactivity with other adenovirus proteins.

In the Western blot of FIG. 14B, lanes g, h, i, and j, containing extracts from infected and uninfected HeLa cells, show no significant reaction of the α23K1 antibody with proteins other than the approximately 23 kDa Ad2 proteinase band, in either the soluble or insoluble fractions of uninfected and infected HeLa cell extracts. This indicates that the α23K1 antibody is also not significantly immunoreactive with mammalian cell proteins.

Furthermore, the 23K1 antiserum did not react with virion component VII that was separated from the proteinase polypeptide by chromatography on phosphocellulose in urea.

FIGS. 14 and 15 show that the α23K1 antiserum reacts strongly and specifically to wild type and mutant (or variant) Ad2 proteinases from purified virion, infected mammalian cell, and recombinant bacterial cell sources. The antibody is immunoreactive with active as well as inactive Ad2 proteinase, as shown by FIG. 15, lane h, containing the deletion variant 23K11. In lanes containing HPLC-purified recombinant proteinases (lanes a, b, e, and f of FIG. 14 and lane h of FIG. 15), an immunoreactive upper band is seen.

This upper band probably represents a differently folded form of the recombinant Ad2 proteinase, since it is not seen in the virion or infected cell lanes. The upper band protein is present in amounts not detectable by Coomassie Blue staining (FIG. 14A); however, the immunoreaction is strong. This indicates a specific reaction of the antibody to this upper band protein.

16. Detection of the Ad2 Proteinase in [$^{35}$S]-Cysteine and $^{32}$PO$_4$-Labeled Virions The Ad2 proteinase is expected to have eight cysteine residues, while component VII and its precursor have none. Ad2 and H2ts1 virions were labeled with [$^{35}$S]-methionine, [$^{35}$S]-cysteine, and $^{32}$PO$_4$, and run on an SDS-polyacrylamide gel. Ad2 virions were labeled with [$^{35}$S] methionine or cysteine by incubating cells with the radioactive amino acid in medium (Dulbecco's MEM) containing 5% of the normal concentration of that amino acid as described by Anderson, (*Virology*, 1990), usually from about 24 to 36 hr after infection.

FIG. 17 shows an autoradiogram of the gel. The film was exposed for 18 days at −70° C. with an intensifying screen. Only the region of the autoradiogram between virion components pVI and VII is shown. Lanes a and b show Ad2 and H2ts1 virions labeled with [$^{35}$S]-methionine, respectively; lanes c and d show the two virions labeled with [$^{35}$S]-cysteine; and lanes e and f show the virions labeled with $^{32}$PO$_4$. HPLC-purified 23k6 (lane g) and 23k5a and b (lane h) were run as markers for the Ad2 proteinase. The position of the Ad2 proteinase (arrow) was determined from an immunoblot of a parallel gel probed with α23K1 antiserum. Asterisks mark the positions of faintly [$^{32}$P]-labeled polypeptides with mobilities similar to the Ad2 proteinase.

In FIG. 17, distinct, [$^{35}$S]-cysteine-labeled polypeptide was observed in wild type virions between the positions of pVII and VII (lane c). Significantly less [$^{35}$S]-cysteine was present at this position in H2ts1 virions (lane d) even though equal amounts of wild type and H2ts1 virions were loaded on the gel. Confirmation that the cysteine-labeled polypeptide is the proteinase was obtained by comparing a parallel immunoblot with the autoradiogram. The [$^{35}$S]-cysteine-labeled band and the proteinase polypeptide had exactly the same mobility, and, in this experiment, both methods revealed the proteinase as a very closely spaced doublet.

The Ad2 proteinase was previously reported to be phosphorylated (Chatterjee and Flint, *Proc. Natl. Acad. Sci. USA* 84: 714–718 (1987)). In FIG. 17, a faint [$^{32}$P]-labeled component of wild type virions was observed having the mobility of the Ad2 proteinase (lane e), providing further evidence that the Ad2 proteinase is phosphorylated. A faintly labeled polypeptide with slightly higher mobility was observed in H2ts1 virions (lane f). This [$^{32}$P]-labeled component did not correspond to a known Ad2 polypeptide, nor was a proteinase-related polypeptide detected at this position by Western blot analysis. Analysis of virions labeled to high specific activity with [$^{35}$S]-methionine (lanes a and b) showed that virion preparations contain numerous unidentified polypeptides or peptide fragments at low abundance.

The precursor to virion component VI, which is predicted to contain one cysteine residue near its carboxy-terminus, was well labeled with [$^{35}$S]-cysteine; however, no [$^{35}$S]-cysteine was detected at the position of component VI in wild type virions (lanes c and d). Components pVI and VI were peadily observed with Coomassie Blue and stained with equal intensity. This result suggests that pVI may be processed at a second site near its carboxy-terminus.

17. Location of the Proteinase in Virions

To locate the proteinase polypeptide in virions, pyridine-disrupted wild type virions were fractionated into shell components and cores by sucrose gradient centrifugation as described (Prage at al., *Virology* 42: 341–358 (1970)). Each gradient fraction was analyzed for polypeptide content by SDS-polyacrylamide gel electrophoresis (FIG. 18A), and the proteinase was detected by immunoblot analysis of a parallel gel (FIG. 18B). Specifically, purified wild type Ad2 virions (approximately 10$^{12}$ particles) were disrupted by incubation in 10% pyridine as described (Prage et al. (1970) supra), and virion cores were separated from outer shell components by centrifugation through a 15–25% sucrose gradient at 160,000 ×g for 165 minutes at 4° C. using a Beckman SW-41 rotor. Fractions of 1.5 ml were collected, concentrated, and analyzed on parallel SDS-polyacrylamide gels (lanes e-k). One gel was stained with Coomassie Blue (A). The proteins in the other gel were electrophoretically transferred to Immunobilon, which was then processed for immunological detection of the proteinase using α23K1 serum (B). Also analyzed on each gel were Ad2 virions (lanes a, b, 1, and m) and HPLC-purified 23k6 proteinase (lane c). Lane d (marked "B") is pelleted material that was washed from the bottom of the centrifuge tube; lane k was the top ("T") fraction of the gradient. The position of the proteinase is marked with arrows; the positions of other virion proteins are shown at the right.

Although some proteinase was distributed throughout the gradient, the majority was found in fractions containing core proteins V and VII.

18. Number of Proteinase Polypeptides per Virion

The polypeptides from 2.5×10$^9$, 10$^{10}$, and 3×10$^{10}$ wild type Ad2 virions (1.0 A$_{260}$=1.1×10$^{12}$ virions, according to Maizel et al., Virology 36: 115–125 (1968)) were fractionated by SDS-polyacrylamide gel electrophoresis along with two-fold increments of purified 23K10 and 23K11 proteinases in amounts between 0.48 and 7.5 ng per lane. The concentrations of HPLC-purified 23K10 and 23K11 were determined by densitometry of a second, Coomassie Blue-stained gel that was loaded with 100 times as much recombinant polypeptide. The staining intensity of 23K10 and 23K11 was compared to 1.5 and 0.75 μg of soybean trypsin inhibitor (SBTI) that was also fractionated on this gel. The concentration of the stock solution of SBTI was determined by quantitative amino acid analysis. Polypeptides from the first gel were electrophoretically transferred to Immobilon and Ad2 proteinase was detected with α23K1 serum. The proteinase band from 1×10$^{10}$ virions produced the same staining intensity with anti-23K1 serum as approximately 2 ng of 23K10 or approximately 5 ng of 23K11. These amounts correspond respectively to 5 and 13 molecules of proteinase per virion.

19. Other Adenovirus Type Proteinases

The adenovirus proteinase amino acid sequences shown in FIG. 16 are predicted from the proteinase coding sequences, which have been published and are available from Genbank. References of the published nucleotide sequences are listed below:

Human Ad2: Akusjarvi et al., *Nucleic Acids Res.* 9: 1–17 (1981);

Human Ad3: Houde and Weber, *Nucleic Acids Res.* 16: 11,374 (1988);

Human Ad4: Houde and Weber, *Gene* 54: 51–56 (1987);

Human Ad5: Kruijer et al., *Nucleic Acids Res.* 8: 6033–6042 (1980);

Human Ad12: Houde and Weber, *Nucleic Acids Res.* 16: 7195 (1988);

Human Ad 40 and 41: Vos et al., *Virology* 163: 1–10 (1988);

Bovine Ad3 (BAd3): Cai et al., *Nucleic Acids Res.* 18: 5568 (1990); and

Bovine Ad4 (BAd4): Cai et al., *Nucleic Acids Res.* 18: 5567 (1990).

20. Fractionation and sequence analysis of Ad12 Virion Components

This procedure for fractionating virus components was developed for identifying the peptide cofactor required for Ad2 proteinase activity. Approximately $8 \times 10^{12}$ Ad12 virions suspended in 0.01 M Tris-HCl, pH 8, 0.001 M EDTA, 10% pyridine were disrupted by incubating the suspension at 0° C. for 30 min and then rapidly freezing and thawing the suspension. Virion components then were fractionated by size using a Centricon-10 (Amicon, Inc.) filter unit. After an initial concentration by centrifugation, the retentate was washed with 2 ml, then 0.5 ml of water, and then 1.0 ml and 0.5 ml of 1 M ammonium bicarbonate. The water washes and initial filtrate were combined, concentrated to dryness by vacuum centrifugation, and then resuspended and dried several times from water. The bicarbonate extractions were similarly combined, dried, and washed. The retentate was dissolved in SDS buffer and fractionated by SDS gel electrophoresis. Components VI and VII were obtained individually for protein sequence analysis after electrophoretic transfer of the proteins from an SDS-polyacrylamide gel to high capacity PVDF (Immobilon) sequencing membrane (Millipore, Cat. No. ISEQ26260) in CAPS buffer containing 0.05% SDS. The two filtrates (the pyridine and bicarbonate washes) were fractionated by reverse phase high performance liquid chromatography (HPLC) on a 2.1×100 mm C18 column (Aquapore OD-300, 7 micron) equilibrated in 0.1% trifluoroacetic acid (TFA) using a Hewlett-Packard 1090 liquid chromatograph equipped with a diode array detector. The flow rate was 0.5 ml per min and peptides were eluted with a linear gradient of acetonitrile in 0.1% TFA.

Proteins and peptides were sequenced by automated Edman degradation using an Applied Biosystems 470A sequencer equipped for on-line detection of the phenylthiohydantoin-amino acid derivatives.

21. Ad12 virion-mediated cleavage of an artificial proteinase substrate

[$^{35}$S]Methionine-labeled HEP1DBP substrate was incubated with $1 \times 10^{11}$ disrupted Ad12 virions alone, or with Ad12 virions and ~5 μg purified recombinant Ad2 EP polypeptide. Samples were removed after 0, 30, and 120 min incubation at 50° and fractionated by SDS-polyacrylamide gel electrophoresis. An autoradiogram was made from the dried gel.

Equivalents

Those skilled in the art will recognize, or be able to ascertain using no more than routine experimentation, many equivalents to the specific embodiments of the invention described herein. Such equivalents are intended to be encompassed by the claims.

TABLE 2

Adenovirus Proteinase Expression Plasmids and Products

| Plasmid[a]/Vector | Parent Plasmid | Protein Name | Size[b] kDa | aa | Amino-Terminal Sequence[c]/Protein Structure | Activity/Conditions |
|---|---|---|---|---|---|---|
| pT7AD23K1 pET-1a | pCA93a | 23K1 | 25 | 220 | ASMTGGQQMGRDPAAAMGSSEQELKAIVKD- T7 gene 10 (12) + linker (4) + Ad2 PTNase (204) | Active Uninduced, stationary phase |
| pT7AD23K2 pET-12b | pT7AD23K1 | 23K2a | 26 | 231 | MRAKLLGIVLTTPIAISSFASTDPAAAMGSSEQE- OmpT (23) + linker (4) + Ad2 PTNase (204) | Active Uninduced, stationary phase |
| | | 23K2b | 24 | 211 | STDPAAAMGSSEQELKAIVKDLGCGPYFLGTYDK- OmpT (3) + linker (4) + Ad2 PTNase (204) | |
| pT7AD23K5 pET-12b | pT7AD23K2 | 23K5a | 26 | 227 | MRAKLLGIVLTTPIAISSFASTHMGSSEQE- OmpT (22) + linker (1) + Ad2 PTNase (204) | Active Uninduced, stationary phase |
| | | 23K5b | 23 | 207 | STHMGSSEQELKAIVKDLGCPYFLGTYDKRFP- OmpT (2) + linker (1) + Ad2 PTNase (204) | |
| pT7AD23K6 | pT7AD23K5 | 23K6 | 234 | 204/203 | (M)GSSEQELKAIVKDLGCGPYFLGTYDKRFP- Ad2 PTNase | Active Induced, log phase |
| pT7AD23K8 pET-3c | pT7AD23K6 | 23K8 | 23 | 204/203 | (M)GSSEQELKAIVKDLGCGPYFLGTYDKRFP- Ad2 PNTase with AflII site | Active Induced, log phase |
| pT7AD23K10 pET-3C | pT7AD23K6 | 23K10 | 23 | 204/203 | (M)GSSEQELKAIVKDLGCGPYFLGTYDKRFPG- Ad2 PTNase | Active Induced, log phase |
| pT7AD23K11 pET-12b | pT7AD23K6 | 23K11 | 22 | 194 | GSSDLGCGPYFLGTYDKRFPGFVSPHKLACAIV- Ad2 PTNase variant ($E_5$QELKAIVK$_{13}$ deleted) | Inactive |
| pT7AD23K13 pET-3c | pT7AD23K8 | 23K13 | 24 | 213/212 | (M)GSSEQELKAIVKDFLGCGPYFLGTYDKRFPT- Ad2 PNTase variant (GHHHHHHNM at carboxy-terminus) | Active Induced, log phase |
| pT7AD23K15 pET-12b | pT7AD23K5 | 23K15a | 26 | 229 | MRAKLLGIVLTTPIAISSFASTHMGSEQE- OmpT (22) + linker (1) + Ad12 PTNase (206) | Not determined |

TABLE 2-continued

Adenovirus Proteinase Expression Plasmids and Products

| Plasmid[a]/ Vector | Parent Plasmid | Protein Name | Size[b] kDa | aa | Amino-Terminal Sequence[c]/ Protein Structure | Activity/ Conditions |
|---|---|---|---|---|---|---|
| | | 23K15b | 24 | 209 | STHMGSSEQELKAIVKDLGCGPYFLGTYDKRFP-OmpT (2) + linker (1) + Ad12 PTNase (206) | |
| pT7AD23K16 pET-12b | pT7AD23K15 | 23K16 | 23 | 206/205 | (M)GSSEQELTAIVRDLGCGPYFLGTFDKRFPG-Ad12 PTNase | Active Induced, log phase |
| pT7AD23K18 pET-3c | pT7AD23K8 | H2ts1 | 23 | 204/203 | (M)GS SEQELKAIVKDLGCGPYFLGTYDKRFP-ts Ad2 PNTase with AflII site; P to L mutation in codon 137 | Temperature-Sensitive |

[a]The Ad2 proteinase expression plasmids contain the Ad2 genome segment between nucleotide 21,778 at the initiation codon in the L3 23 kDa reading frame and 22,667 at the EcoRV site in the DBP gene. pCA93a, pT7AD23K1, and pT7AD23K2 also have the short sequence between the Ad2 PvuII site at 21,770 and the proteinase initiation codon. The Ad12 proteinase expression plasmids contain nucleotides 127 to 809 of the published sequence of the Ad12 proteinase (Houde and Weber, Nucleic Acids Res. 16:1795 (1988)).
[b]Predicted molecular weight for the expected polypeptide products of the plasmids. aa = amino acids.
[c]The predicted amino-terminal sequences of approximately 30 amino acids is given; residues confirmed by sequence analysis are underlined. Gaps in the confirmed sequence indicate a technical problem in identification of the PTH amino-acid derivative and do not imply that the sequence obtained differed from the predicted sequence. Removal of the amino-terminal methionine was incomplete for 23K6, 23K8, 23K10, 23K11, 23K13, and 23K16.
The predicted protein structure is given; the number of amino acids derived from each part is indicated in ( ). PTNase = proteinase.

TABLE 3

Activaton of Ad2 proteinase activity by negatively charged polymers

| Effector* (concentration) | Rate † (pmol substrate min$^{-1}$) | Stimulation ‡ (fold) |
|---|---|---|
| None | 2.8 | 1.0 |
| Double-stranded DNA | | |
| Linear | | |
| Ad2 (5.9 pM) | 25.6 | 9.3 |
| T7 (2.5 pM) | 26.1 | 9.5 |
| Circular | | |
| SV40 (27.9 pM) | 24.4 | 8.9 |
| φX174 RF (18 pM) | 23.3 | 8.5 |
| Single-stranded DNA | | |
| Linear | | |
| M13 (+ strand) (61 pM) | 27.0 | 9.8 |
| Circular | | |
| φX174 (+ strand) (107 pM) | 26.5 | 9.6 |
| Four deoxyribonucleoside monophosphates (112 nM) | 2.6 | <1.0 |
| RNA | | |
| Yeast tRNA (10.2 nM) | 19.8 | 7.2 |
| Protein | | |
| Polyglutamic acid (2.4 nM) | 24.5 | 8.9 |
| Polyaspartic acid (12 nM) | 13.7 | 5.0 |
| Polylysine (33 nM) | <10.0 | <1.0 |
| Amino acids | | |
| Glutamic acid (780 nM) | 2.3 | <1.0 |
| Aspartic acid (1.38 µM) | 2.1 | <1.0 |
| | 12.9 | 4.7 |
| Heparin (33 nM) | 12.9 | 4.7 |

*The concentrations of effectors in units of moles of molecules per liter that gave maximal stimulation of proteinase activity.
† All assays contained 8.3 nM rEP protein, 98 nM pVI-c peptide, and 1 µM (Leu—Arg—Gly—Gly—NH)$_2$-rhodamine. The rate of substrate hydrolysis by the rEP protein alone was less than 0.014 pmol substrate min$^{-1}$; in presence of 5.9 pmol Ad2 DNA, the rate of hydrolysis was 0.135 pmol substrate min$^{-1}$.
‡ The rate of hydrolysis of substrate in the presence of effector divided by the rate in its absence.

We claim:

1. A bacterial cell transformed with a plasmid selected from the group consisting of:
   a. pT7AD23K1;
   b. pT7AD23K2;
   c. pT7AD23K5;
   d. pT7AD23k6 (ATCC Deposit No. 68322);
   e. pT7AD23K8;
   f. pT7AD23K10;
   g. pT7AD23K11;
   h. pT7AD23K13;
   i. pT7AD23k15;
   j. pT7AD23K16; and
   k. pT7AD23K18.

2. An isolated nucleic acid having the nucleotide sequence SEQ ID NO: 39.

3. The plasmid pT7AD23K18.

* * * * *